(12) United States Patent
Madhani et al.

(10) Patent No.: US 8,123,740 B2
(45) Date of Patent: Feb. 28, 2012

(54) ROBOTIC APPARATUS

(75) Inventors: Akhil J. Madhani, Glendale, CA (US);
J. Kenneth Salisbury, Jr., Los Altos, CA (US); Gunter D. Niemeyer, Mountain View, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 2259 days.

(21) Appl. No.: 10/893,613

(22) Filed: Jul. 15, 2004

(65) Prior Publication Data
US 2005/0043718 A1    Feb. 24, 2005

Related U.S. Application Data

(62) Division of application No. 09/508,871, filed as application No. PCT/US98/19508 on Sep. 18, 1998, now Pat. No. 6,786,896.

(60) Provisional application No. 60/059,395, filed on Sep. 19, 1997.

(51) Int. Cl.
*A61B 19/00* (2006.01)

(52) U.S. Cl. ........... 606/1; 606/130; 128/898; 700/247; 700/250; 700/253; 901/9; 901/15

(58) Field of Classification Search .......... 600/102–108; 606/10–14; 700/260; 901/2–18, 46
See application file for complete search history.

(56) References Cited

U.S. PATENT DOCUMENTS

| | | |
|---|---|---|
| 4,942,538 A | 7/1990 | Yuan et al. |
| 5,078,140 A | 1/1992 | Kwoh |
| 5,182,641 A | 1/1993 | Diner et al. |
| 5,217,003 A | 6/1993 | Wilk |
| 5,222,499 A | 6/1993 | Allen et al. |
| 5,305,203 A | 4/1994 | Raab |
| 5,368,015 A | 11/1994 | Wilk |
| 5,382,885 A * | 1/1995 | Salcudean et al. .......... 901/9 |

(Continued)

FOREIGN PATENT DOCUMENTS
WO    WO 95/01757    *    1/1995

OTHER PUBLICATIONS

Alexander, III Impacts of telemation on modern society, *Intl. Centre for Mechanical Sciences, 1st CISM-IFToMM Symposium, on Theory and Practice of Robots and Manipulators*, (Sep. 5-8, 1973) vol. II, pp. 122-136.

(Continued)

*Primary Examiner* — david shay

(57) ABSTRACT

A robotic apparatus has eight actuators (M0-M7) and a linkage (LINK 0-LINK 5) that actuates an end effector. Three serial macro freedoms have large ranges of motion and inertias. Four serial micro freedoms have small ranges of motion and inertias. Translation of the end effector in any direction is actuated by at least one micro joint and at least one macro joint. The apparatus can be part of a master and slave combination, providing force feedback without any explicit force sensors. The slave is controlled with an Inverse Jacobian controller, and the mater with a Jacobian Transpose controller. A slave having more degrees of freedom (DOFs) than the master can be controlled. A removable effector unit actuates its DOFs with cables. Beating heart surgery can be accomplished by commanding the slave to move with a beating heart and cancelling out any such motion in the motions perceived by the master.

25 Claims, 25 Drawing Sheets

U.S. PATENT DOCUMENTS

| | | |
|---|---|---|
| 5,402,801 A | 4/1995 | Taylor |
| 5,458,574 A | 10/1995 | Machold et al. |
| 5,572,999 A | 11/1996 | Funda et al. |
| 5,631,973 A | 5/1997 | Green |
| 5,695,500 A | 12/1997 | Taylor et al. |
| 5,697,939 A | 12/1997 | Kubota et al. |
| 5,738,649 A | 4/1998 | Macoviak |
| 5,762,458 A | 6/1998 | Wang et al. |
| 5,791,908 A | 8/1998 | Gillio |
| 5,792,135 A | 8/1998 | Madhani et al. |
| 5,808,665 A | 9/1998 | Green |
| 5,855,583 A | 1/1999 | Wang et al. |
| 5,871,017 A | 2/1999 | Mayer |
| 5,876,325 A | 3/1999 | Mizuno et al. |
| 5,931,832 A | 8/1999 | Jensen |
| 5,971,976 A | 10/1999 | Wang et al. |
| 6,144,875 A | 11/2000 | Schweikard et al. |
| 6,368,332 B1 | 4/2002 | Salcudean et al. |
| 6,574,492 B1 | 6/2003 | Ben-Haim et al. |
| 6,594,552 B1 * | 7/2003 | Nowlin et al. ............... 700/260 |
| 2003/0158463 A1 * | 8/2003 | Julian et al. ................. 600/104 |

* cited by examiner

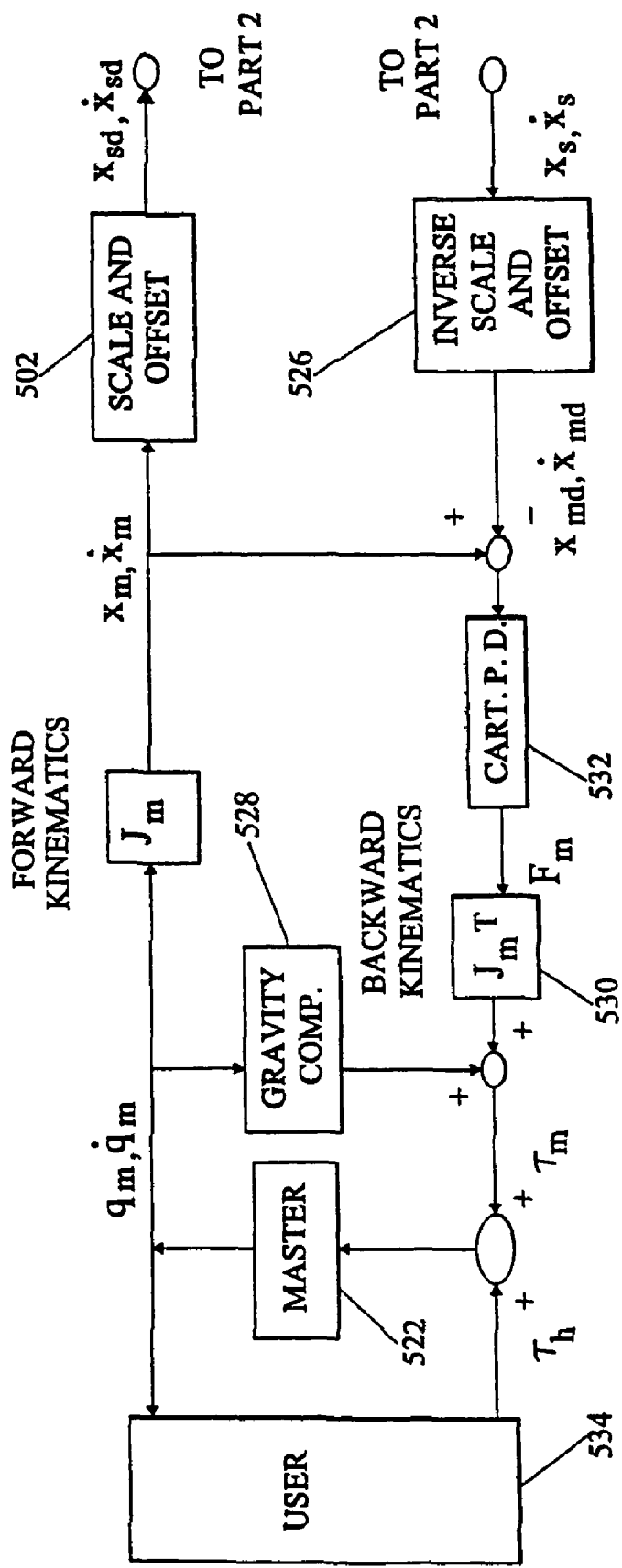
FIG. 22B (PART 1)

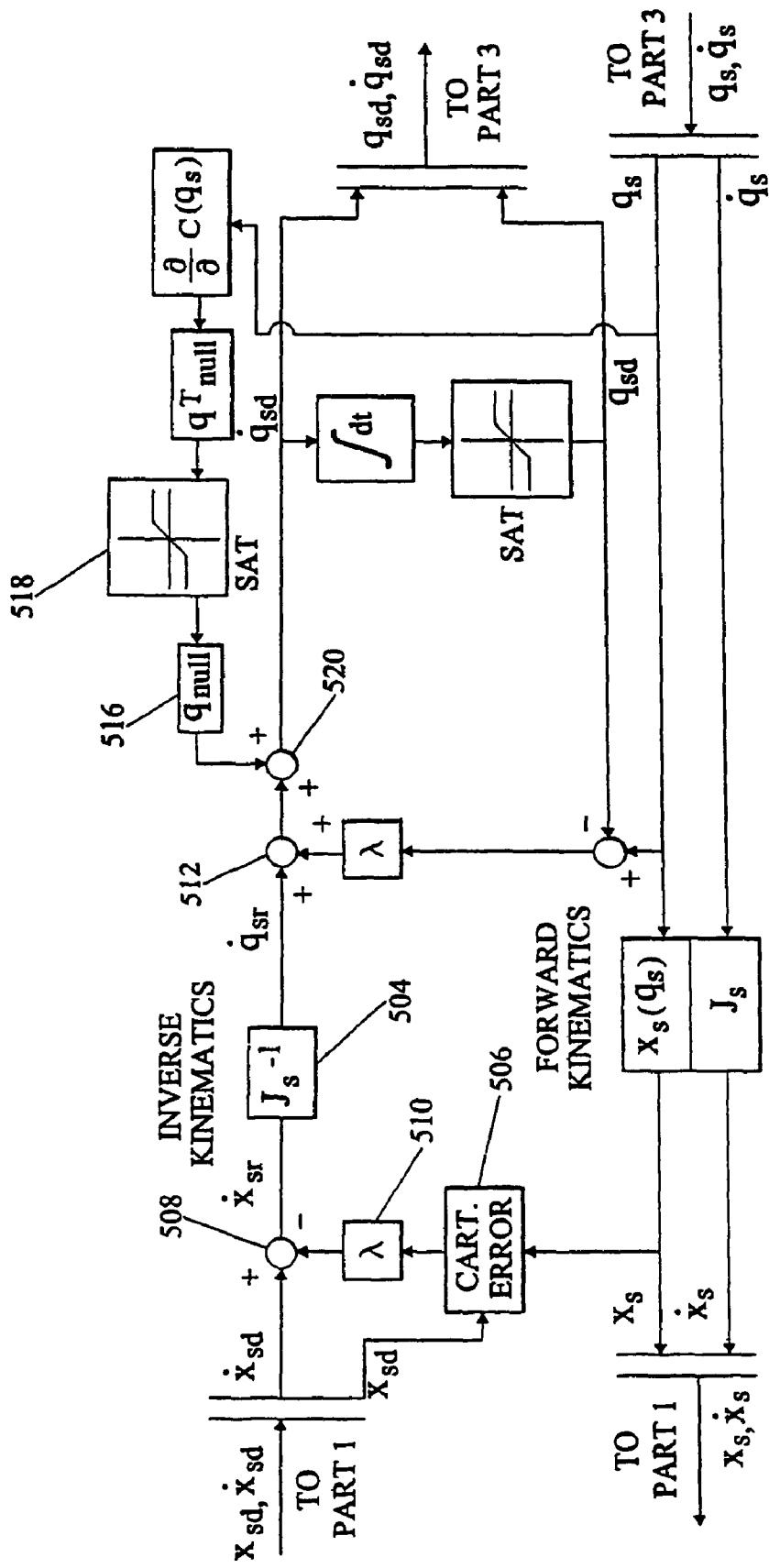
FIG. 22B (PART 2)

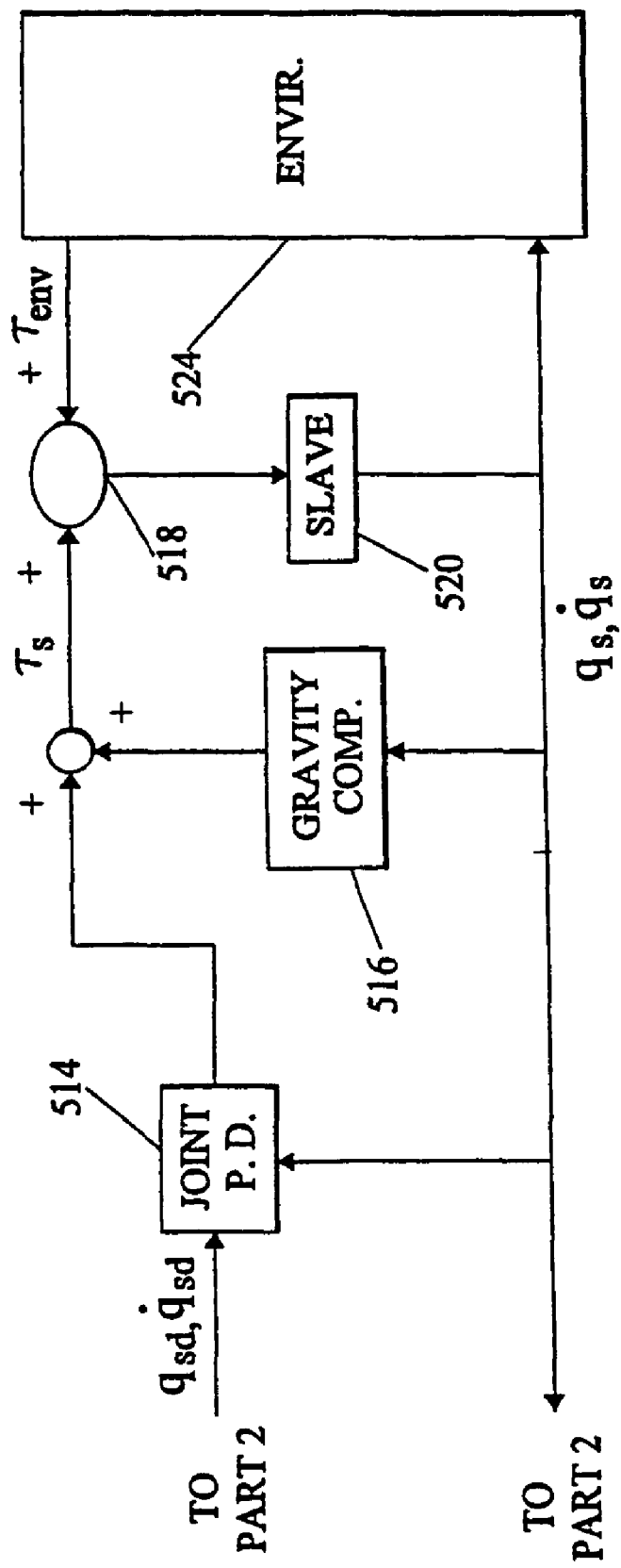
FIG. 22B (PART 3)

ROBOTIC APPARATUS

CROSS-REFERENCES TO RELATED APPLICATIONS

This application is a divisional of, and claims the benefit of priority from U.S. patent application Ser. No. 09/508,871, filed Jul. 17, 2000, which is a 35 U.S.C. §371 United States National Stage application of International Patent Application No. PCT/US98/19508 filed on Sep. 18, 1998 which claims priority to U.S. Provisional application Ser. No. 60/059,395, filed on Sep. 19, 1997, the full disclosures of which are incorporated herein by reference.

The inventions disclosed herein are also somewhat related to inventions by two of the inventors herein (Salisbury and Madhani), described in three U.S. patent applications, all of which are incorporated herein by reference. The three applications were all filed on May 16, 1997, as follows: ARTICULATED SURGICAL INSTRUMENT FOR PERFORMING MINIMALLY INVASIVE SURGERY WITH ENHANCED DEXTERITY AND SENSITIVITY, U.S. Ser. No. 08/857,776, issued Aug. 11, 1998, as U.S. Pat. No. 5,792,135; FORCE-REFLECTING SURGICAL INSTRUMENT AND POSITIONING MECHANISM FOR PERFORMING MINIMALLY INVASIVE SURGERY WITH ENHANCED DEXTERITY AND SENSITIVITY, U.S. Ser. No. 08/858,048; and WRIST MECHANISM FOR SURGICAL INSTRUMENT FOR PERFORMING MINIMALLY INVASIVE SURGERY WITH ENHANCED DEXTERITY AND SENSITIVITY, U.S. Ser. No. 08/857,655, issued Aug. 25, 1998 as U.S. Pat. No. 5,797,900. Each of these, in turn, claimed priority to Provisional application Ser. No. 60/017,981, filed May 20, 1996, which is herein incorporated by reference.

STATEMENT AS TO RIGHTS TO INVENTIONS MADE UNDER FEDERALLY SPONSORED RESEARCH OR DEVELOPMENT

The United States Government has certain rights in this invention pursuant to the DARPA program under Contract No. DAMD194-c-4123.

BACKGROUND OF THE INVENTION

Minimally invasive surgery ("MIS") techniques reduce the amount of extraneous tissue that are damaged during diagnostic or surgical procedures, thereby reducing patient recovery time, discomfort, and deleterious side effects. It is estimated that 7,000,000 surgeries performed each year in the United States can be performed in a minimally invasive manner. However, only about 1,000,000 of the surgeries currently use these techniques, due to limitations in minimally invasive surgical instruments and techniques and the additional training required to master them.

Advances in minimally invasive surgical technology could have a dramatic impact. The average length of a hospital stay for a standard surgery is 8 days, while the average length for the equivalent minimally invasive surgery is 4 days. Thus the complete adoption of minimally invasive techniques could save 24,000,000 hospital days, and billions of dollars annually in hospital residency costs alone. Patient recovery times, patient discomfort, surgical side effects, and time away from work are also reduced with minimally invasive surgery.

The most common form of minimally invasive surgery is endoscopy. A common form of endoscopy is laparoscopy, which is minimally-invasive inspection and surgery inside the abdominal cavity. In standard laparoscopic surgery, a patient's abdomen is insufflated with gas, and cannula sleeves are passed through small (approximately ½ inch {1 cm.}) incisions to provide entry ports for laparoscopic surgical instruments.

The laparoscopic surgical instruments generally include a laparoscope for viewing the surgical field, and working tools, such as clamps, graspers, scissors, staplers, and needle holders. The working tools are similar to those used in conventional (open) surgery, except that the working end of each tool is separated from its handle by an approximately 12-inch long extension tube.

To perform surgical procedures, the surgeon passes instruments through the cannula and manipulates them inside the abdomen by sliding them in and out through the cannula, rotating them in the cannula, levering (i.e., pivoting) the instruments in the abdominal wall and actuating end effectors on the distal end of the instruments. The instruments pivot around centers of rotation approximately defined by the incisions in the muscles of the abdominal wall. The surgeon observes the procedure by a television monitor, which displays the abdominal worksite image provided by the laparoscopic camera.

Similar endoscopic techniques are employed in arthroscopy, retroperitoneoscopy, pelviscopy, nephroscopy, cystoscopy, cisternoscopy, sinoscopy, hysteroscopy and urethroscopy. The common feature of all of these minimally invasive surgical techniques is that they generate an image of a worksite within the human body and pass specially designed surgical instruments through natural orifices or small incisions to the worksite to manipulate human tissues and organs, thus avoiding the collateral trauma caused to surrounding tissues, which would result from creating open surgical access.

There are many disadvantages of current minimally invasive surgical technology. First, the video image of the worksite is typically a two-dimensional video image displayed on an upright monitor somewhere in the operating room. The surgeon is deprived of three-dimensional depth cues and may have difficulty correlating hand movements with the motions of the tools displayed on the video image. Second, the instruments pivot at the point where they penetrate the body wall, causing the tip of the instrument to move in the opposite direction to the surgeon's hand. Third, existing MIS instruments deny the surgeon the flexibility of tool placement found in open surgery. Most laparoscopic tools have rigid shafts and are constrained to approach the worksite from the direction of the small incision. Those that include any articulation have only limited maneuverability. Fourth, the length and construction of many endoscopic instruments reduces the surgeon's ability to feel forces exerted by tissues and organs on the end effector of the tool.

Overcoming these disadvantages and achieving expertise in endoscopic procedures requires extensive practice and constant familiarization with endoscopic tools. However, despite surgeons' adaptation to the limitations of endoscopic surgery, the technique has brought with it an increase in some complications seldom seen in open surgery, such as bowel perforations due to trocar or cautery injuries. Moreover, one of the biggest impediments to the expansion of minimally invasive medical practice remains lack of dexterity of the surgical tools and the difficulty of using the tools.

In a tangentially related area, telesurgery systems are being developed to increase a surgeon's dexterity as well as to allow a surgeon to operate on a patient from a remote location. 'Telesurgery" is a general term for surgical systems where the surgeon indirectly controls surgical instrument movements rather than directly holding and moving the tools. In a system for telesurgery, the surgeon is provided with an image of the patient's body at the remote location. While viewing the three-dimensional image, the surgeon manipulates a master device, which controls the motion of a servomechanism-actuated slave instrument, which performs the surgical procedures on the patient. The surgeon's hands and the master device are positioned relative to the image of the operation site in the same orientation as the slave instrument is positioned relative to the act. During the operation, the slave instrument provides mechanical actuation and control of a variety of surgical instruments, such as tissue graspers, needle drivers, etc., which each perform various functions for the surgeon, i.e., holding or driving a needle, grasping a blood vessel or dissecting tissue.

Such telesurgery systems have been proposed for both open and endoscopic procedures. An overview of the state of the art with respect to telesurgery technology can be found in "Computer Integrated Surgery: Technology and Clinical Applications" (MIT Press, 1996). Prior systems for telesurgery are also described in U.S. Pat. Nos. 5,417,210, 5,402,801, 5,397,323, 5,445,166, 5,279,309 and 5,299,288.

Proposed methods of performing telesurgery using telemanipulators also create many new challenges. One is presenting position, force, and tactile sensations from the surgical instrument back to the surgeon's hands as he/she operates the telesurgery system, such that the surgeon has the same feeling as if manipulating the surgical instruments directly by hand. For example, when the instrument engages a tissue structure, bone, or organ within the patient, the system should be capable of detecting the reaction force against the instrument and transmitting that force to the surgeon. Providing the instrument with force reflection helps reduce the likelihood of accidentally damaging tissue in areas surrounding the operation site. Force reflection enables the surgeon to feel resistance to movements of the instrument when the instrument engages tissue. A system's ability to provide force reflection is limited by factors such as friction within the mechanisms, gravity, the inertia of the surgical instrument and the size of forces exerted on the instrument at the surgical incision. Even when force sensors are used, inertia, friction and compliance between the motors and force sensors decreases the quality of force reflection provided to the surgeon.

Another challenge is that, to enable effective telesurgery, the instrument must be highly responsive and must be able to accurately follow the rapid hand movements that a surgeon may use in performing surgical procedures. To achieve this rapid responsive performance, a surgical servomechanism system must be designed to have an appropriately high servo bandwidth. This requires that the instrument have low inertia. It is also preferable if the system can enhance the dexterity of the surgeon compared to standard endoscopic techniques by providing more degrees-of-freedom ("DOFs") to perform the surgery by means of an easily controlled mechanism. By more DOFs, it is meant more joints of articulation, to provide more flexibility in placing the tool end point.

Another challenge is that to enable minimally invasive surgery, the instrument must be small and compact in order to pass through a small incision. Typically MIS procedures are performed through cannulas ranging from 5 mm. to 12 mm. in diameter.

Surgeons commonly use many different tools (sometimes referred to herein as end-effectors) during the course of an operation, including tissue graspers, needle drivers, scalpels, clamps, scissors, staplers, etc. In some cases, it is necessary for the surgeon to be able to switch, relatively quickly, from one type of end effector to another. It is also beneficial that effectors be interchangeable (even if not very quickly), to reduce the cost of a device, by using the portion of the device that does not include the end effector for more than one task.

However, the mass and configuration of the effector affects the dynamics and kinematics of the entire system. In typical cases, the effector is counter balanced by other elements of the system. Thus, to the extent that effectors are interchangeable, this interchangeability feature should be accomplished without rendering the remainder of the system overly complicated.

What is needed, therefore, is a servomechanical surgical apparatus for holding and manipulating human tissue under control of a teleoperator system.

It would also be desirable to provide a servomechanical surgical apparatus that can provide the surgeon with sensitive feedback of forces exerted on the surgical instrument.

It would further be desirable to provide a servomechanical surgical apparatus that is highly responsive, has a large range of motion and can accurately follow rapid hand motions that a surgeon frequently uses in performing surgical procedures.

It would still further be desirable to provide a servomechanical surgical apparatus that increases the dexterity with which a surgeon can perform endoscopic surgery, such as by providing an easily controlled wrist joint.

It would also be desirable to provide a dexterous surgical apparatus having a wrist with three independent translational degrees-of-freedom, which can provide force feedback with respect to those three degrees of freedom.

It would still further be desirable to provide a surgical instrument having a wrist mechanism for minimally invasive surgery, which is suitable for operation in a telemanipulator mechanism.

It would additionally be desirable to provide a servomechanical surgical apparatus that has easily interchangeable end effectors, the exchange of which does not require significant adjustments to the kinematic and dynamic control of the apparatus, thereby allowing different end effectors to be used on one base unit, either during the same operation, or, at least, during different operations.

To some extent, the inventions discussed in the three patent applications by the present inventors Madhani and Salisbury that are incorporated herein by reference, address these goals. The invention described herein further satisfies these goals.

BRIEF SUMMARY OF THE INVENTION

A preferred embodiment of the invention is a robotic apparatus comprising: seven actuators, M0, M1, M2, M3, M4, M5 and M6; a support; an end effector link having an effector reference point; and a linkage of links and joints between the support and the end effector link reference point. The linkage comprises: three macro joints, coupled to each other in series, one of which joint 0 is coupled directly to the support, the joints operating to provide three macro translation DOFs to the end effector link reference point, which macro DOFs are characterized by a relatively large range of motion; and four additional joints, designated micro joints coupled in series with the three macro joints and coupled to each other in series, one of which micro joints, joint 6 being coupled directly to the end effector link reference point, the four micro joints operating to provide three micro translation DOFs to the end effector link reference point, which micro DOFs are characterized by a relatively small range of motion as compared to the macro DOFs and where the micro DOFs are redundant with the macro DOFs with respect to translation. For each of the actuators, there is a transmission, coupled to the actuator and coupled to at least one of the seven (four micro plus three macro) joints, thereby actuating each of the seven joints.

The actuators are mounted such that during translation of the effector link reference point, the actuators move through no more than two macro DOFs, and such that they move through no micro DOFs. The linkage comprises macro links that are movable only with the macro DOFs, and other, micro links that are movable through both the macro DOFs and the micro DOFs. The micro links each have a relatively low inertia, as compared to the inertia of any one of the macro links.

According to another preferred embodiment, the three macro joints comprise: a joint 0, a rotary joint about an axis A0, coupled to the support and to a joint 0 link; joint 1, a rotary joint, about an axis A1, orthogonal to the axis A0 and coupled to the joint 0 link and to a joint 1 link; and joint 2, a translational joint along an axis A2, spaced from and perpendicular to the axis A1 and coupled to the joint 1 link and to a joint 2 link.

According to yet another preferred embodiment, the four micro joints comprise: joint 3, a rotary joint about an axis A3, that is parallel to the Axis A2, coupled to the joint 2 link and to an elongated hollow shaft link; joint 4, a rotary joint about an axis A4, that is perpendicular to the axis A3, coupled to the hollow shaft link and to an extension link; joint 5, a rotary joint about an axis A5, that is spaced from and parallel to the axis A4, coupled to the extension link and to an effector support link; and joint 6, a rotary joint about an axis A6 that is spaced from and perpendicular to the axis A5, coupled to the effector support link and to the end effector link.

There may also be an eighth actuator M7 and an additional joint, which couples an end effector jaw link to the effector support link, to rotate around an axis A7, which jaw link is operable to move toward and away from the end effector link, thereby effectuating gripping of an object therebetween.

According to still another preferred embodiment, a total of six effector cable tension segments extend from various components of the end effector, through the elongated hollow link.

A preferred embodiment of a micro macro manipulator as described above also includes a controller that controls the manipulator according to an Inverse Jacobian controller, where the gains of the macro freedoms are adjusted to be much larger than the gains of the micro freedoms, on the order of the ratio of the inertias thereof.

According to a related preferred embodiment, the transmission comprises the six cables and a base set of transmission elements, which are each coupled directly to one of the actuators; and a releasable couple, which couples an individual one of the six effector cable tension segments to an individual one of the base set of transmission elements. The base transmission elements may include cable segments.

According to still another preferred embodiment, any one of the embodiments of the invention outlined above may constitute a slave actuator unit. A master actuator unit may be provided, having a master linkage, having: a master reference point, coupled to a master ground support through a plurality of master links and master joints; and a plurality of master actuators, coupled to the master linkage to actuate the master reference point. A controller is coupled to the slave unit actuators, configured to control the slave according to an Inverse Jacobian controller. Another controller is coupled to the master actuators, configured to control the master according to a Jacobian Transpose controller.

The macro freedom gains and the micro freedom gains are preferably chosen such that the inertia of the macro freedoms is suppressed in any forces felt at the master reference point.

According to yet another preferred embodiment, the slave unit linkage is characterized by a number X of DOFs, X being at least seven DOFs and the master unit linkage is characterized by a number Y of DOFs where Y is at least one fewer than X. According to this embodiment, the slave controller can be configured to resolve a redundancy in control due to the difference between the X DOFs of the slave unit and the fewer Y DOFs of the master unit by applying a cost function to a range of possible joint configurations, each of which provide the same location of the end effector link reference point, and minimizing the cost function.

Another preferred embodiment of the invention is a robotic apparatus having a base unit and an effector unit. The base unit has a support, an actuator M0 and a base linkage, connected to the support, and to the effector unit. The base linkage comprises a drivable member D0, drivable by the actuator M0 through a DOF DOF0, such that the effector end of the base linkage is drivable through the DOF0. The base linkage also includes a drivable member D1, movable through the DOF0 with the drivable member D0, and also through another DOF DOF1. An actuator M1, drives the drivable member D1 through the DOF1, such that the effector end of the linkage is drivable through the DOF1. An actuator set, which is drivable with the drivable member D1 through the DOF1, comprises a plurality of K actuators. Each of the plurality K has one terminal thereof fixed relative to the drivable member D1, and one terminal thereof free to move through one DOF relative to the drivable member D1. The base further includes a plurality K of base transmission elements, each of the plurality K coupled with a free terminal of one of the K actuators, and each of the base transmission elements including an effector transmission coupling site. This base, alone, is a preferred embodiment of the invention. It can also be used, in combination with the effector unit, described as follows.

The effector unit has a base end, connected to the base linkage, an end effector and an effector linkage comprising a plurality of links and joints, which effector linkage extends from the base end to the end effector. For each joint, an effector transmission element is connected to a link that is adjacent the joint and that also has a base coupling site distant from the link connection. For each effector transmission element, a transmission clamp connects the effector transmission element to a corresponding base transmission element, thereby coupling the effector transmission element, and thereby its associated link, to a movable terminal of one of the plurality K of actuators.

According to such a preferred embodiment, the end effector has N=K+2 DOFs under action of the plurality K actuators and the two actuators M0 and M1, none of which plurality K actuators are movable through any of the N DOFs other than the DOF0 and DOF1.

The end effector just described may also be used with other types of base supports. A releasable couple between the transmission elements of the base and the effector completes the transmission.

It is also a preferred embodiment of the invention to provide, coupled to the Inverse Jacobian controller and to the Jacobian Transpose controller, an environment position sensor, arranged to generate a signal that corresponds to the translational position of a reference point in an environment in which the slave may reside. The Inverse Jacobian controller further commands the macro freedom actuators and micro freedom actuators to move the effector reference point in concert with the environment reference point. The Jacobian Transpose controller further is configured to command the master to move the master reference point to follow only motion of the effector reference point that does not correspond to motion of the environment reference point. This presents the effect to a user who is in contact with the master reference point that the effector is interacting with an environment that is substantially motionless. Thus, a surgeon engaging the master can use the slave to operate on a beating heart, while perceiving the heart as stationary.

According to yet another preferred embodiment of the invention, at least two base transmission elements of a base, such as is described above, comprise cables and at least two corresponding effector transmission elements comprise cables. An extent of the at least two base transmission elements extend substantially parallel to each other and an extent of the at least two effector transmission elements extend substantially parallel to each other. The extent of each of the at least two effector transmission elements that extends substantially parallel to each other is parallel to and adjacent to the extent of the corresponding of the at least two base transmission elements that extends substantially parallel to each other. The adjacent extents of corresponding effector and base transmission elements can be clamped to each other such that motion of the base transmission elements is transmitted to the effector transmission elements. There can be any number of pairs of cables so clamped to each other.

Yet another preferred embodiment of the invention is simply a couple between an actuator unit and an effector unit of a robotic apparatus. The actuator unit, comprises an actuator that actuates a tension bearing transmission element, comprising a tension segment that is arranged to follow a straight line for a portion of its path [PAS]. The effector unit comprises a movable end effector link, coupled to a tension bearing transmission element, comprising a tension segment that is arranged to follow a straight line for a portion of its path PES, which PES is arranged parallel to the portion PAS. A releasable couple clamps the portion PAS of the actuator unit transmission element to the portion PES of the effector unit transmission element, thereby releasably coupling the actuator to the end effector link. There can be a large number of parallel transmission elements so linked together, for instance at least six.

Still another preferred embodiment of the invention is An actuator set comprising a plurality of actuators, each actuator having a first and a second terminal, the second of which is rotatable about an output axis relative to the first, which second terminal is adapted to engage a transmission element, each of the output axes having a component thereof that is parallel. For each of the actuators, a transmission element is looped around the rotatable terminal, forming two tension segments. For each of the transmission elements there are a pair of low friction circular surfaces, along each of which passes one of the two tension segments. The pair of circular surfaces are centered about an axis that is substantially perpendicular to a component of the output axis of the respective actuator. There is also turnaround located along the path of the transmission element between the points at which it engages each pulley of the pair, such that tension is maintained on the transmission element. The axes of the actuators may be parallel.

Yet another preferred embodiment of the invention is a method of controlling a manipulator, as described above, comprising the steps of: coupling a controller to the manipulator actuators; configuring the controller to control the manipulator according to an Inverse Jacobian controller; commanding the micro freedom actuators M3, M4, M5 and M6 with micro freedom gains; and commanding the macro freedom actuators M0, M1 and M2 with macro freedom gains that are much larger than the micro freedom gains.

The method may further include sizing the macro and micro freedom gains such that the ratio of a representative one of the micro freedom gains to a representative one of the macro freedom gains is on the order of a ratio of a representative one of the micro freedom inertias to a representative one of the macro freedom inertias.

A preferred embodiment of the invention also includes controlling such a manipulator as a slave apparatus, by a master apparatus, including the further step of configuring a Jacobian Transpose controller to command the master to move the master reference point to follow motion of the effector reference point.

A final preferred embodiment of the invention is a method of controlling such a manipulator, when the slave unit linkage is characterized by a number X of DOFs, X being at least seven DOFs and the master unit linkage is characterized by a number Y of DOFs where Y is at least one fewer than X, the method further comprising the step of resolving a redundancy in control due to the difference between the X DOFs of the slave unit and the fewer Y DOFs of the master unit by applying a cost function to a range of possible joint configurations, each of which provide the same location of the end effector link reference point, and minimizing the cost function.

BRIEF DESCRIPTION OF THE DRAWINGS

These and other features, aspects, and advantages of the present invention will become better understood with regard to the following description, appended claims and accompanying drawings, where:

FIG. 22B is a schematic representation in block diagram form showing an Inverse Jacobian position derivative controller for a slave, with a Jacobian transpose position derivative controller for a master, for the control of a slave having X DOFs by a master having Y DOFs, where X is greater than Y, which can also implement a macro-micro control scheme;

DETAILED DESCRIPTION OF THE INVENTION

Mechanism Overview

Figure 1:
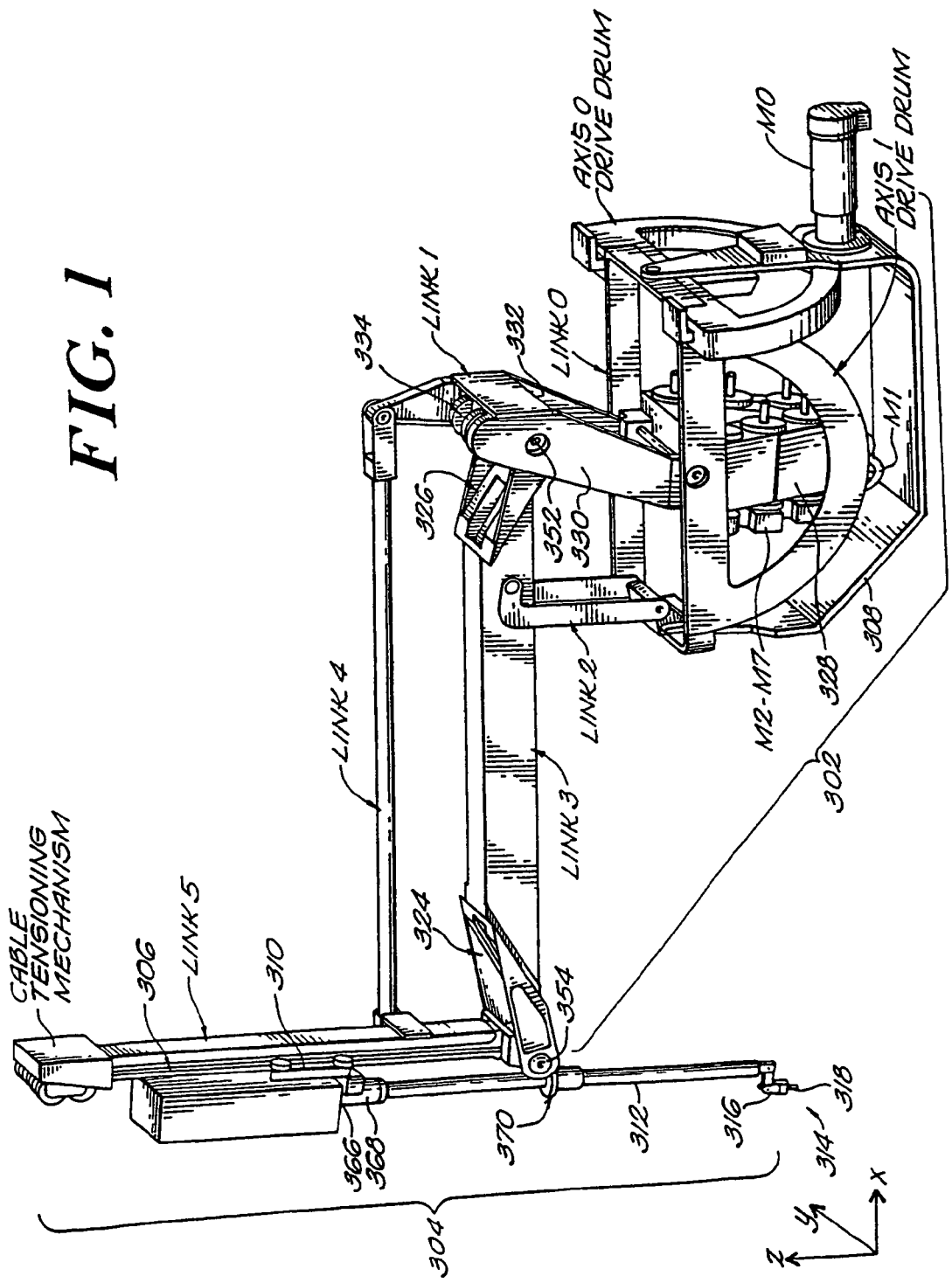
FIG. 1 is a schematic representation in a perspective view of an embodiment of a base positioning unit and wrist unit of the invention.

The following is an overview of the system. More details are provided in subsequent sections. A preferred embodiment of a slave apparatus of the invention is shown in FIG. 1 and consists of two main subsystems, a base unit 302 and a wrist unit 304. The base unit contains all of the actuators M0-M7 for the entire system, the links link 0-link 5 and provides a mechanical interconnect 306 for the wrist unit 304, which wrist is a passive (i.e. contains no actuators) detachable instrument. The following components are referred to in FIG. 1, and the kinematic structure, including axis and link numbers, is defined in the schematic drawing FIG. 2. Eight joints are labeled 0-7. (The links are not necessarily associated with respectively numbered axes.) The system is grounded through a 'U'-shaped stationary base bracket' 308. A spindle link 0, rotates within this base about axis 0. Motor M0 actuates this axis 0 using a cable drive connected to the axis 0 drive drum. Link 1 rotates about axis 1 within the spindle. Link 1 holds motors M1-M7.

Motor M1 drives Link 1 about axis 1 using a cable drive similar to that used for axis 0, connected to the axis 1 drive drum. A difference is that the axis 0 drive drum rotates relative to the axis 0, while the axis 1 drive drum is stationary relative to the axis 1. The other motors, M1-M7, are all mounted within link 1. Remote center kinematics (discussed below) are formed by the links 1-5. Links 1, 3, and 5 are the main structural members, while links 2 and 4 act in tension and compression. Link 5 holds two bearing rails 306 on which a carriage 310 rides. The carriage 310 holds the wrist unit 304, which comprises a mechanical attachment (not shown in FIG. 1), an instrument shaft 312, and an end effector 314 consisting of a wrist 316 and grippers 318, in the embodiment shown.

Remote Center Kinematics

Figure 3:
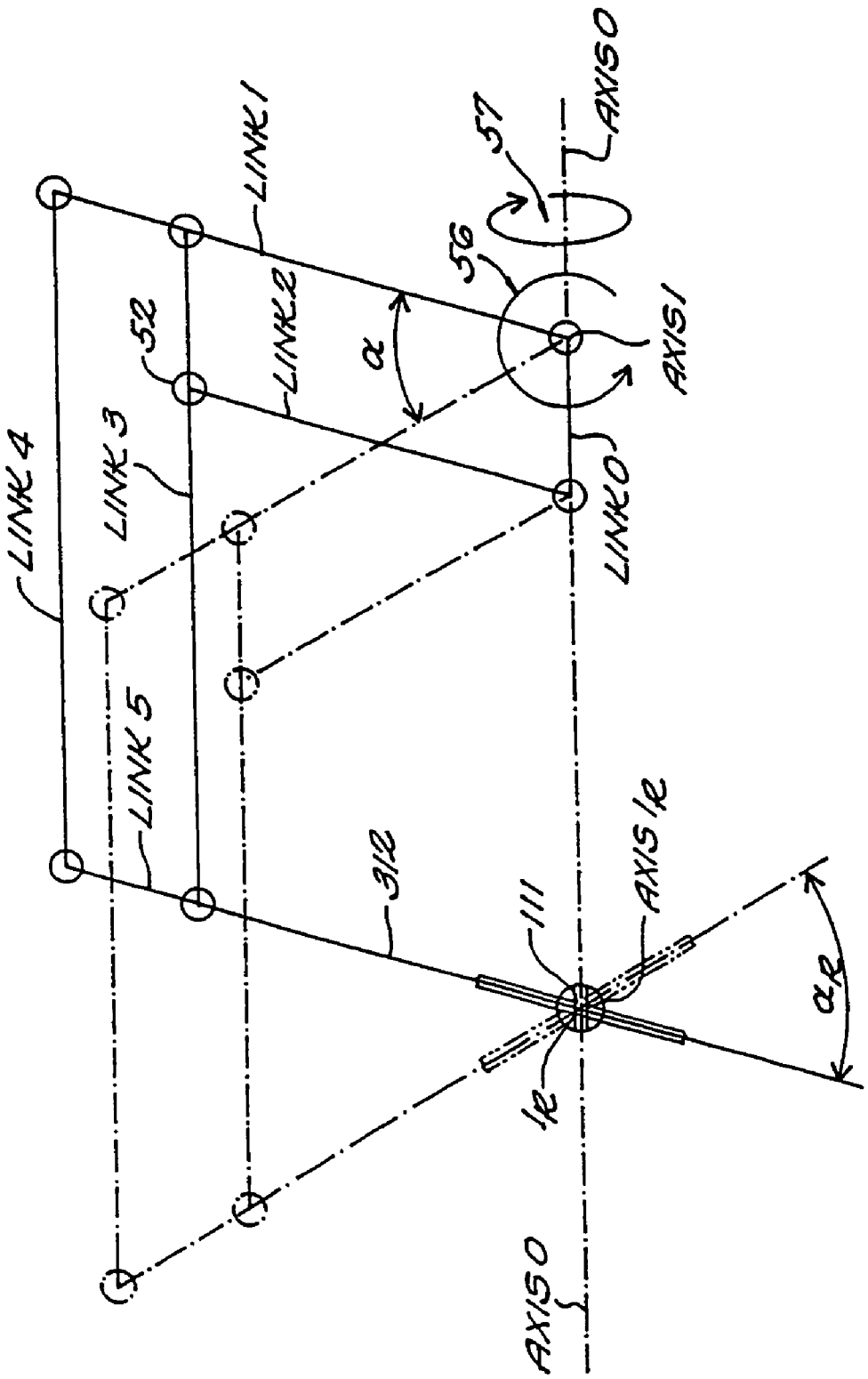
FIG. 3 is a schematic representation in a side view of the kinematics of the embodiment of a base positioning unit and wrist unit of the invention shown in FIG. 1, showing how a remote center is established.

The purpose of the base positioner 302 is to position the wrist unit 304 with two degrees-of-freedom ('DOF") (pitch and yaw) inside the human body, without violating the constraint imposed by the fixed tissue incision point. Combined with a translational degree of freedom along the tool shaft 312, which is part of the wrist unit, this provides three translational DOF positioning (e.g. x,y,z) for the wrist 316 and fingers or jaws 318. These three DOFs are without regard to DOFs provided by actuation of the wrist itself 314 relative to the tool shaft 316. The kinematics that accomplish this are shown in FIG. 3. The double parallelogram linkage shown gives the instrument shaft two rotary DOFs about a remote center point 111. One DOF is rotation about the axis 0, which rotation is into and out of the page, indicated at arrow 57. The other DOF is rotation about axis 1 for the parallelogram and about axis $1_R$ for the tool shaft 312, indicated by the arcs α and $α_R$, respectively, and the arrow 56.

Offsets in the links (from the placement shown in FIG. 3) allow placement of the carriage and link 5 behind the remote center (towards the base) in order to give room for the wrist unit. (See FIG. 9.)

Range of Motion and Workspace

Figure 4:
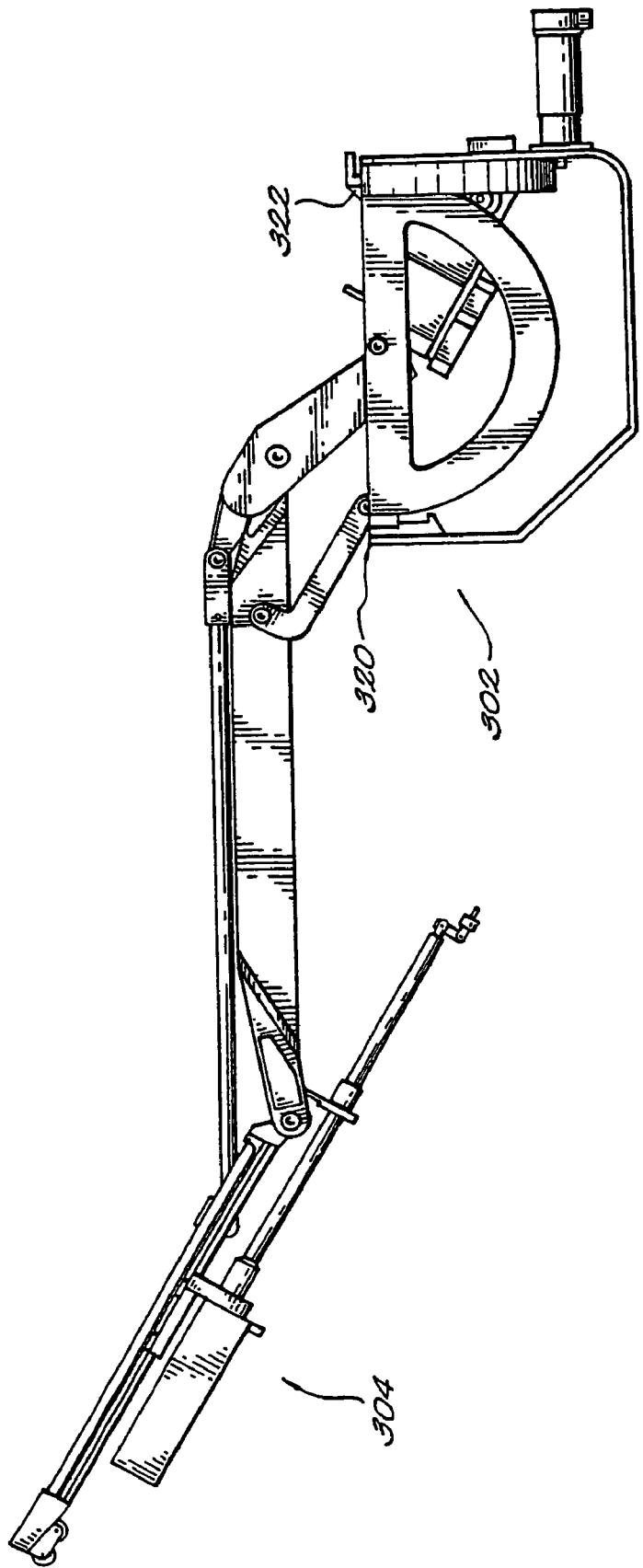
FIG. 4 is a schematic representation in a side view of the embodiment of the base positioning unit and wrist unit of the invention shown in FIG. 1, showing its range of motion pitching forward 60° around axis 1.

The embodiment of the invention shown in FIG. 1 can pitch forwards and backwards about axis 1 by ±60 degrees, as shown in FIGS. 4 (forward) and 5 (backward) respectively. As discussed below, the motors are placed such that they form a "V" shape, which straddles link 3, facilitating a larger rearward pitch angle than would be possible with another configuration, while still allowing the weight of the motors to be placed where it can counterbalance the system. It can also yaw about axis 0 by ±80 degrees. Soft stops 320, 322 made from aluminum covered with soft foam rubber in these two main base axes provides safety.

Figure 6:
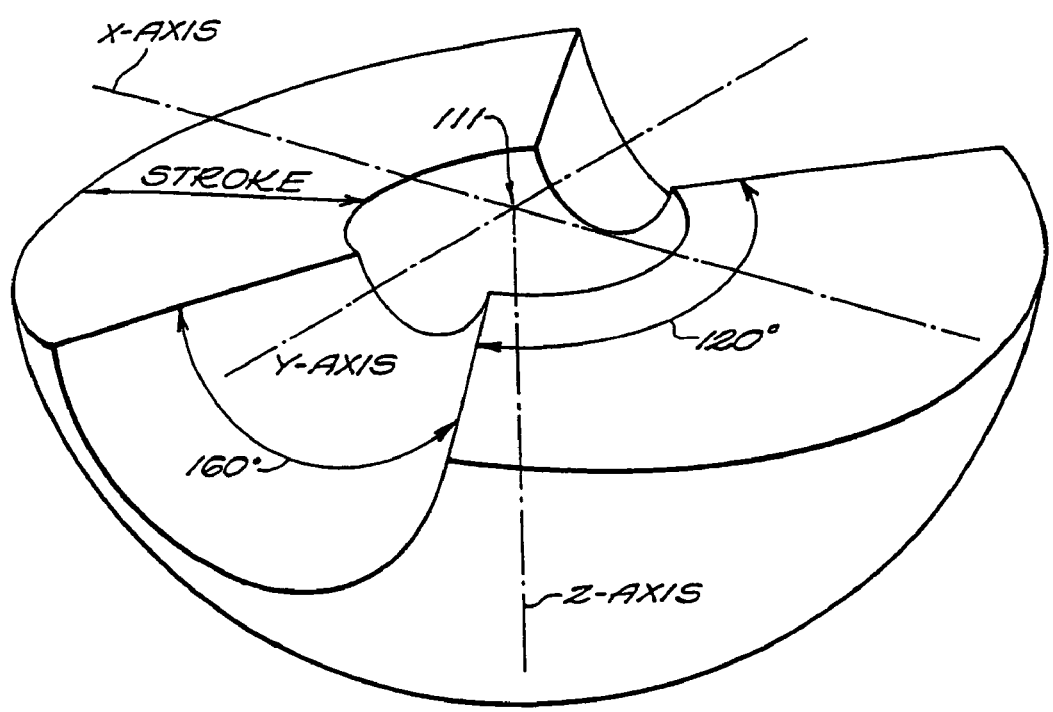
FIG. 6 is a schematic representation showing the workspace of the embodiment of the invention shown in FIG. 1.

The overall workspace is portion of a hemisphere with a central, small spherical portion and two conical portions removed, as shown in FIG. 6. The flat surfaces are inclined with respect to each other (in the instance shown at 160°) and they extend 120° between their straight edges. The distance between the spherical surfaces is defined as the "stroke". The location of the truncating spherical surfaces depends on the length of the instrument 312. For example, if the instrument shaft 312 is shorter, access can be had nearer to the remote center 111. The volume of the workspace is generated by rotating the flat surface shown around the y axis (as shown in FIG. 6) through 160°. A typical embodiment of the invention has a stroke along axis 2 of 20 cm (8 in) (with the illustrated type of the wrist unit), and a total carriage travel of 25.4 an (10 in). The area near the remote center 111 cannot be effectively used however with the wrist 314 shown in FIG. 1, because the manipulator is singular there. The illustrated wrist unit uses a 38 cm (15 in) instrument shaft, which can operate from 3.8 cm (1.5 in) to 24 cm (9.5 in) from the remote center. Other wrists can, however, access this area near to the remote center, if desired.

Structure

A preferred embodiment of the structure should be relatively rigid. For example, a typical link 3 is two in (5 cm) aluminum square box tubing machined to 0.050 in (0.13 cm) wall thickness. The pivot forks 324, 326, at the end of link 3 are welded, to minimize flexing that might be found in bolted connections. This link 3 beam is 23 in (58.4 cm) long with pivots connecting it to links 1 and 2 at a distance of 5.5 in (14 cm) apart.

Link 5 is 1 in×1.5 in (2.54 an×3.8 cm) aluminum square tubing machined to 0.050 (0.13 cm) in wall thickness.

Figure 7A:
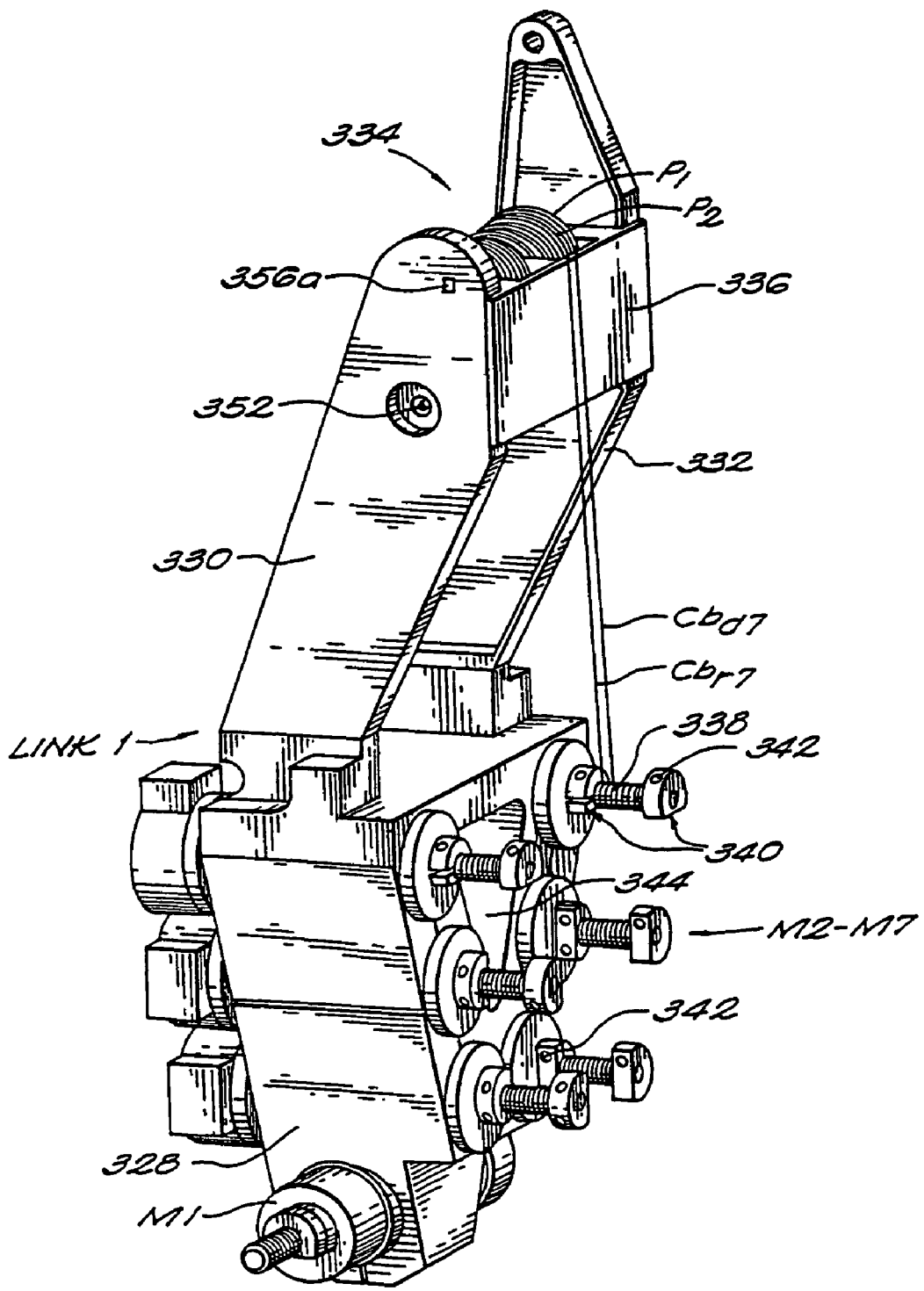
FIG. 7A is a schematic representation in a perspective view of link 1, the motor block, of a preferred embodiment of the base unit of the invention.

As shown in FIG. 7A, link 1 includes a single "V" shaped aluminum block 328, which houses the seven motors M1-M7, with two aluminum uprights 330, 332, bolted to it. The cable idler pulleys 334, shown in FIG. 1, are mounted to a plate 336 that braces the two uprights 330, 332, across their backs to add structural stiffness. The top of the "V", on the face that is not shown in FIG. 7A, is open, to allow a portion of link 3 to fit between the arms of the "V" when the positioning device is in its most rearward configuration. The motors are in a 'V' configuration which fit around link 3 when the system is rotated rearwards.

The stiffness of a representative base structure 302 has been determined by measuring the force required to deflect the end of link 3 by ⅛ in. (0.32 cm.) with the base held fixed (i.e., with no rotation about axes 0 and 1). It was difficult to measure any deflection in the x direction. Because of the small distances over which forces could be applied, accuracy of these values is only about 20%.

$$k_{BY} \cong 5500 \text{ N/m}$$

$$k_{BZ} \cong 12{,}000 \text{ N/m} \tag{1}$$

Humans cannot distinguish a stiffness of 25,000 N/m from infinite rigidity, so 25,000 N/m is ideally the stiffness one might hope to achieve for the overall system, including structural stiffness and servo stiffness of the slave and master. However, practically, a total stiffness on the order of 2,000 N/m would be adequate.

Base Actuators

The base axes of a typical embodiment of the slave device of the invention are powered by motors M0 and M1. Suitable motors are Maxon brand brushed D.C. servomotors (RE035-071-034) with 4.8:1 planetary gearheads. (As used herein, the freedoms of the system are sometimes referred to as 'axes' and sometimes as 'joint.' The terms are generally interchangeable, as used herein.) Additional cable and drum reduction adds approximately 29× reduction to give a total reduction of 137.92:1 for joint 0 and 137.41:1 for joint 1. (The slight difference is caused by manufacturing tolerance.)

It is important that the servo response of the base axes 0 and 1 not be underdamped, which can arise due to a lack of encoder resolution and insufficient speed reduction. A preferred embodiment of the invention was designed such that the base actuator rotor inertias were roughly matched to the output load inertia. That is:

$$R \cong \sqrt{\frac{I_{axis0}}{I_{rotor}}} \cdot \tag{2}$$

The inertia about axis 0 varies as axis 1 is moved through its workspace, so it is impossible to match these inertias in all configurations. Using a ProE (Parametric Technology Corporation, Waltham, Mass.) model of the system, the inertia of the system was found about joint 0 when link 5 is vertical (aligned with the z axis), not including motor inertia, to be 0.183 kgm². When the system is pitched rearward by 60°, the inertia is 0.051 kgm². The motor rotor inertia is 6.96×10⁻⁶ kgm². Using these two values, the reductions required to match the link and rotor inertias at these two configurations are:

$$R = \sqrt{\frac{0.183}{6.96 \times 10^{-6}}} = 162 \tag{3}$$

$$R = \sqrt{\frac{0.051}{6.96 \times 10^{-6}}} = 86$$

Wrist Actuators

FIG. 7A shows link 1, which houses motors M1-M7. The end effector actuators are all placed within link 1. The same Maxon RE-035-071-034 brushed D.C. motors with Canon brand TR36 laser encoders were used. These encoders have 14400 counts per revolution (after quadrature).

Each of the six motors M2-M7 that drive the wrist unit axes is mounted with a threaded drive capstan e.g. 338. The capstan has a flexure clamp manufactured into it to clamp it to the motor shaft. Flats 340 and screws 342 at each end of the clamp allow the cable to be terminated on the pinion at each end. The cable is then wound towards the center of the pinion from each end in opposite directions and comes off of the pinion at essentially the same location along the length of the pinion. In this way, slippage on the pinion, is impossible, and the extra length required to maintain frictional wraps on the pinion is eliminated. The cable used on these axes is 0.024 in. (0.06 cm.) diameter 7×19 construction, stainless-steel cable (Sava Industries, Riverdale, N.J.).

Threading the pinions prevents the cable from rubbing on itself as it travels over the capstans. Also, the threads are semicircular in cross-section so that the cable deforms minimally as it rolls onto and off of the capstans. This is again to minimize friction generated within the cable itself.

The motors M2-M7 are placed parallel to one another. This is very convenient, as discussed below, and allows all the drive cables to emanate from the rear of link 1. This works very well with the base cabling scheme, which will be described below.

Figure 8:
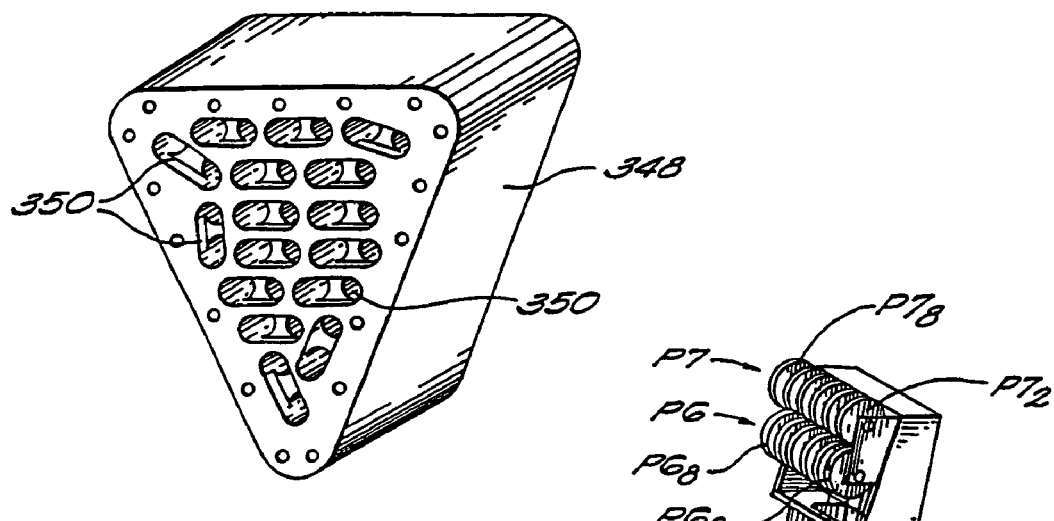
FIG. 8 is a schematic representation in a perspective view of the weight that is housed in the motor block, of a preferred embodiment of the base unit of the invention.

The motors M1-M7 nearly gravitationally counterbalance the slave apparatus for a typical wrist unit 304. To complete and tune the counterbalancing, an additional copper weight (in this case, of 0.95 kg (2.1 lbs)) is placed inside the opening 344 in link 1. The weight can be moved forwards and backwards (generally along the x axis) for tuning. Further, it can be changed to another weight. The weight 346, shown in FIG. 8, incorporates water cooling passages 350 to cool the motor block 320 in link 1. Since the motor block is a single piece of aluminum and covers the entire length of the motors, it provides a good heat sink, and can be cooled using the copper counterweight. The copper weight 350 is removable. If the wrist unit 304 is changed, the counterweight 350 can also be easily changed to another weight that matches the mass of the replacement wrist.

The Maxon motors use a rotor, which consists of a wire basket set in epoxy. While this gives a low mechanical inertia, it also gives a low thermal inertia, making the motors prone to overheating. By water cooling the motors, a factor of four improvement in the thermal power dissipation can be achieved. At stall, this corresponds purely to $I^2R$ losses in the rotor and therefore gives a factor of two improvement in maximum continuous torque output.

Base Cabling

Figure 9:
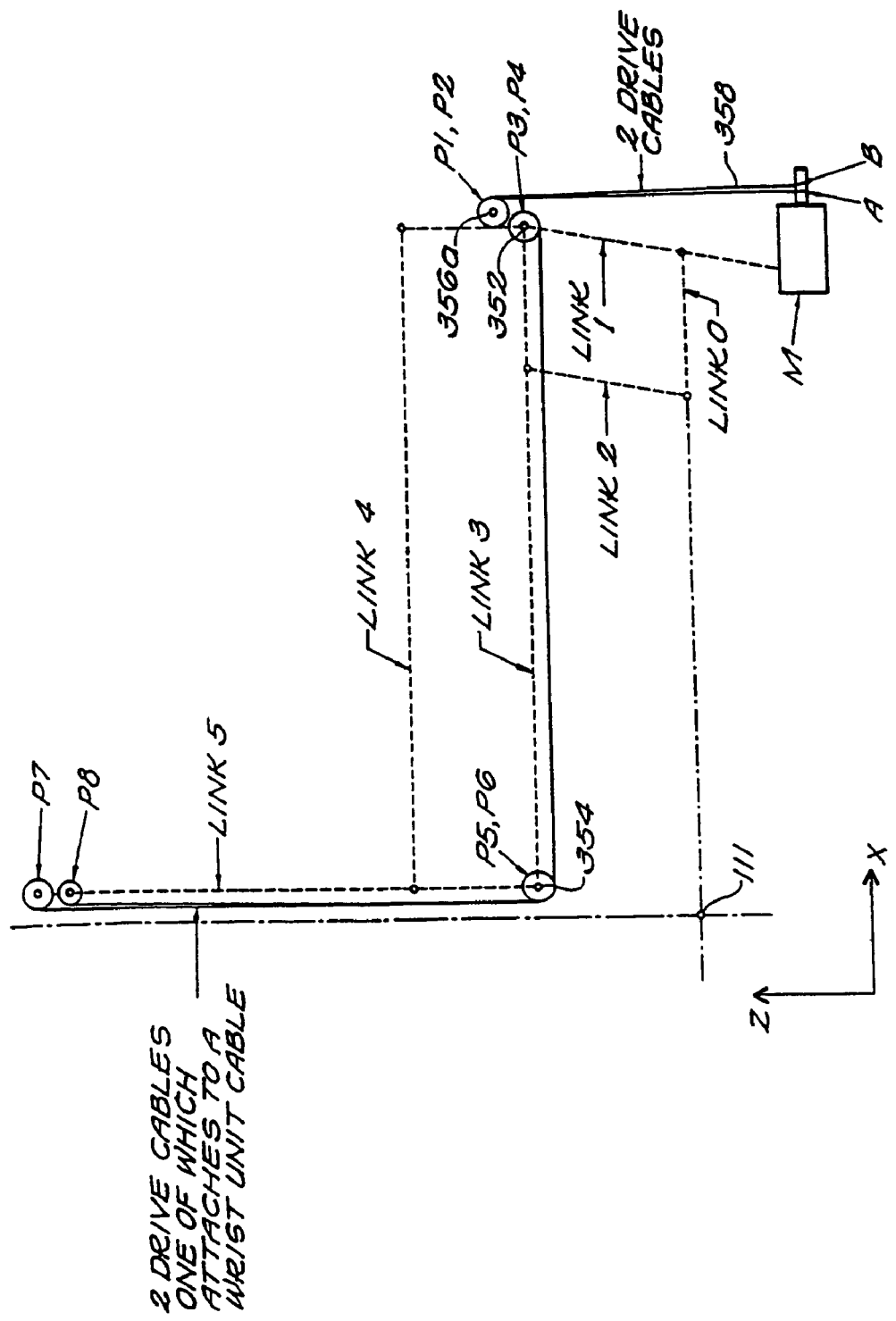
FIG. 9 is a schematic representation in a side view of the embodiment of the base positioning unit and wrist unit of the invention shown in FIG. 1, showing the cabling for the base unit.

The cabling for each of the six motors M2-M7 lies roughly parallel to each other along links 1, 3 and 5. Each of these motors drives a single cable loop 358. FIG. 9 shows how this works for a representative motor M, that is fixed to link 1. The solid lines represent mechanical cables and the dashed lines represent the structural links. The loop begins by anchoring on the motor pinion at point A. The cable continues upwards, passing over the pulley P1 and under pulley P3. It continues along the link 3 along axis x and passes under pulley P5, along link 5, over pulley P7, and is brought leftward along axis x around pulley P8. It then returns around other pulleys that lie next to the pulleys it originally passed around, pulleys P6, P4, P2, respectively and finally terminating on the motor pinion at point B. The latter identified pulleys P6, P4, and P2, are not strictly visible in FIG. 9, being located behind their mates, along the y axis. Pulleys P3 and P4 lie along a shaft 352, which forms the pivot between links 1 and 3, and pulleys P5 and P6 lie on the shaft 354, which forms the pivot between links 3 and 5. The shafts of pulleys P7 and P8 are fixed relative to each other but can translate together along link 5 in order to tension the cable loop. Pulleys P1 and P2 ride on a shaft 356a, which is fixed to link 1. Finally, the motor M is also fixed to link 1. An important feature of this cabling scheme is that as the system pitches forward and backward about axis 1, there is no length change in this cable loop and no coupling between this pitching motion and the motor rotation.

As shown schematically in FIGS. 7A, the motors M2-M7 are arranged with their axes substantially parallel. The route between these parallel motor shafts to the idler pulleys 334 is shown from an end view in FIG. 7B. Each motor is associated with a single cable loop, which has two tension elements, $Cb_{dn}$, and $Cb_{rn}$, where the subscript d indicates that the cable is the drive portion that is connected to an associated wrist cable (see FIG. 13) and then most closely encounters pulley P7, and the subscript r indicates that the cable is the return portion that most closely encounters pulley P8, and is not connected to an associated wrist cable. The subscripts n (running from 2 to 7) correspond to the motor with which the cable is associated. (Only one cable pair is shown.)

Figure 7B:
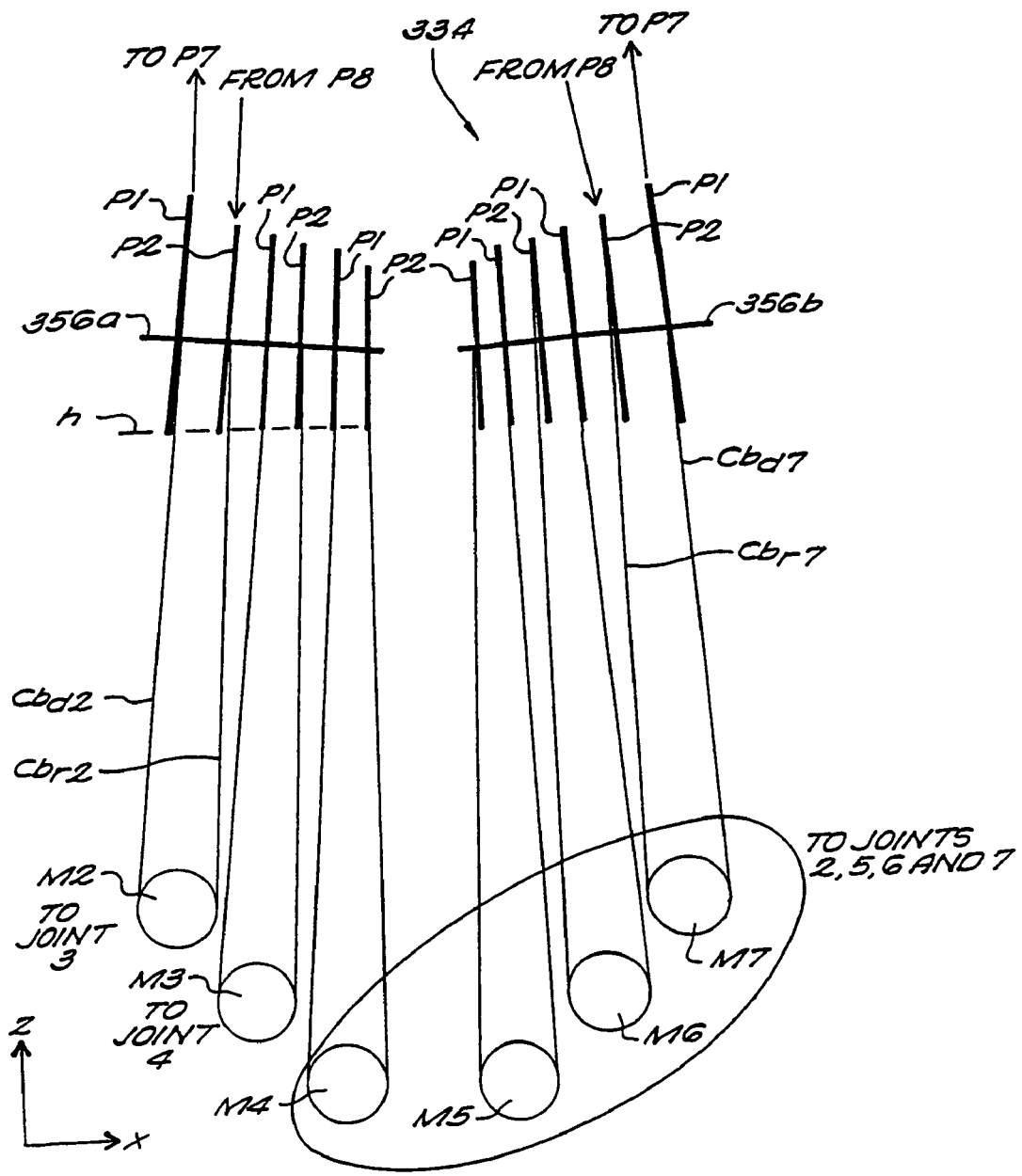
FIG. 7B is a schematic representation in an end view of the motors of an embodiment of the invention that actuate the wrist DOFs, showing the routing of the cables from the motors to adjacent pulleys.

As shown in FIG. 7B, the motors are spread out along the x and z axes such that the cables associated with each can each pass over a corresponding pulley P1 for the drive tension elements and P2 for the return tension elements. There is one P1 pulley for each motor, and one P2 pulley for each motor. The motors are grouped symmetrically in sets of three motors, with the six pulleys for each set of three motors being carried on a single shaft 356a for the motors M2-M4; and 356b for the remaining motors M5-M7.

Figure 7C:
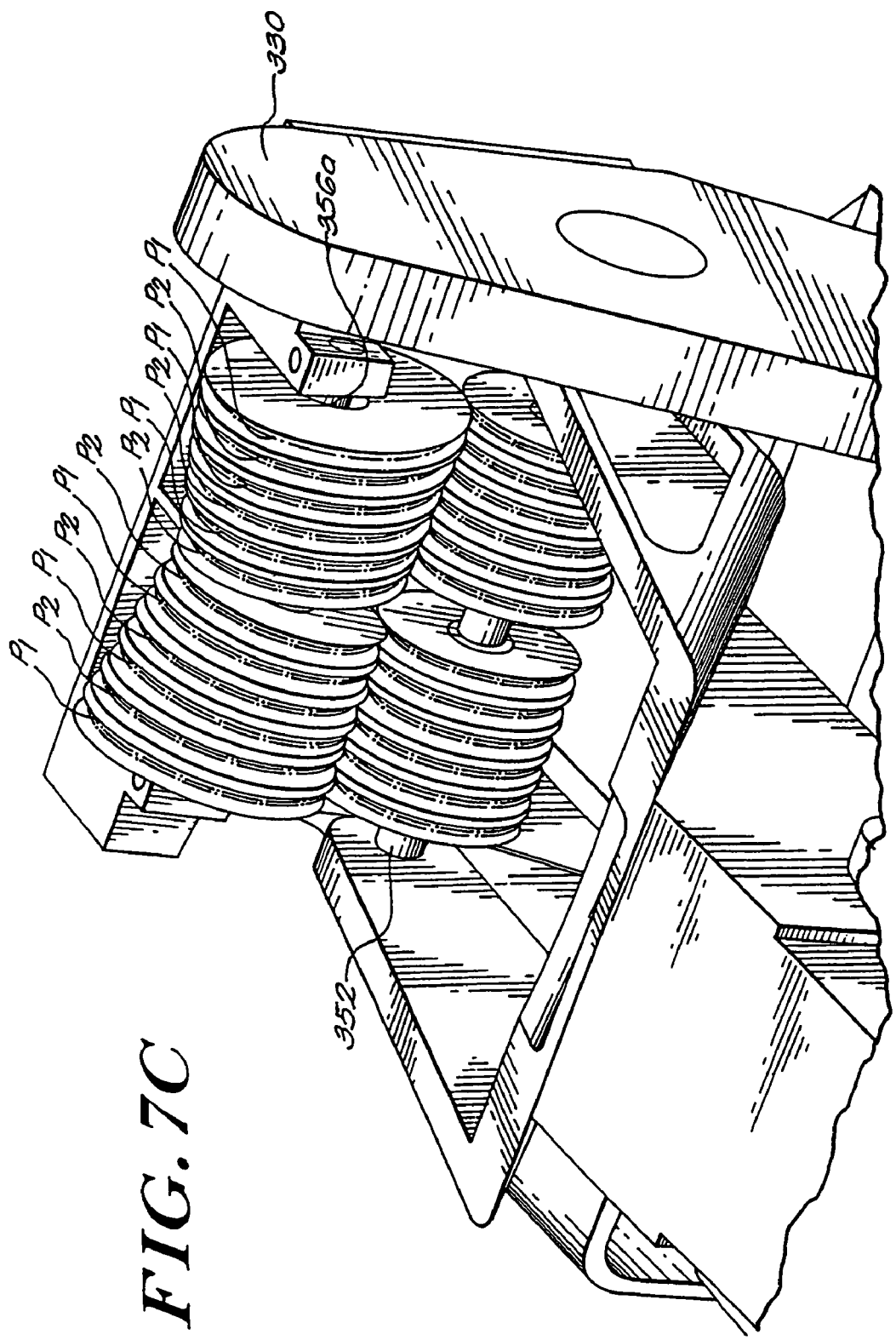
FIG. 7C is a schematic representation in a perspective view, of the graduated pulleys shown in FIG. 7B, generally from the opposite end.

The pulley shafts 356a and 356b are each inclined relative to the x axis, such that the bottoms of all of the pulleys carried by each lie along a horizontal line (indicated by the dashed line h for the shaft 356a). As shown also in FIG. 7C, the pulleys P1 and P2 are of graduated sizes, such that for each shaft 356a and 356b, the P1 pulley on the outside (farthest from each other) has the largest diameter, and the P2 pulley on the inside (nearest to each other) has the smallest diameter, and that all of the intermediate pulleys have intermediate diameters. The inclining of the shafts 356a, (and the graduation of the pulley diameters) is to minimize any angle of incidence between the cables and their respective pulleys. This is to reduce friction therebetween. The goal is to have the cables approaching the pulleys substantially in the plane that is defined by the pulley, at the pulley's middle.

To drive the wrist unit, a direct attachment is made between one side of the cable loop 358 and a cable of the wrist unit, between pulleys P5 and P7. This is further described below, after first describing the carriage and wrist unit.

Carriage

Figure 10:
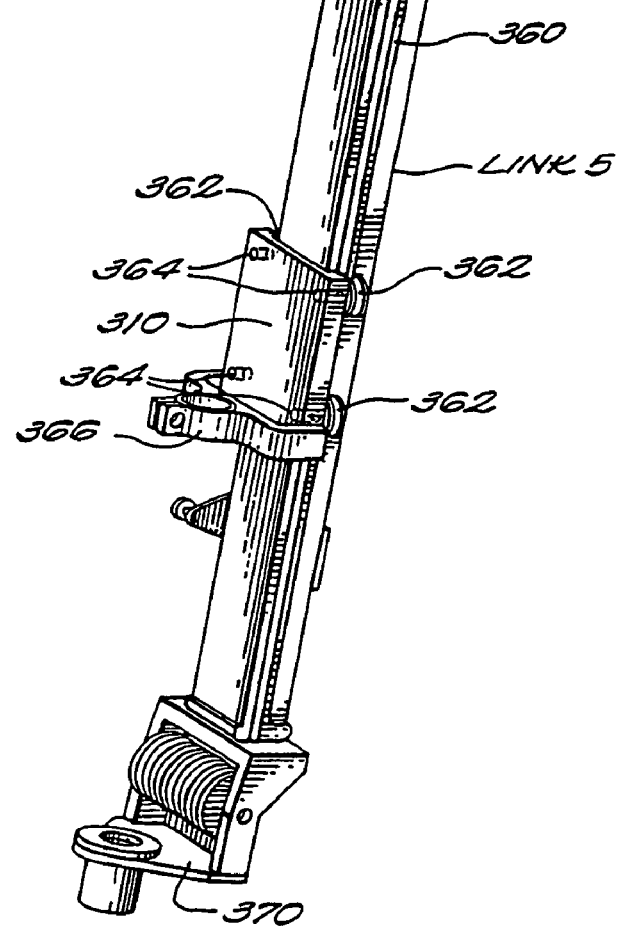
FIG. 10 is a schematic representation in a perspective view of the embodiment of the link 5 of the base positioning unit and the carriage that rides thereon to connect with the wrist unit of the invention shown in FIG. 1.

The carriage 310 for a typical embodiment of the invention, is shown in FIG. 10. The translational joint 2, along axis 2 is effected by translation of the carriage along rails, relative to link 5. The carriage runs on two 4 no stainless steel rails, each mounted in square slots machined into a side of link 5 as bearing ways. Four roller bearings 362, mounted on studs 364, ride on the steel rails 360. Two of the four studs are eccentric so that the bearings may be preloaded against the steel rails. The bearings themselves are shielded, so that dirt and dust do not interfere with rolling of the balls within them, and lubricant is retained. The curvature between the bearing outer races matches the rails to reduce contact stresses. Each of the four bearings 362 has a dynamic load capacity of 269 lbs. The aluminum tubing that comprises link 5 (the carriage beam) is machined from 1×1.5×⅛ in. (2.54×3.8×1.32 cm.) wall aluminum extrusion and is exceedingly stiff in torsion and in bending.

Figure 5:
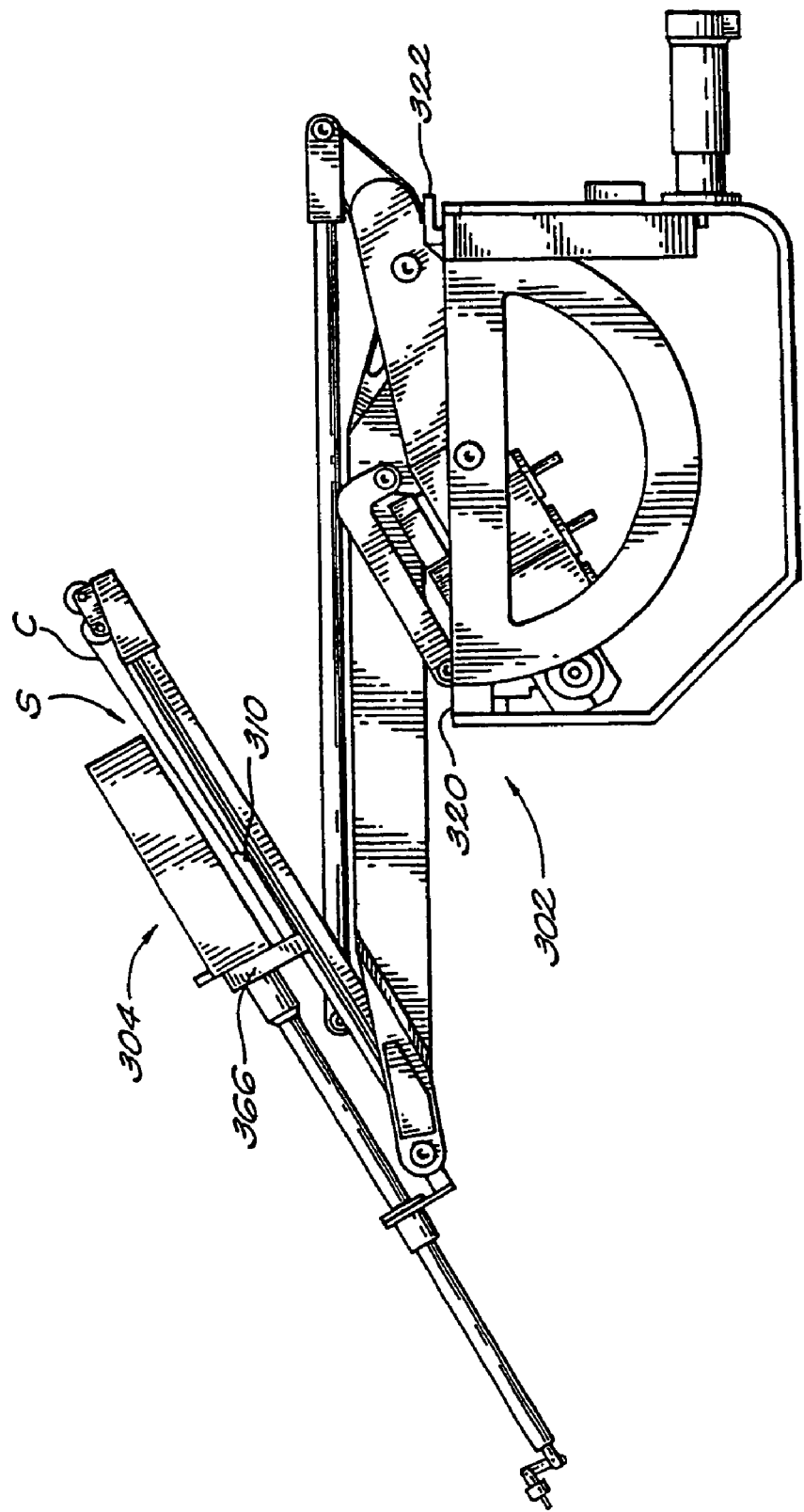
FIG. 5 is a schematic representation in a side view of the embodiment of the base positioning unit and wrist unit of the invention shown in FIG. 1, showing its range of motion pitching backward 60° around axis 1.

A flexure clamp 366 holds the body 368 of the wrist unit 304 to the carriage. Cables run parallel to each other through a space S between the clamp 366 and the carriage 310, as shown in FIG. 5. (Only a single cable is shown in FIG. 5.) All cables lie substantially in the same plane. Finally, the carriage beam link 5 has a support 370 at its bottom to support the slender wrist shaft 312. The support 370 incorporates a Teflon bushing to reduce friction.

Wrist Unit

Figure 11:
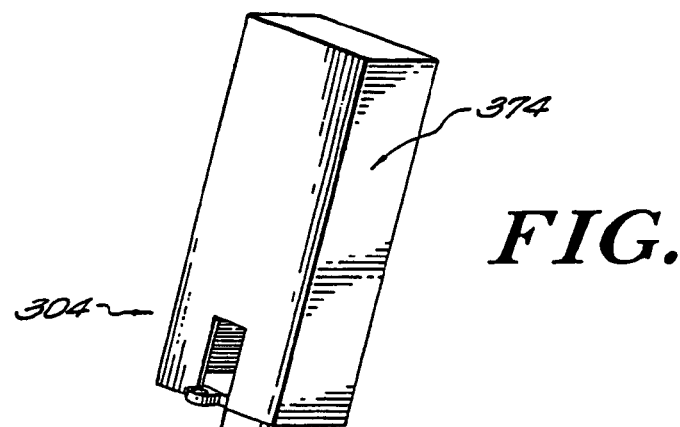
FIG. 11 is a schematic representation in a perspective view of the embodiment of the wrist unit of the invention shown in FIG. 1.
Figure 13:
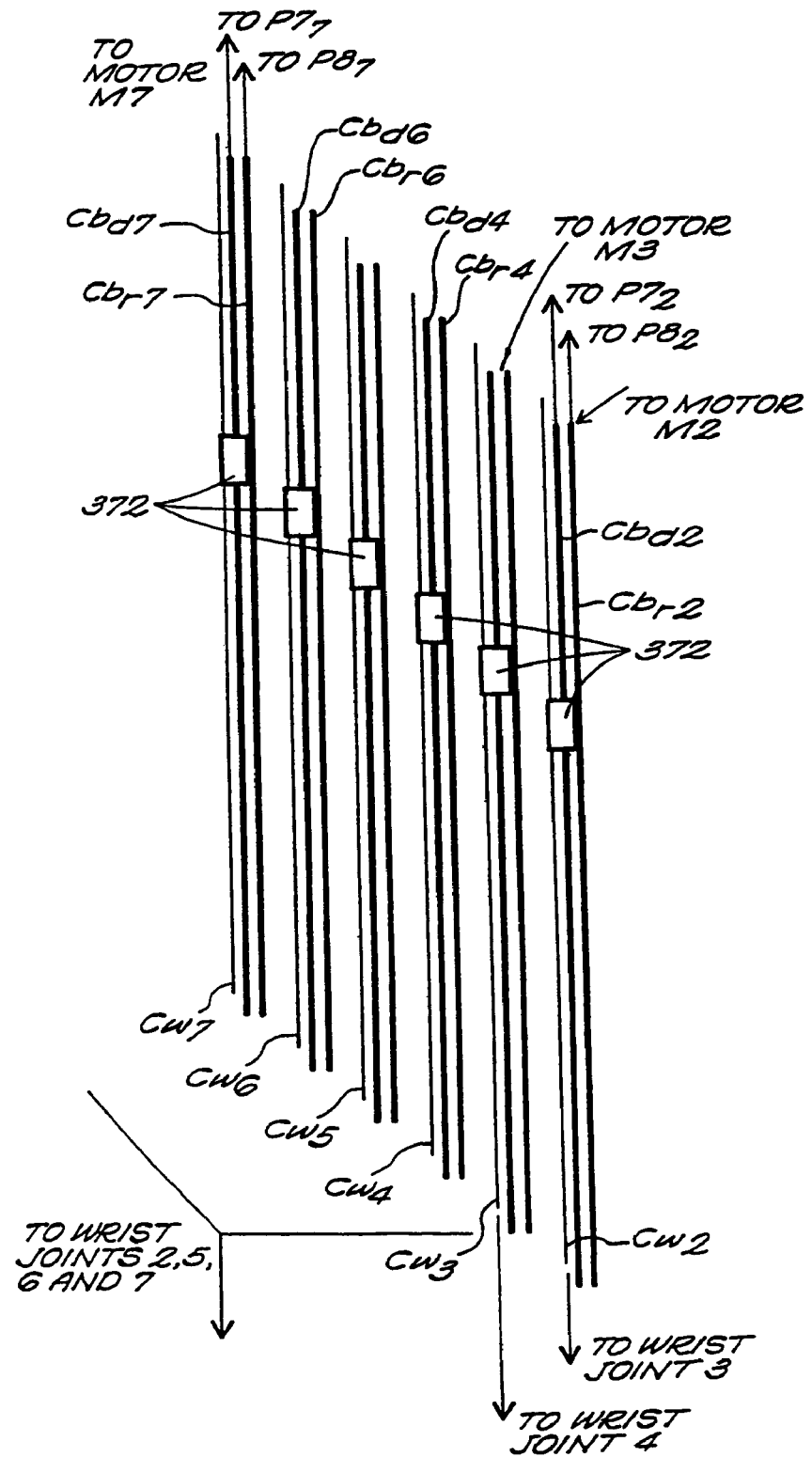
FIG. 13 is a schematic representation showing a preferred embodiment of the interface between the six cables that actuate the wrist and twelve of the cables that emanate from the motors.
Figure 19:
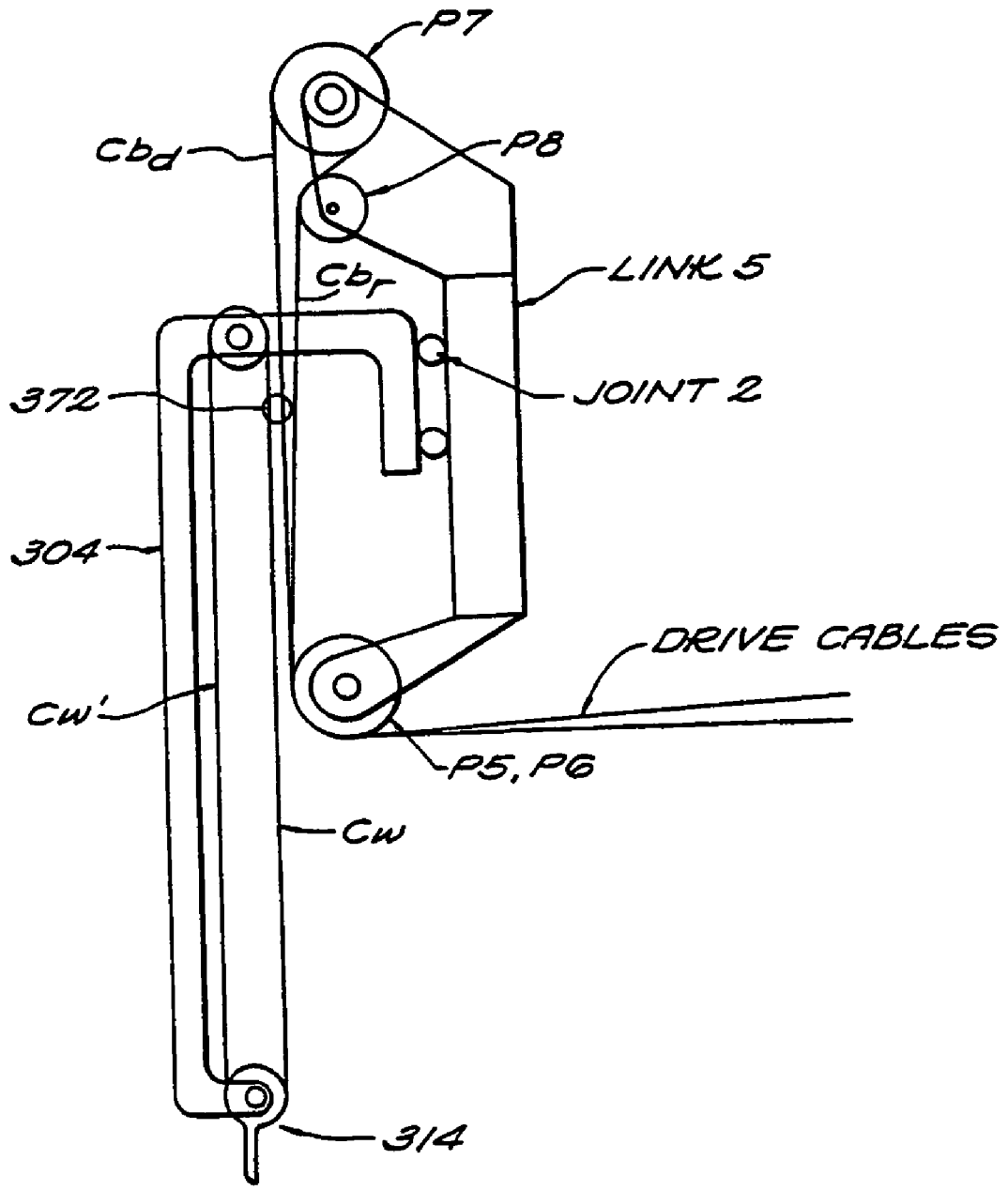
FIG. 19 is a schematic representation showing a side view of a portion of the base unit and the wrist unit of a preferred embodiment of the invention, showing the connection between a wrist cable and its corresponding base drive cable.

The wrist unit 304 is shown separately in FIG. 11. It is a separate assembly that can be detached from the base unit 302. The cables, $Cw_2, CW_3, \ldots, CW_7$, which drive the wrist, are shown schematically in FIG. 13 and form closed pretensioned loops within the wrist unit 304. As shown in FIGS. 13 and 19, the cables are mechanically attached to the respective base unit cables $Cb_{d2}$-$Cb_{d7}$, when the wrist unit 304 is mounted onto the base unit 302. This attachment may be made using screw clamps 372. Using screw clamps, it takes several minutes to make the attachment. However, a quick-release capability is also desirable, and hardware that is capable of such quick-release is contemplated as part of the invention.

Wrist Kinematics

Figure 12:
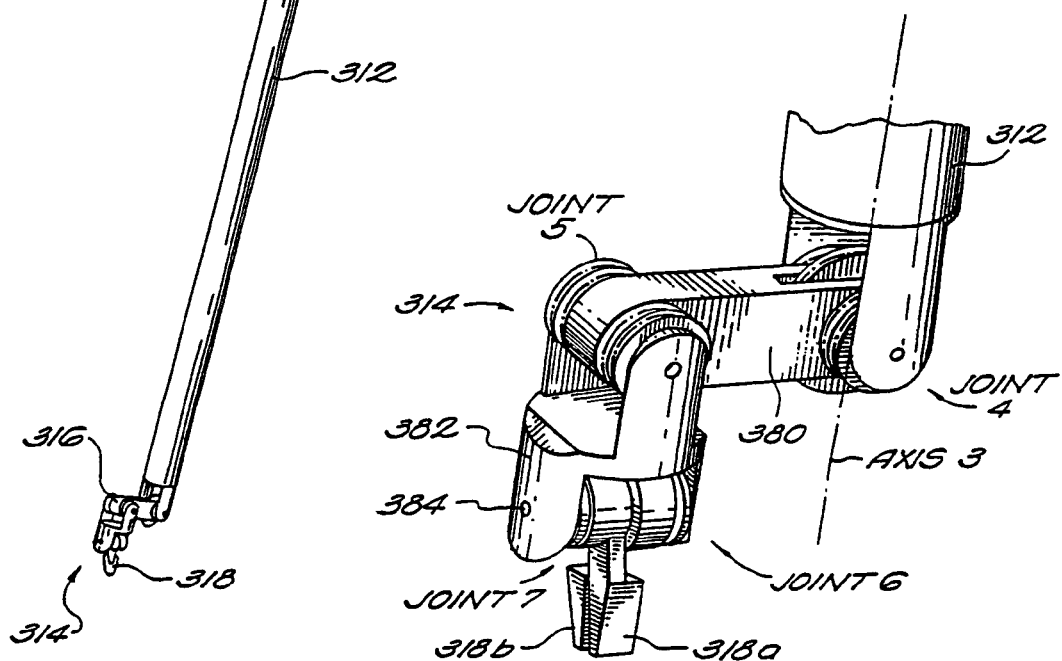
FIG. 12 is a schematic representation in a perspective view of a five joint wrist of the embodiment of the wrist unit of the invention shown in FIG. 1.

FIG. 12 shows a five joint (counting rotation around axis 3) wrist that enables the use of macro-micro control (described below) with the base unit 302, for 3 independent translational DOF of a reference point on the end effector, e.g. the tip of finger 318a. It is possible to use a wrist unit having fewer or greater than five joints with the base unit 302 if desired. (For instance, the four joint wrist shown in U.S. Pat. No. 5,792,135, mentioned above, may be used.) The wrist 314 is essentially a roll-pitch-pitch-yaw wrist, with the roll being about axis 3, along the instrument shaft 312. The joint axes are labeled in FIG. 2, a portion of which is a kinematic diagram for the wrist shown in FIG. 12.

Figure 2:
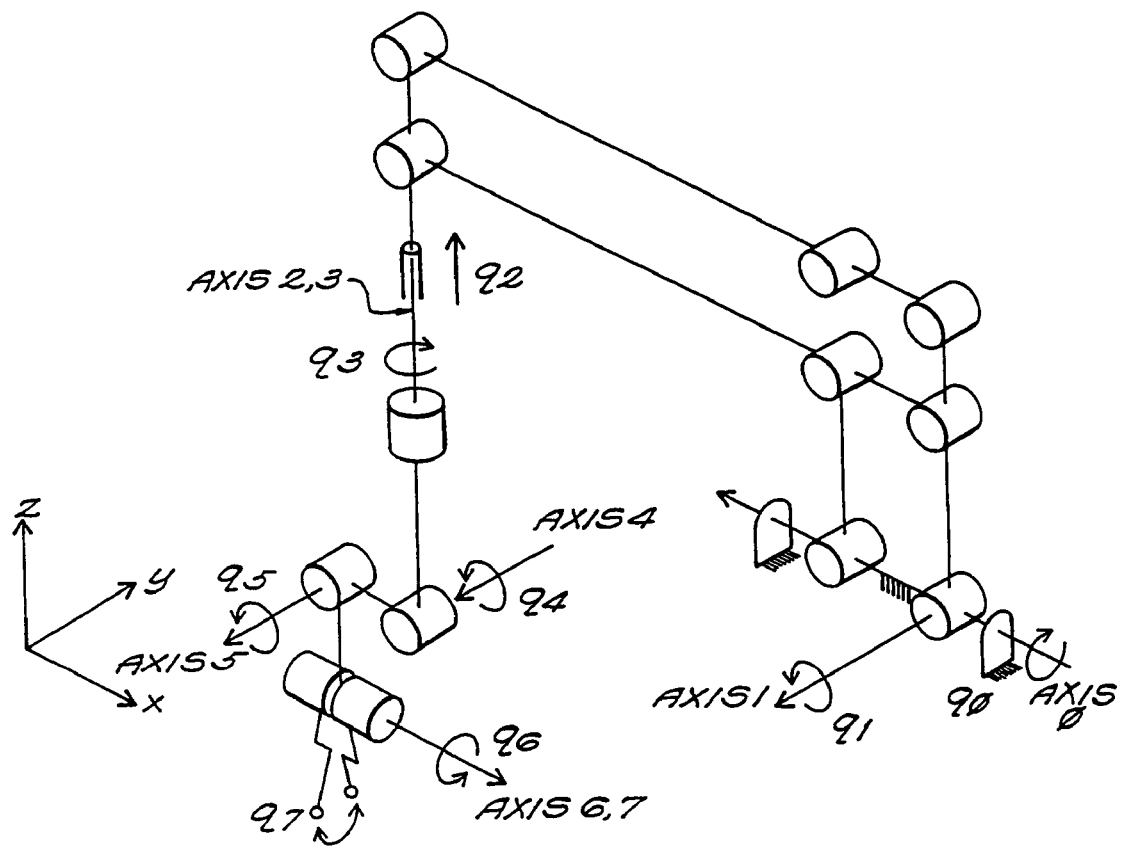
FIG. 2 is a schematic representation in a perspective view of the kinematics of the embodiment of a base positioning unit and wrist unit of the invention shown in FIG. 1, showing the joint orientations in a nominal "zero" position.

As shown in FIG. 2, each joint is labeled numerically. Joint 2 is a translational joint, effected by motion of the carriage 310 along its rails, which translates the shaft 312 of the wrist unit 304 along axis 2. Motion through this DOF from a nominal zero position (described below) is indicated as $q_2$. The first rotary joint of the wrist, joint 3, rolls the entire wrist 314 around axis 3, which is coincident with axis 2. The position of joint 3 is indicated by the angular displacement $q_3$. The next rotary joint is a first pitch joint, joint 4, which causes pitching of the remaining portion (joints 5, 6 and 7) of the wrist unit 304 about the axis 4, through an angular displacement q. Joint 4 supports an extension link 380, which extends to the next rotary joint joint 5. Joint 5 is a second pitch joint which causes pitching of the remaining portion (joints 6 and 7) of the wrist unit 304 about the axis 5, which is always parallel to the axis 4, through an angular displacement $q_4$. Joint 5 directly supports an effector support link 382, which is connected to joints 6 and 7 through an effector axle 384. The next rotary joint is a yaw joint, joint 6, which yaws one finger $318_b$ of a two finger unit around the axis 6, which is always perpendicular to axes 4 and 5. The angular displacement of a point that is midway between this first finger and the second finger, from the home position is designated with $q_6$. The final rotary joint is also a sort of yaw joint, joint 7, which yaws the other finger $318_a$ of the two finger unit around the axis 7, which is coincident with the axis 6. The opening angle between the second finger and the first finger is designated $q_7$. The two fingers can be moved together, or separately. If they are moved together, q, is considered to be zero.

All joint angles are defined relative to their respective proximal link closer to ground, except for joint 5, which is defined relative to axis 3. The zero configuration is shown in FIG. 2 with all angles equal to zero.

As will be discussed below, to implement macro-micro control, the combination of the base unit 302 and the wrist unit 304 must allow redundant macro and micro translations of a point on the end effector in, ideally, each of three independent orthogonal directions, that is, any direction. By "redundant translation in a direction" it is meant that for any configuration of the joints, there will be at least two joints that can accommodate translation desired. (For instance, the four joint wrist shown in U.S. Pat. No. 5,792,135, mentioned above, may be used.) The wrist 314 is essentially a roll-pitch-pitch-yaw wrist, with the roll being about axis 3, along the instrument shaft 312. The joint axes are labeled in FIG. 2, a portion of which is a kinematic diagram for the wrist shown in FIG. 12.

As shown in FIG. 2, each joint is labeled numerically. Joint 2 is a translational joint, effected by motion of the carriage 310 along its rails, which translates the shaft 312 of the wrist unit 304 along axis 2. Motion through this DOF from a nominal zero position (described below) is indicated as $q_2$. The first rotary joint of the wrist, joint 3, rolls the entire wrist 314 around axis 3, which is coincident with axis 2. The position of joint 3 is indicated by the angular displacement $q_3$. The next rotary joint is a first pitch joint, joint 4, which causes pitching of the remaining portion (joints 5, 6 and 7) of the wrist unit 304 about the axis 4, through an angular displacement q. Joint 4 supports an extension link 380, which extends to the next rotary joint joint 5. Joint 5 is a second pitch joint which causes pitching of the remaining portion (joints 6 and 7) of the wrist unit 304 about the axis 5, which is always parallel to the axis 4, through an angular displacement $q_4$. Joint 5 directly supports an effector support link 382, which is connected to joints 6 and 7 through an effector axle 384. The next rotary joint is a yaw joint, joint 6, which yaws one finger $318_b$ of a two finger unit around the axis 6, which is always perpendicular to axes 4 and 5. The angular displacement of a point that is midway between this first finger and the second finger, from the home position is designated with $q_6$. The final rotary joint is also a sort of yaw joint, joint 7, which yaws the other finger $318_a$ of the two finger unit around the axis 7, which is coincident with the axis 6. The opening angle between the second finger and the first finger is designated $q_7$. The two fingers can be moved together, or separately. If they are moved together, q, is considered to be zero.

All joint angles are defined relative to their respective proximal link closer to ground, except for joint 5, which is defined relative to axis 3. The zero configuration is shown in FIG. 2 with all angles equal to zero.

As will be discussed below, to implement macro-micro control, the combination of the base unit 302 and the wrist unit 304 must allow redundant macro and micro translations of a point on the end effector in, ideally, each of three independent orthogonal directions, that is, any direction. By "redundant translation in a direction" it is meant that for any configuration of the joints, there will be at least two joints that can accommodate translation in that direction. Redundancy in each of three independent orthogonal directions means that there will always be two such joints no matter in what direction translation is desired. Macro-micro redundancy means that of the two joints that provide for the translation, one is a micro joint and one is a macro joint.

If redundant motion is provided for in only two independent directions, (for instance if there were no joint 5) there would always be one direction (in that case, pointing directly into the fingers) where redundancy did not exist, which would result in poor force reflection in that direction. For instance, forces could not be felt along a line that passes through the finger tips and through axes 6/7 and which is perpendicular to that axis. The five joint wrist 314 of the invention avoids that problem by having an extra pitch degree of freedom and maintaining a right-angle bend in q5 (see FIG. 14) while reorienting.

Figure 14:
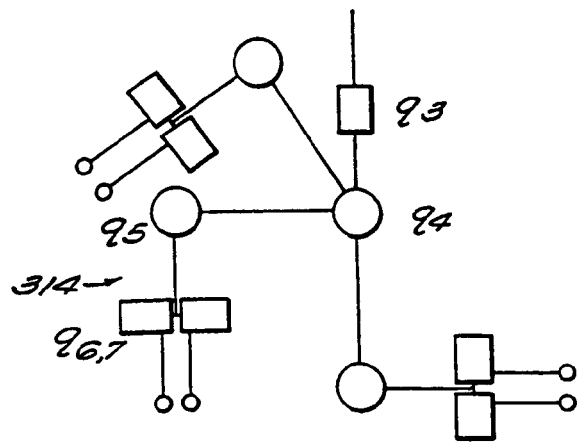
FIG. 14 is a schematic representation showing three different positions that the wrist of the invention shown in FIG. 12 can assume.

FIG. 14 shows a number of different orientations that the wrist 314 can assume. A redundant degree of freedom, (joints 4 and 5) is maintained corresponding to motions directly into (i.e., stubbing) the fingers. (This is not a macro and micro redundancy. The macro redundancy would be provided by at least one of joints 0, 1 and 2, depending on the joint configuration.)

Figure 15:
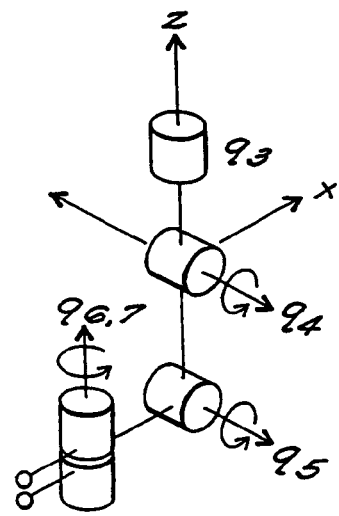
FIG. 15 is a schematic representation showing a position in which the wrist of the invention shown in FIG. 12 can be placed, which position is singular.

Such a wrist also presents some challenges. As compared to a wrist without joint 5, the wrist 314 has a kink in it. There is typically a limited amount of space at the surgical site and the extra room that this wrist occupies in certain configurations may not be available in all circumstances. Further, the wrist has essentially the same singularities as does a roll-pitch-yaw wrist. For example, a singular configuration from which the wrist could not be moved occurs when the wrist pitch is at $\pi/2$, ($q_5=\pi/2$) measured from the zero position shown in FIG. 2, as shown in FIG. 15.

Wrist Cabling and Mechanism

Figure 17:
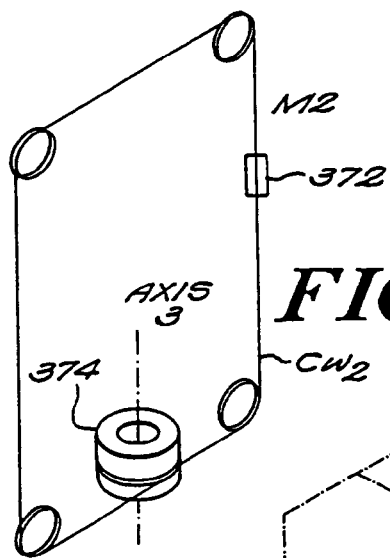
FIG. 17 shows schematically the wrist cabling for rotation of wrist joint 3 about axis 3, for an embodiment of the wrist of the invention shown in FIG. 12.
Figure 16:
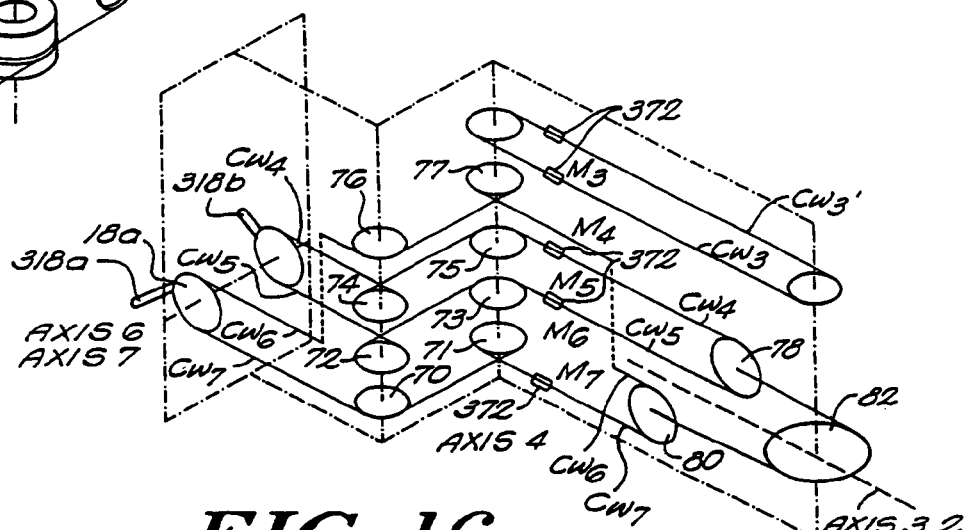
FIG. 16 shows schematically the wrist cabling for an embodiment of the wrist of the invention shown in FIG. 12.

FIG. 16 shows a schematic diagram of the cabling scheme for the wrist 314 shown in FIG. 12, for joints 2, 4, 5, 6 and 7. Cabling for rotary joint 3 is not shown in FIG. 16, but is shown in FIG. 17.

End Portion

The wrist is a roll-pitch-pitch-yaw wrist, where the joint 3 is the roll, joints 4 and 5 are the pitch joints, —joint 6 is the yaw and joint 7 is an open/close around the yaw axis. Both the fingers rotate about axes 6 and 7 as described below.

The wrist 314 is mounted to a hollow aluminum instrument shaft, 312, mounted along axis 3, through which six cables, $Cw_3$, $Cw_3$, $Cw_4$, $Cw_5$, $Cw_6$ and $Cw_7$ pass.

One of the objectives in designing a wrist is to keep the diameter of pulleys within the wrist as large as possible, where the upper limit will be the diameter of the instrument shaft. There are two reasons for this. First, cable, and especially metal, e.g., steel cable, has a minimum bending radius, about which it may turn, since repeated bending stresses in the cable will cause fatigue and failure in the individual cable fibers. The second reason is that there may be substantial friction caused by pulling cable over a small radius. The motion of cable fibers relative to each other increases as the pulley diameter decreases, while at the same time cable tension is distributed over a smaller area. Under load this internal rubbing of the individual cable fibers represents energy loss and manifests itself as friction in the overall drive. Although an embodiment of the invention is described herein using polymeric cables, there may be situations where the added strength of metal cables is beneficial.

The fingers may be serrated, designed to hold needles. Alternatively, they could be made as retractors, microforceps, dissecting scissors, blades, etc.

Wrist Cabling

An N+1 cabling scheme (driving N freedoms with N+1 cables) is used in a portion of the wrist 314. The cable layout is shown schematically in FIG. 16. A portion of the cable layout is shown less schematically, but also less completely in FIG. 18. The three joints: fingers 318a and 318b, and pitch joint 5, are driven by four cables $Cw_4$, $Cw_5$, $Cw_6$, and $Cw_7$. These four cables represent the minimum number of tension elements needed to actuate three freedoms. Due to the particular unusual arrangement of axes and cables in the wrist of the invention shown, it is also possible to provide translation of these joints along the translational axis 2, by pulling on all four of the cables $Cw_4$, $Cw_5$, $Cw_6$, and $Cw_7$ at once. This is not typical of an N+1 system.

The cables that actuate rotational motion about the instrument shaft 312, about axis 3, are omitted from FIG. 16, in order to more easily show cables $Cw_3$-$Cw_7$. The rotation results only in twisting of the cables $Cw_3$-$Cw_7$ inside the long instrument shaft tube 312. Due to the length of the instrument shaft 312, however, the resulting change in length of the cables is slight, and the length of the cables is long, so that the resulting resistance to rotational motion is on the order of the bearing friction in joint 3, and substantially less than the torque due to brush friction in the motor that drives this rotation (M2). This twisting of the cables does, however, limit rotation of the instrument shaft 312 to t 180°, at which point the cables will rub on each other, creating friction and wear.

As shown in FIG. 16, cables $Cw_7$ and $Cw_6$ form two sides of a continuous cable loop. Cable $Cw_7$ engages a proximal idler pulley 80, first intermediate idler pulley 70, a second intermediate idler pulley 71, and driven capstan 18a. The cable loop returns from the driven capstan 18a as cable $Cw_6$ and engages third and fourth intermediate idler pulleys 76 and 77, and proximal idler pulley 80.

The cable $Cw_7$ is coupled through a clamp 372 to one of the base cables $Cb_{d7\,(4,\,5,\,6\,or\,7)}$ that is driven by one of the motors M4, 5, 6 or 7 between the idler pulleys 80 and 71. These four motors together actuate the four joints 2, 5, 6 and 7, and it is arbitrary which motor is attached to which wrist cable. The cable $Cw_6$ is coupled through a clamp 372 to another of the base drive cables $Cb_{d\,(4,\,5,\,6\,or\,7)}$ that is driven by the motors M4, 5, 6 or 7 between the idler pulleys 80 and 77.

Cables $Cw_5$ and $Cw_4$ form two sides of another continuous loop of cable. Cable $Cw_5$ engages a proximal idler pulley 78, the intermediate idler pulleys 72 and 73 and driven capstan 18b. The second cable loop returns from the driven capstan 18b as cable $Cw_4$ and engages intermediate idler pulley 74, and 75 returning to and the proximal idler pulley 78.

The cable $Cw_5$ is coupled through a clamp 372 to another of the base cables $Cb_{d(4,\,5,\,6\,or\,7)}$ that is driven by the motors M4, 5, 6 or 7 between the idler pulleys 78 and 73. The cable $Cw_4$ is coupled through a clamp 372 to another one of the base cables $Cb_{d(4,\,5,\,6\,or\,7)}$ that is driven by the motors MA, 5, 6 or 7 between the idler pulleys 78 and 75.

The cable $Cw_3$ is coupled to joint 4. This cable has two tension sections, $Cw_3$ and $Cw_3$, only one of which is coupled directly to a motor. As such, it is not part of an N+1 configuration, but represents instead a 2N configuration. This cable and this joint are connected to base cable $Cb_{d3}$.

FIG. 17 shows a schematic of the cable $Cw_2$ used to drive joint 3, rotation about the axis 3. This cable is also shown in phantom on the right side of FIG. 18. The instrument shaft 312 is mounted to the driven capstan 374 (not shown in FIG. 18), so that they rotate together. The cable $Cw_2$ is clamped by a clamp 372 to a base cable $Cb_{d2}$, which is driven by the motor M2.

Figure 18:
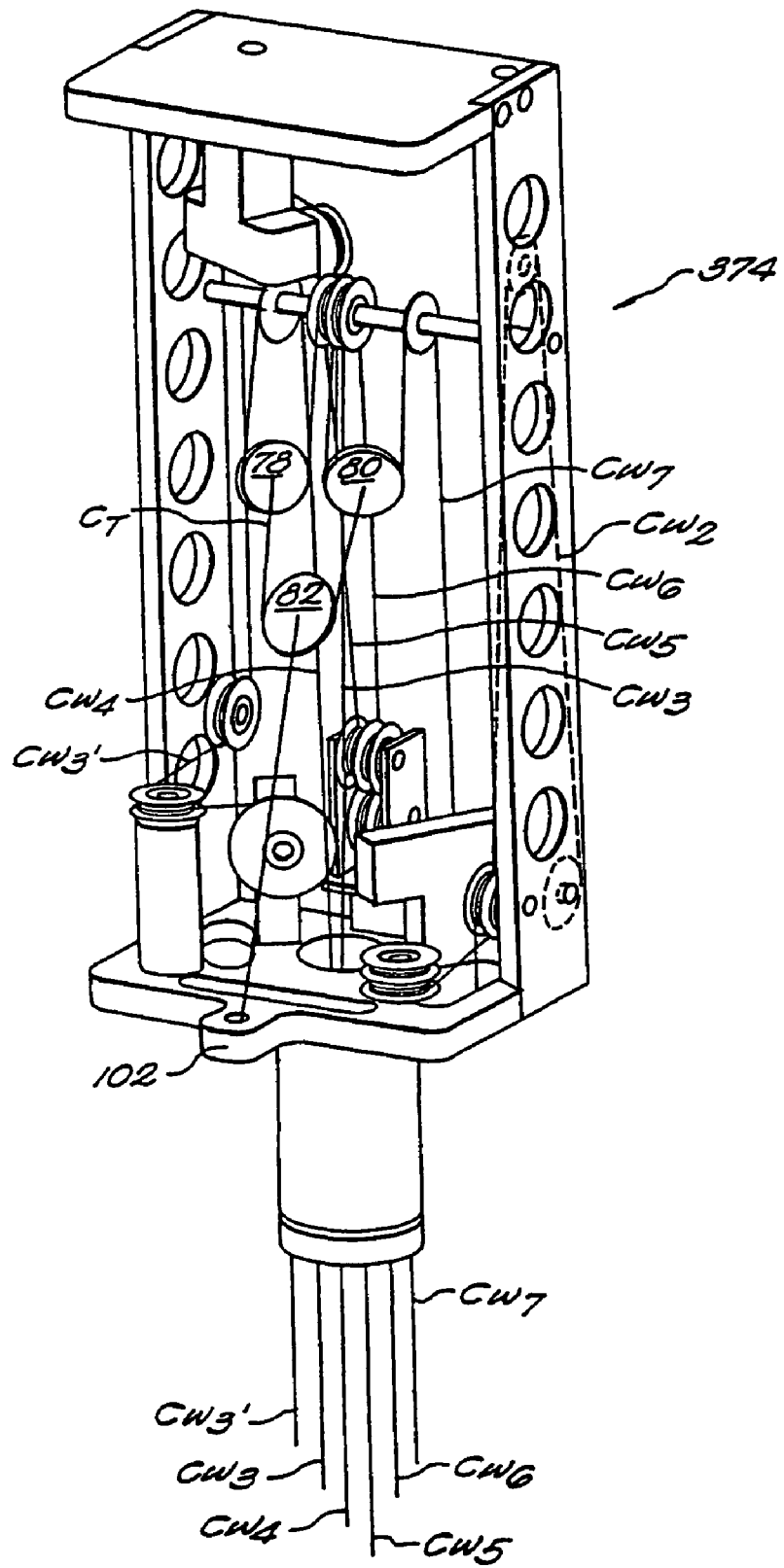
FIG. 18 shows schematically the portion of the wrist cabling distant from the wrist joints, for an embodiment of the wrist of the invention shown in FIG. 12.

The idler pulleys 78 and 80 are located in the top 374 of the wrist unit 304, shown in FIG. 18. They are tensioned by cable $C_T$ which is fixed kinematically to the center of proximal idler pulleys 78 and 80. The pulleys 78 and 80 ride on shafts (not shown) held in small forks into which the cables terminate. Each pulley uses a single ball bearing. The cable $C_T$, engages proximal idler pulley 82. Pulley 82 rides on a shaft held in a fork. This fork is mounted via a tensioning mechanism to the bracket 102, which allows turning of a screw in order to tension the cables. The cables are arranged so that this single tensioning point tensions all cables $Cw_2$-$Cw_7$.

The use of idler pulleys 78, 80, and 82 is unusual in N+1 cabling schemes. Typically, a separate motor is used for each of the N+1 cables. Using an extra motor has the advantage that the overall pretension in the system is actively adjustable, which is useful when using a relatively high friction transmission, such as cable conduits. However the disadvantages are that an extra motor is required, and tension is lost when motor power is turned off. This results in an unraveling of cables at the driving capstan where multiple wraps are used to drive the cable. A pretensioned N+1 arrangement is much more convenient, while maintaining the advantage of minimizing cables which must pass through the shaft into the wrist and simplifying the wrist design.

The movement of the wrist and fingers is caused by coordinated motion of the motors. If motors M4 and M7 both act in concert, such that the cable around the capstan 18a is urged in the same direction, e.g. clockwise, as shown, by both motors, then finger 318a will rotate. Similarly if motors M5 and M6 act in concert, finger 318b will rotate. These separate rotations, acting against each other provide gripping. If motors M5 and M6 act in opposition, such that they pull the cable around the capstan 18a in opposite directions (thereby pulling cables $Cw_4$ and $Cw_5$ to cause the cables to move in the same directions as each other, e.g. clockwise, around pulleys 74 and 72), and motors M4 and M7 act in opposition to each other, and also act relative to M5 and M6, such that the cables $Cw_6$ and $Cw_7$ are caused to move around the pulleys 76, and 70 in the same direction as cables $Cw_4$ and $Cw_5$ move around pulleys 74 and 72, then the wrist will pitch about axis 5. Finally, if all motors M4, M5, M6 and M7 act such that they pull the cables around the capstans 18a and 18b in the same direction, e.g. to the right, as shown in FIG. 16, the entire wrist unit will translate along axis 2. The exact differential transformations for the wrist described below, are given below.

As shown in FIG. 16, the cables for the joints 5, 6, and 7 pass through joint 4 on idler pulleys 71, 73, 75, and 77. Two of the six cables that pass through the instrument shaft actuate joint 4 (making up the loop that includes the cable $Cw_3$ and $Cw_3$'). Joint 4 is actuated by motion of motor M3 alone. Rotation around axis 3 is actuated by motion of motor M2 alone, as shown in FIG. 17.

In some cases, the use of alpha wraps within the wrist (e.g. at joint 4, around pulley 71) adds a considerable amount of friction. A wrist can be designed such that there are no alpha wraps. However this comes at a cost of increasing the number of pulleys in the wrist and lengthening the wrist. If the four joint wrist shown in FIG. 12 were cabled were designed to avoid alpha wraps, eight additional pulleys would be needed, which would consume a considerable amount of space and add offsets to the kinematic structure. To minimize the added friction but still use an alpha-wrap design, non-metallic cable can be used, in particular Spectra type fiber in the form of Spiderwire™ fishing line, available from Johnson Worldwide Associates, Sturtevant, Wis. This material is not as stiff as stainless steel cable, but it is smaller in diameter and is much smoother on its outside surface. As a result, as the cable slides on itself, as is inevitable in an alpha wrap, very little friction is added.

The use of ballbearings was avoided in a preferred embodiment of the wrist unit. This makes sterilization easier, as there are fewer places for bacteria to grow, and there is no lubricant to be lost during the sterilization process. Thus, the wrist described can be used for minimally invasive surgery applications.

Each finger 318a, 318b is machined as a single piece, with the pulley 18a, 18b that drives it. They are stainless steel with clearance holes drilled in them, that ride on steel shafts made from drill rod. The friction torque is low because the shafts are only 0.047 in diameter. The shafts may also be titanium nitride coated stainless shafts, to avoid galling. The idler pulleys are made from teflon and simply have clearance holes so that they ride smoothly on drill rod shafts. Because they are thin, and the alpha wrapped cable produces a moment on the pulleys, the pulleys must support themselves by leaning on each other. Despite the low coefficient of friction of teflon, this is still a major source of wrist friction. Because teflon is very soft, a teflon filled delrin may be a better choice for this component. The main structural wrist components are machined from 303 stainless steel.

Base—Wrist Interface

FIG. 18 shows a view of the top of the wrist unit. This portion holds a number of idler pulleys. The six cables shown in FIG. 16 that pass through the instrument shaft 312 and the cable loop, which drives the wrist roll joint 3, about axis 3, shown in FIG. 17, all pretension within this unit against various idler pulleys, some of which move against screws to allow pretensioning. Six of the cable segments are aligned against the back of the wrist unit 374, such that they precisely align with the six drive cables $Cb_{d2}$-$Cb_{d7}$ within the base unit, which run parallel to link 5. FIG. 18 shows these parallel cables, arranged, as shown, from right to left, as follows: $Cw_2$, $Cw_7$, $Cw_6$, $Cw_s$, $Cw_3$, $Cw_4$. These six wrist cable segments are then mechanically fixed to their respective drive cables, for instance, using screw clamps, as shown in FIG. 13. The screw clamps are located roughly at the location of reference numeral $Cw_6$ in FIG. 18, for each cable. (Due to the perspective in FIG. 18, the cables are not shown as precisely parallel lines. However, they are, in fact, parallel.)

FIG. 19 shows the connection between the wrist unit and the base unit, simplified for a single degree of freedom. As can be seen from this side view, the base drive cable returns around the pulley P7 and then one segment $Cb_d$ of the base drive cable passes adjacent to a portion of the wrist cable $Cw$. The other segment $Cb_r$ of the base drive cable is tensioned by the pulley P8 and passes near to the wrist cable $Cw$, but not so near as the portion $Cb_d$. The drive and wrist cables respectively are held together by the clamp 372. The wrist cable $Cw$ is shown in FIG. 19 to be a loop, the other segment of which, $Cw'$, is shown on the opposite side of the wrist unit, not engaged by any other drive cables. For any given wrist cable, this may or may not be the case. For instance, the cable $Cw_2$, which rotates the entire wrist unit 304 about the axis 3, is engaged by only one base drive cable $Cb_{d2}$. However, the cable $Cw_s$, which is connected to joints 5 and 7 in the wrist, is itself engaged to a drive cable. The cable $Cw_5$ is part of a continuous loop, of which the wrist cable $Cw_4$ is also a part. This wrist cable $Cw_4$ is also connected to joints 5 and 7. It is also connected itself to another of the base drive cables.

A generic set of attachments is shown in FIG. 13. The base drive cables are shown in heavy line. Six continuous base loops are represented, each designated $Cb_{xn}$, where x is either d or r and n is 2, 3, 4, 5, 6 or 7. The x component indicates whether the cable is a drive segment or a return segment of the continuous base cable loop. The numerical n component indicates to what motor the drive cable is coupled. The indication "to $P7_2$" means that the cable goes to the pulley P7 that is associated with the motor M2.

Because the cables in the wrist unit align parallel with the respective cables in the base unit, no further mechanism is required to make an attachment other than a single small clamp per cable. In other words, no complex mechanical interlocking mechanism is required, and the actual connection between the wrist unit and the base unit is frictionless.

Differential Kinematics

The relationships between the motor velocities and joint velocities for the joints 2-7 are discussed next. The motor-joint mapping for joints 0 and 1 are simply speed ratios. A matrix q represents the velocities of joints 2-7. All of the joint angles are measured with respect to the previous link except joint 5, which is measured with respect to the axis 2 of the instrument shaft 312. For instance, as shown in FIG. 14, the joint angle $q_5$ is −50°, 0°, and +90°, starting with the uppermost configuration and going counterclockwise. A matrix c represents the velocities of the six base drive cables that run parallel to link 5. $R_3$, $R_4$, $R_5$, and $R_6$ are speed ratios defined below for the embodiment described above.

$$R_3 = 8.717 \times 10^{-3} \text{ m/rad}$$

$$R_4 = 6.252 \times 10^{-3} \text{ m/rad}$$

$$R_5 = 3.787 \times 10^{-3} \text{ m/rad}$$

$$R_6 = 3.094 \times 10^{-3} \text{ m/rad} \tag{5}$$

We then have:

$$\dot{q} = J\dot{c}, \text{ where:} \tag{6}$$

$$J = Rm \begin{pmatrix} 1 & 0 & 0 & 0 & 0 & 0 \\ 0 & \frac{1}{R_3} & 0 & 0 & 0 & 0 \\ 0 & 0 & \frac{1}{R_4} & 0 & 0 & 0 \\ 0 & 0 & 0 & \frac{1}{R_5} & 0 & 0 \\ 0 & 0 & 0 & 0 & \frac{1}{R_6} & 0 \\ 0 & 0 & 0 & 0 & 0 & \frac{2}{R_6} \end{pmatrix} \begin{pmatrix} 0 & 1/4 & 1/4 & 1/4 & 1/4 & 0 \\ 0 & 1/4 & 1/4 & 1/4 & 1/4 & -1 \\ -1 & 1/4 & 1/4 & 1/4 & 1/4 & 0 \\ 0 & -1/4 & 1/4 & 1/4 & -1/4 & 0 \\ 0 & -1/4 & -1/4 & 1/4 & 1/4 & 0 \\ 0 & -1/4 & 1/4 & -1/4 & 1/4 & 0 \end{pmatrix}, \tag{7}$$

where Rm is a scalar which represents the ratio between motor rotation in radians to cable motion in meters.

The teleoperator slave of the invention discussed above has a number of positive features. The structure is stiff and strong. This results in low flexibility, which provides good control performance and endpoint measurement. The actuators are strong and well matched to the overall inertia, resulting in good positioning performance and grip strength, so that needles may be securely held in a gripping end-effector. The carriage uses a bearing system that is rather stiff and low in friction. The first two axes of the system (0 and 1) are counterbalanced. This provides safety and convenience, since the slave will not move when motor power is shutdown, which is particularly important if the end-effector is in a patient's body. The wrist unit 304 is detachable. This allows different wrist units to be used for different tasks, while using the same base unit 302. The five joint end effector allows force reflection with respect to three translational DOFs. (This is discussed below.)

A brief discussion of the performance of the slave of the invention follows. Basic data, on a joint by joint basis, is given first, followed by tests to quantify force reflection performance. The ability to perform tasks is also confirmed, in particular, suturing and a more difficult task of moving a piece of soft plastic tubing along a "S"-shaped curved wire.

Joint Limits

The range of motion of each of the slave joints is given relative to the zero position defined in FIG. 2.

$$q_0 \pm 80°$$

$$q_1 \pm 60°$$

$$q_2 \; 8 \text{ in}(20 \text{ cm})\text{stroke}$$

$$q_3 \pm 180°$$

$$q_4 \; -27° + 40°$$

$$q_5 \pm 180° - q_4 + 30° - q_4$$

$$q_6 \pm 100°$$

$$q_7 + 200° \text{ jaw opening} \tag{8}$$

Structural Stiffness

Estimates for the structural stiffness at the endpoint of the slave described above is given below. These values are difficult to measure and are believed to be accurate to about 20%. Stiffness was calculated by measuring the force required to deflect the instrument shaft by $\frac{1}{16}$ in (0.16 cm) in the x direction and $\frac{1}{8}$ in (0.32 cm) in the y direction using a force gauge. The z direction structural stiffness is that found for the base unit.

$$k_{wx} \cong 9500 \text{ N/m}$$

$$k_{wy} \cong 2800 \text{ N/m}$$

$$k_{wz} \cong 12000 \text{ N/m} \tag{9}$$

These measurements were made with the wrist unit centered in its stroke. The point where force was applied was 0.15 m (6 in) below the teflon support bushing 370, and 0.086 m (3.4 in) below the remote center 111.

Friction

The force required to backdrive each joint of the wrist with the base joints 0 and 1 held stationary, and when the manipulator was in its zero position (FIG. 2) was measured. In each case four to six measurements were made and averaged.

$f_R$ is a force in the x direction applied in line with axis 5, which causes rotation about axis 3 only.

$f_x$ is a force at the finger tips in the x direction with the fingers closed. Axis 3 is held fixed, so only axis 6 may rotate.

$f_y$ is a force at the finger tips in the y direction. Only axis 5 rotates.

$f_Z$ is a force at tip in z direction. Only axis 4 rotates.

$f_{q2}$ is the force required to backdrive the carriage 310 and wrist unit 304 together.

In the first case, these forces were measured with the 5 system turned completely off.

$$f_R = 0.63 \pm 0.04 \text{ N}$$

$$f_X = 1.1 \pm 0.2 \text{ N}$$

$$f_Y = 0.60 \pm 0.2 \text{ N}$$

$$f_Z = 0.96 \pm 0.06 \text{ N}$$

$$f_{q2} = 12.9 \pm 0.03 \text{ N} \tag{10}$$

In the second case, a friction compensation algorithm was applied, which was used throughout the remainder of the results given. This algorithm will not be described here in detail. It essentially feeds forward a torque to each motor as a function of motor velocity and includes a model of the brush friction and brush flexibility. When the friction compensation algorithm is implemented, the measured friction values are:

$f_R$=0.48±0.01 N $f_X$=0.88±0.14 N $f_Y$=0.40±0.02 N.

$f_Z$=0.73±0.07 N $f_{q2}$=2.86±0.2 N (11)

The friction is created in two places, within the wrist itself (cables, pulleys, etc.) and in the motors as brush friction. The fact that joint 2 friction $f_{q2}$ can be reduced by a factor of four indicates that this axis is dominated by brush friction, because brush friction is the type of friction for which the compensation algorithm compensates. However, in the other cases, where the compensation does not reduce overall friction substantially, the friction must be in the mechanics of the wrist.

Master

Figure 20:
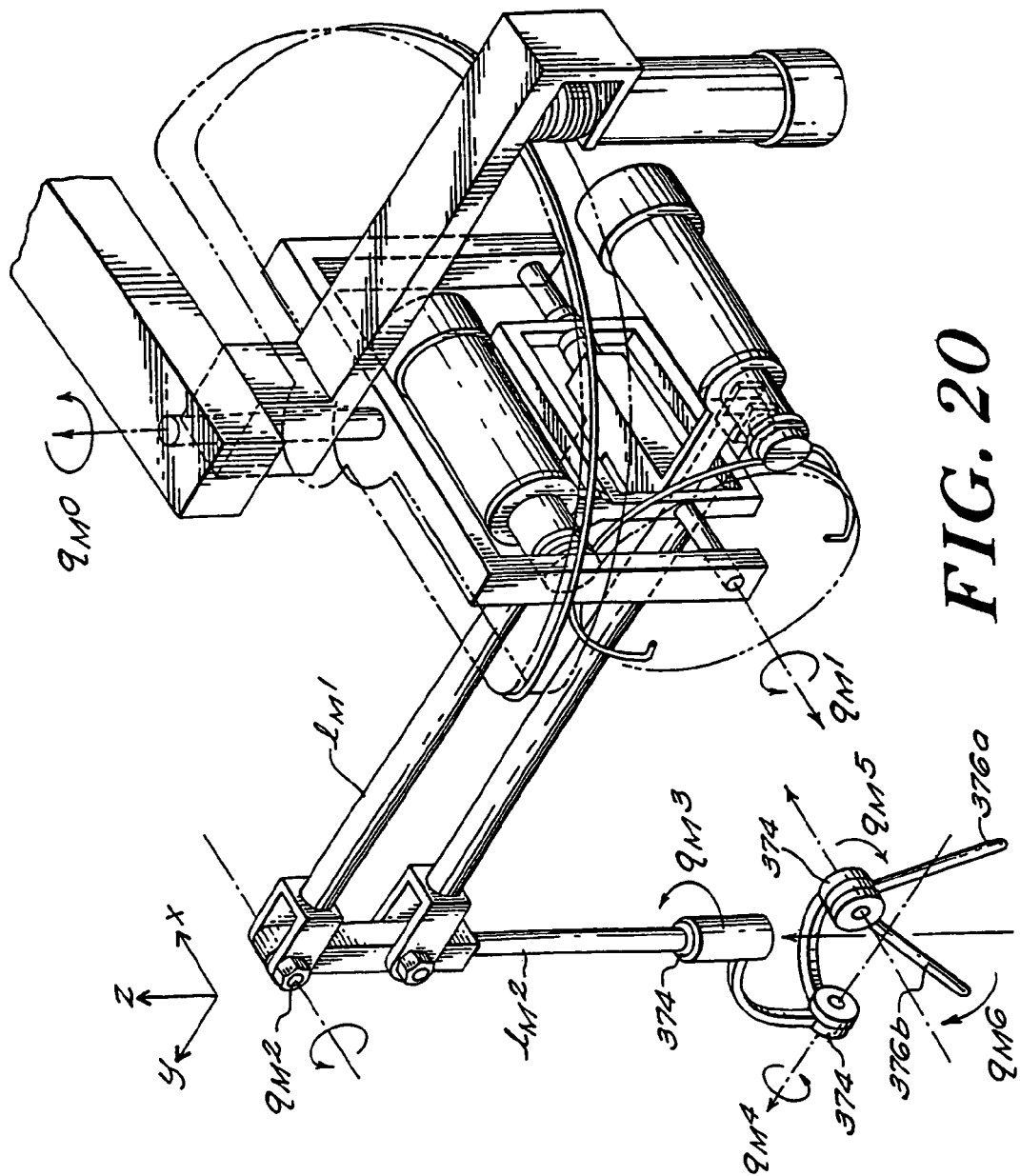
FIG. 20 is a schematic representation showing a perspective view of a master unit of a preferred embodiment of the invention.
Figure 21:
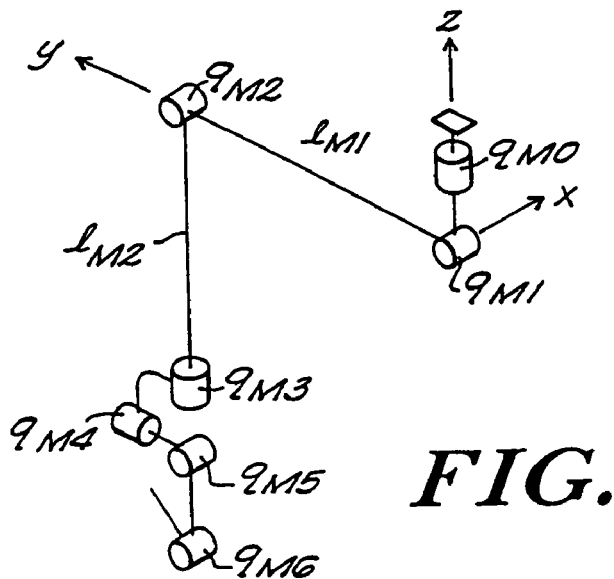
FIG. 21 is a schematic representation showing the kinematics of a master unit of a preferred embodiment of the invention shown in FIG. 20.

A suitable master manipulator is a modified version of the PHANToM™ brand haptic interface. Various models of such haptic interfaces are available from Sensable Technologies, Inc., of Cambridge, Mass. Such a haptic master is described in U.S. Pat. No. 5,587,937, issued on Dec. 24, 1996, and shown in perspective view in FIG. 20. The U.S. Pat. No. 5,587,937 patent is hereby incorporated fully herein by reference. FIG. 21 is a schematic showing the master kinematics.

The Cartesian axes of the master shown in FIG. 21 are aligned with those shown in FIG. 2 of the slave during use of the system such that master motions along its x axis cause slave motions along its x axis. The master is shown in its zero position. The system is essentially a three DOF manipulator, which is approximately counterbalanced using the weight of its own motors. The standard PHANToM™ interface uses a passive three DOF gimbal at the end of the actuated three DOF arm $l_M1$, as shown in the above referenced '937 patent. The gimbal has been replaced with a version that uses panel mount optical encoders 374 with 256 counts/rev. (available from Bourns Inc., of Riverside, Calif., Model #ENS1JB28L00256) to measure the gimbal joint $q_M3$, $q_M4$, $q_M5$, positions. A seventh joint between opposed interface elements 376a and 376b was also incorporated $q_M6$ into the last link of the gimbal to control gripping motion of the slave manipulator. The master gripper uses a spring opening return so that the user can operate the opposed interface elements 376a and 376b somewhat like a pair of tweezers.

The link lengths are:

$l_M1$=0.143 m $l_M2$=0.178 m (12)

and the speed ratios are:

$R_0$=9.970

$R_1$=9.936.

$R_2$=9.936 (13)

Each master motor is capable of producing 29.61 mNm (milli-Newton-meters) of maximum continuous torque. At two times max rated continuous torque (which is typically how the system is run), maximum endpoint force values can be achieved of:

$f_{MX}$=4.1 N $f_{MY}$=4.1 N.

$f_{MZ}$=3.3 N (14)

Each master motor encoder is a Hewlett-Packard optical encoder with 2000 counts/revolution {after quadrature). This gives an endpoint measurement resolution of:

$r_x$=4.51×10$^{-5}$ m(1.77×10$^{-3}$ in)

$r_y$=5.63×10$^{-5}$ m(2.22×10$^{-3}$ in).

$r_z$=4.52×10$^{-5}$ m(1.78×10$^{-3}$ in) (15)

A passive gripper does not allow the user to feel gripping forces, but it is relatively lightweight. An actuated gripper allows the user interface to feel and to control gripping. If an actuated gripper is used in the master, the master must be modified to carry the weight of such an actuated gripper. This can be done by adding appropriate counterweight, and bigger motors and by counterbalancing the gimbal itself. The actuated gripper can consist of tweezer type implements as shown, or of a pair of standard type needle holder handles attached to a single rotary axis. One handle is fixed to the gimbal end, while the other is attached via a cable transmission to a brushed D.C. electric motor (such as Maxon RE025-055-035, graphite brushes). Of course, if the slave does not have an actuated end effector, such as if the end effector is a saw, or a knife blade, then the master need not have an actuated user interface element.

Inertia

The inertias of each joint of the slave were calculated by plotting oscillatory step responses where very little damping and a known spring constant (position gain) were used. These were compared to a simulation of a spring, mass and damper system. The simulation mass and damping were modified until a fit was found to find the actual mass and damping.

$I_0$=0.32 kgm$^2$ $I_1$=0.25 kgm$^2$ $I_2$=3.35 kg $I_3$=26.0×10$^{-6}$ kgm$^2$ $I_4$=20.0×10$^{-6}$ kgm$^2$ $I_5$=20.5×10$^{-6}$ kgm$^2$ $I_6$=19.5×10$^{-6}$ kgm$^2$ $I_7$=2.8×10$^{-6}$ kgm$^2$ (16)

Individual Joint Responses

To give an idea of the position servo performance available with the invention, individual joint responses are first shown for a fairly well tuned set of gains given below:

$K_{qr0}$=3500 Nm/rad $K_{qr1}$=3500 Nm/rad $K_{qr2}$=20000 N/m $K_{qr3}=1.5$ Nm/rad $K_{qr4}=0.8$ Nm/rad $K_{qr5}=0.3$ Nm/rad $K_{qr6}=0.2$ Nm/rad $K_{qr7}=0.05$ Nm/rad  (16)

$B_{q0}=35$ Nms/rad $B_{q1}=35$ Nms/rad $B_{q2}=200$ Ns/m $B_{q3}=0.015$ Nms/rad $B_{q4}=0.008$ Nms/rad $B_{q5}=0.003$ Nms/rad $B_{q6}=0.002$ Nms/rad $B_{q7}=0.0005$ Nms/rad  (17)

During master-slave operation, gains for joint 0 and 1 of much lower than 3500 were used, because the system was not stable at these high gains. This may have been due to limited position measurement resolution in the master. A joint 0 gain of 3500 N/m corresponds to an endpoint stiffness of 128,400 N/m, when the tip of the slave fingers are at a distance of 0.17 m from the remote center. This is an extremely high endpoint stiffness. The endpoint resolution about joint 0 is the result of a 4096 count encoder and a 137:1 speed reduction, which gives 561,152 counts/rev or at 0.17 m a $3.03 \times 10^{-7}$ m resolution. The inertia of this axis is high, at 0.32 kgm², so that the bandwidth of the response is only $\sqrt{3500/0.32}=104$ rad/sec≅17 Hz. With such high positioning resolution and inertia, such high stiffness is clearly achievable. However, the master used had an endpoint resolution of only $4.511 \times 10^{-5}$ m. Therefore, if the slave tracks the master at this high gain, each time the master moves by one encoder tick, the slave sees a force step of 5.8 N or 1.3 lbs. Tracking such a coarse input creates noticeable vibration in the system.

Also, the slave shows a structural flexibility at roughly 8-12 Hz. It is believed that the vibration caused by tracking the coarse master input combined with these structural dynamics caused instability at high gains and forced detuning the slave joint 0 and 1 gains to 200 Nm/rad, which corresponds to an equivalent endpoint stiffness of 6920 N/m. One encoder tick movement on the master corresponds to a 0.31 N(0.07 lb) force step for the slave.

Thus, the designer must keep these matters in mind.

The second reason the gains are different during the force reflection tests is that they must be adjusted to have a 2:1 force scaling. For the test, joint P.D. (position/derivative control gains were used (instead of a cartesian P.D. mapped to joints via a $J^T$ (Jacobian transpose)).

The joint gains must be set to give an endpoint gain which is ½ that of the master, or 240 N/m. These gains are dependent on the configuration of the wrist. For the force reflection tests, where the manipulator was always nominally in its zero position (FIG. 2) the gains given below were used:

$K_{qs0}=200$ Nm/rad $K_{qs1}=200$ Nm/rad $K_{qs2}=20000$ N/m $K_{qs3}=0.12$ Nm/rad $K_{qs4}=0.10$ Nm/rad $K_{qs5}=0.20$ Nm/rad $K_{qs6}=0.10$ Nm/rad $K_{qs7}=0.04$ Nm/rad  (18)

$B_{q0}=10$ Nms/rad $B_{q1}=10$ Nms/rad $B_{q2}=250$ Ns/m $B_{q3}=0.004$ Nms/rad $B_{q4}=0.003$ Nms/rad $B_{q5}=0.004$ Nms/rad $B_{q6}=0.003$ Nms/rad $B_{q7}=0.0007$ Nms/rad  (19)

Basic Teleoperator Controller Selection

Before consideration of the force reflecting capabilities of the invention, a brief review of general control background is helpful. A useful configuration for a master-slave system is where a 'macro-micro' manipulator is used as the slave. As used herein, a "macro-micro" manipulator has a lightweight, short range, small manipulator mounted serially on a heavier, longer range, larger manipulator, which larger manipulator is kinematically closer to ground. In some of the following discussion, the heavy manipulator is referred to as the proximal manipulator, and the lightweight manipulator is referred to as a distal manipulator. The macro and the micro manipulators are redundant, with respect to translation in any direction, as defined above. It has been found that a Jacobian Inverse type controller enables achieving satisfactorily scaled force reflection using a one-degree-of-freedom experimental master-slave, macro-micro testbed and the three DOF embodiment of the invention shown in FIG. 1.

Basic Force Reflecting Teleoperation

Consider a master manipulator and a slave manipulator, each with its own sensors, actuators, power supplies and amplifiers. Controlling each manipulator is a computer, which reads sensor values from each, and which commands actuator inputs (e.g. supply currents for an electric) based on a controller program operating on the computer. Using such a system, a human operator can interact with the slave environment. In the case of the present invention, this may be a surgeon interacting with tissues at the surgical site.

Only force feedback is considered here.

A Basic Teleoperator

The dynamics of a kinematically similar master and slave may be expressed as $$H_m(q_m)\ddot{q}_m + C_m(q_m,\dot{q}_m)\dot{q}_m + G_m(q_m) = -\tau_m \quad (20)$$

and $$H_s(q_s)\ddot{q}_s + C_s(q_s,\dot{q}_s)\dot{q}_s + G_s(q_s) = -\tau_s, \quad (21)$$

where q is the vector of joint positions, H is the inertia matrix (being a function of the joint positions), $C\dot{q}$ are coriolis torques (being a function of both the joint positions and the joint velocities), G are gravitational torques (being a function of the joint positions), and $\tau$ are vectors of motor torques.

To control the system, gravity is compensated for by calculating and feeding forward gravitational torques, and using P.D. (position and derivative) feedback to force tracking between the master and slave joints.

$$\tau_m = -G_m(q_m) + \tau_{PD}$$

$$\tau_s = -G_s(q_s) - \tau_{PD}$$

$$\tau_{PD} = K(q_m - q_s) + B(\dot{q}_m - \dot{q}_s) \quad (22)$$

If the feedback gains K and B are symmetric positive definite matrices, the master and slave will appear to be connected via a spring and damper.

Jacobian Transpose Cartesian Control

The basic controller discussed above assumes a kinematically similar master and slave. If this is not the case (as it is not with the master and slave of the invention described above,) then the most straightforward method of cartesian endpoint control is to implement tracking between the endpoints of the master and the slave manipulators. The endpoint position x and endpoint velocity $\dot{x}$ are calculated, based on the measured actuator positions and using the manipulator geometry. A P.D. (position and derivative) controller is then applied to find the resulting endpoint forces and torques F for both master and slave. These are then converted to joint torques $\tau$ for all of the joints and commanded to the master and slave motors.

Endpoint velocities are calculated as follows, where J is typically referred to as the respective manipulator Jacobian:

$$\dot{x}_m = J_m(q_m)\dot{q}_m$$

$$\dot{x}_s = J_s(q_s)\dot{q}_s \quad (23)$$

The joint specific P.D. is replaced with a Cartesian version:

$$F_{PD} = K(x_m - x_s) + B(\dot{x}_m - \dot{x}_s)$$

$$F_m = F_{PD}$$

$$F_s = F_{PD} \quad (24)$$

The joint torques that are commanded to the motors to achieve desired positions/velocities are then calculated:

$$\tau_m = J_m^T(q_m)F_m - G_m(q_m)$$

$$\tau_s = J_s^T(q_s)F_s - G_s(q_s) \quad (25)$$

Figure 22A:
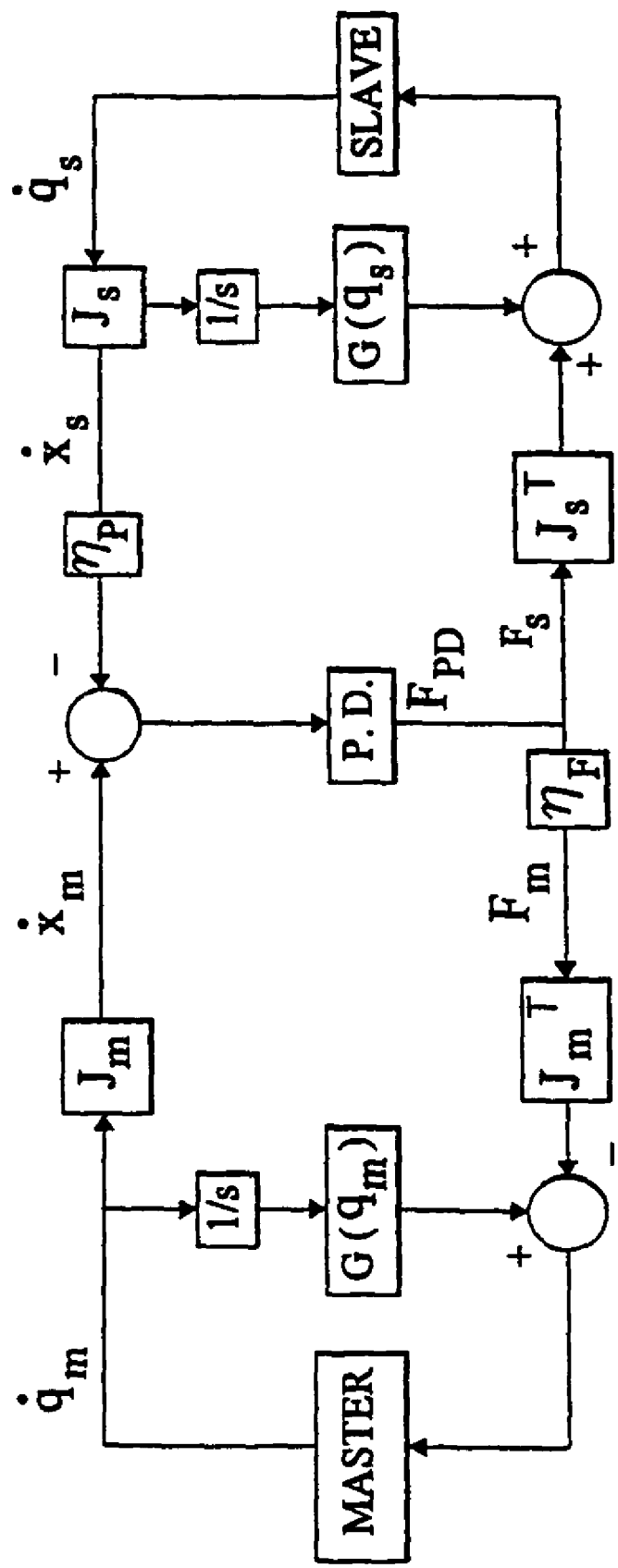
FIG. 22A is a schematic representation in block diagram form showing a known Jacobian transpose position-derivative control scheme for a master and a slave.

FIG. 22A shows such system in block diagram form (with the kinematic transformations included optional scaling factors discussed below).

Scaling

One way to change the user's perception of the environment is to scale positions and forces between the master and the slave. Scaling may be introduced into the above system to change the size of relative motions and to amplify forces between the master and slave. This is done by introducing the scale factors $\eta_F$, as shown in FIG. 22.

Scaling affects the user's perception of the environment and of the teleoperator as follows:

If $\eta_F>1$, and $\eta_p=1$, then forces are scaled up from the slave to the master. Velocities are one to one. The user feels an increased slave/environment impedance. Objects in the environment feel stiffer and heavier. This makes transitions between freespace and contact feel more crisp and noticeable. However, the friction and inertia of the slave will also be amplified and felt by the user. As a result, these undesirable elements will have to be very low in the slave if $\eta_F$ is to be large. Conversely, the environment feels a reduced master/user impedance. The environment will more easily backdrive the master and human operator.

If $\eta_F<1$, and $\eta_p=1$, then forces are scaled down from the slave to the master. Velocities remain one to one, the situation is inverse of the previous case. As long as $\eta_F>0$, some level of force reflection will exist.

If $\eta_p>1$, and $\eta_F=1$, then positions are scaled up from the slave to the master. Forces remain one to one. Motions made by the human operator are reduced, making fine motions easier to perform. Steady state forces are equal at the master and slave. Therefore, the user feels a decrease in slave/environment impedance. Transitions made between freespace and contact feel softer and are more difficult to distinguish.

If $n_p<1$, and $n_F=1$, then positions are scaled down from the slave to the master. Forces remain one to one. Fine motion control is more difficult, since errors in the user's motions are amplified. But the slave/environment impedance increases as felt by the master/user so that contacts are easier to distinguish.

If $\eta_F>1$, and $\eta_p=1/\eta_F$, then positions are scaled down from the slave to the master, but forces are scaled up in such a way that the environment stiffness appears unchanged to the user.

Macro-Micro Control

Figure 23:
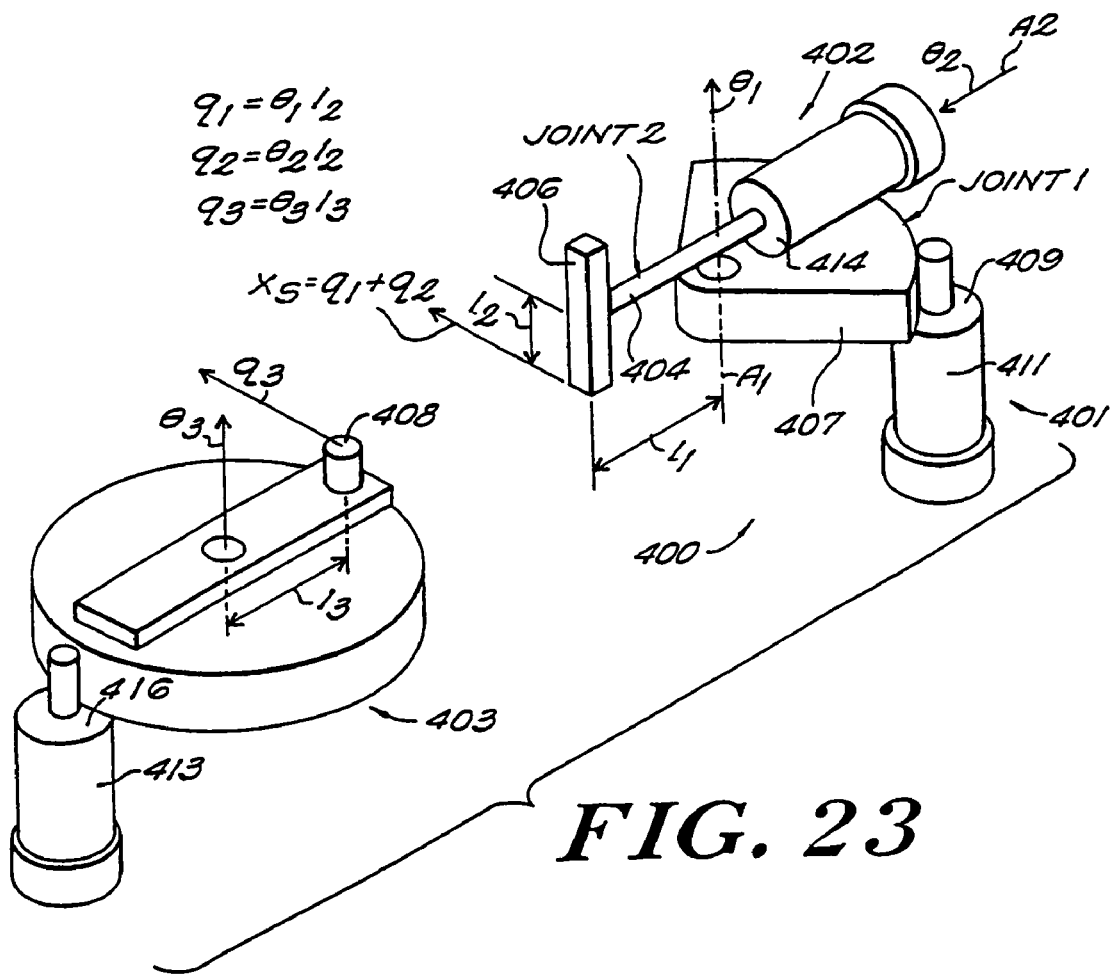
FIG. 23 is a schematic representation of a one DOF master and slave apparatus to illustrate macro-micro control.

As mentioned above, it is beneficial to use a macro-micro manipulator as the slave in a master-slave system. Referring to FIG. 23, the principle behind the macro-micro control of positioning mechanism base 304 and wrist 302 is described. A "macro-micro" manipulator slave has a lightweight manipulator, mounted on a heavier manipulator. The slave can have a "sensitive" end effector (wrist and fingers), which is lightweight and low in friction, but with a small range of motion. If this wrist is mounted on the end of a larger manipulator, with consequently larger inertia and larger range of motion, it is possible to suppress the reflected inertia of the macro manipulator, so that the user who engages the master does not feel it, and to have an endpoint impedance that approaches that of the micro manipulator.

A high quality, force-reflecting teleoperation with force scaling of at least 2:1 and perhaps 10:1 can be achieved, with the embodiment shown in FIG. 1, without the use of explicit force sensing. The control effectively (a) hides much of the inertia of the slave manipulator from the user, at the master, who feels primarily the dynamics of the master and that of the slave micro actuator end effector, and (b) therefore makes the slave respond more readily to forces from the environment.

It is not desirable to reduce the inertia of the master as well. Even though the user feels both the inertia of the master and the slave, because of force scaling, the inherent symmetry of the system is broken. If master forces are magnified with respect to slave forces, then the master must be able to achieve a proportionately higher servo stiffness than the slave. Reducing the inertia of the master reduces the servo stiffness that the master can achieve. In this case, it is desirable to have a master inertia larger than the slave, in direct proportion to the force scale factor.

Macro-micro control, as defined here, is the use of two or more redundant degrees-of-freedom (as defined above) actuated in series, via an appropriate controller, one being a macro DOF and one being a micro DOF, for the purpose of reducing the effective inertia, as measured from the distal side of the macro-micro system (e.g., the side that interacts with the patient in an MIS system) to approximate that of the micro-freedom, while retaining the range of motion of the macro-freedom.

FIG. 23 depicts an example of a one DOF master-slave system, that illustrates the macro-micro concept, and upon which tests have been conducted.

The slave 400 has two degrees of freedom, a macro 401 and a micro 402 freedom. The master 403 has one degree of freedom. All three joints are driven by brushed D.C. servomotors (Maxon Motors RE025-055-035EAA200A) 411, 412 and 413. In the following discussion of the system, all joint forces and positions are scaled by link lengths implicitly, in order to avoid carrying these values through the calculations. Joint forces and positions are labeled $\tau_1$ and $q_1$ respectively, and have units of newtons and meters. Inertias are also measured at the endpoint of each joint and have units of kilograms.

The first joint position of the link 407 of the slave 400 is labeled $q_1$ and the output force for this joint (force at the tip of the link (i.e., the intersection of shafts 4040 and 406) is $\tau_1$. This first joint is driven by a low friction, one stage cable reduction with a ratio of 13.87:1. The joint one encoder 409 is a Hewlett-Packard optical encoder with 2000 counts per revolution after quadrature. The output resolution is therefore 27,740 counts per revolution. At a link length of $l_1$=0.0635 m (2.5 in), this gives an endpoint resolution of $1.44 \times 10^{-5}$ m ($5.66 \times 10^{-4}$ in).

The second joint 2 is mounted to the link 407 of the first joint 1 such that the joint 2 axis $A_2$ is orthogonal to and intersecting with the axis $A_1$ of joint 1. The second joint position is labeled $q_2$, and the output force of this second joint is labeled $\tau_2$. Mounted to the shaft 404 of the joint 2 motor is a "T" shaped output end effector link 406. The second joint is direct drive and uses a Canon laser encoder (TR-36) 414 with 14,400 counts per revolution after quadrature. At a link length of $l_2$=0.025 m (1 in), this gives an endpoint resolution of $1.11 \times 10^{-5}$ m ($4.36 \times 10^{-4}$ in).

The master 403 is a single rotary joint whose position at a master reference point, such as the user handle 408 is labeled $q_3$. The force for this master joint is $\tau_3$. The master 403 is driven by a single stage cable reduction with a ratio of 10.67:1. The encoder 416 on this axis is a Hewlett-Packard optical encoder with 2000 counts per revolution after quadrature, giving a total resolution of 21,340 counts per revolution. At a link length (the point 408 where the user holds the master) of $l_3$=0.044 m (1.75 in), this gives an endpoint resolution of $1.29 \times 10^{-5}$ m ($5.1 \times 10^{-4}$ in).

The inertia for joint 1, the macro axis, is 1.16 kg. The inertia of joint 2, the micro, is 0.006 kg, and the inertia for joint 3, the master, is 1.53 kg. The friction in each axis was measured using a digital force sensor. The friction in joint 1, the macro, is approximately 0.47 N; the friction in joint 2, the micro, is 0.02 N; and the friction in joint 3, the master, is 0.54 N.

Torques are calculated based on control laws and are commanded from a computer (Dell P.C., 166 MHz Pentium Processor) to 12-bit D/A boards (SensAble Technologies, Inc., Cambridge, Mass.) which in turn command analog voltages to PWM servo amplifiers, (Model 303, Copley Controls, Westwood, Mass.). The servo loops ran at approximately 6000-Hz for the data discussed regarding this test device. Encoder counters are mounted on the same board as the D/A converters.

To understand the qualitative effect of macro-micro control, consider that a small external force is applied to one end of the end effector link 406 of the micro actuator 404 by its environment, e.g., it encounters a fixed object. Because the micro actuator 402 has low inertia, and presumably also low friction, it will deflect relative to the macro actuator 401 with little resistance. This motion will be tracked by the master actuator 403, i.e., it will move to replicate it. If the user is holding the master actuator at 408, he will feel a force, and the sensitivity with which he will feel forces increases as the inertia and friction of the micro actuator 402 decreases. The utility of coupling the macro actuator to the micro actuator is that the macro actuator 401 applied to the micro actuator 402 increases the total range of motion of the slave 400. Since the micro actuator end effector link 406 can only move a short distance relative to the macro actuator link 407, the macro actuator 401 provides a moving base for the micro actuator 402, so that the combined slave system has both the sensitivity of the micro actuator 402 and the large range of motion of the macro actuator 401.

Jacobian Inverse Controller

A controller that suppresses the inertia of the macro actuator well is a Jacobian Inverse controller.

A one DOF version of a Jacobian Inverse controller is given as follows. (The subscripts are as above. 1 is the large, macro manipulator. 2 is the small, micro manipulator relative to the macro manipulator. 3 is the master. S is the slave tip relative to ground.) The master is commanded to move the master reference point to follow the position of the tip of the end effector link of the slave manipulator:

$$\tau_3 = -K_3(q_3 - x_s) - B_3(\dot{q}_3 - \dot{x}_s), \quad (26)$$

where $$x_s = q_1 + q_2. \quad (27)$$

The slave macro is commanded to follow the position of the master, without regard to the actual micro end effector link position:

$$\tau_1 = -K_1(q_1 - q_3) - B_1(\dot{q}_1 - \dot{q}_3). \quad (28)$$

In other words, the macro controller assumes that the slave micro end effector link at zero, relative to the macro. Finally, the micro actuator is commanded to keep the end effector link at zero:

$$\tau_2 = -K_2 q_2 - B_2 \dot{q}_2. \quad (29)$$

For the 1 DOF example, the gains are then tuned to provide as stiff a master and slave macro as possible and then the slave micro gains are tuned such that the total endpoint stiffness of the slave is the desired scale factor, for instance 50, times less than that of the master in order to provide scaled, e.g., 50:1, force reflection. Gains which provide this are:

$$K_1 = 7000 \text{ N/m}$$

$$K_2 = 163.74 \text{ N/m}$$

$$K_3 = 8000 \text{ N/m} \quad (30)$$

$$B_1 = 55 \text{ Ns/m}$$

$$B_2 = 1.331 \text{ Ns/m}.$$

$$B_3 = 65 \text{ Ns/m} \quad (31)$$

The macro and micro stiffnesses $k_1$ and $k_2$ form springs in series, so that:

$$(163.74 \times 7000)/(7000 + 163.74) = 160 \text{ N/m} \quad (32)$$

The micro axis is decoupled from the macro axis. Regardless of the position of the master reference point or macro axes, the micro joint simply tries to keep the end effector link at its zero position.

A freespace step response test for this Jacobian Inverse controller shows good results. The master and macro respond to each other and come together in straightforward second order responses. Since the inertia and gains of these axes are similar, they essentially mirror each other's motions. The micro axis barely moves during the motion. The response appears well behaved and stable.

A contact response test for this Jacobian Inverse controller also shows good results. Initially the master and slave move together, with the slave moving towards an aluminum block. The slave hits the block and its end effector tip position comes immediately to rest. The master actuator reference point overshoots the slave end effector tip position due to the masters finite servo stiffness, but quickly comes to rest. The slave macro (base) comes to rest at the position of the master, assuming the end effector to be at zero. A roughly 0.25 mm offset between the master and slave represents a constant force being applied to the user. A difference in curves for the slave and the base represent the relative motion between the micro and macro motions. While the micro stays in contact with the block, it deflects relative to the macro actuator.

This controller is well-behaved during contact and provides crisp feeling scaled force reflection. During freespace motions and during contact, the feel is very similar to that of a basic teleoperator that has only a micro actuator. It has the important advantage however that the range of motion is equal to that of the macro actuator.

Regarding the inertia that the user feels when the system is moved through freespace, the user feels the inertia of the slave macro freedom multiplied by 8/7. Examination of equations 26 and 27, and considering that in freespace motion, there is no disturbance applied to $q_s$, then $q_s=0$. These equations are then identical to those for a basic teleoperator, that does not have the macro-micro feature. However, the gain scale is 8000/7000, so that if one could increase the gain of the macro freedom further, the macro freedom would feel lighter. So using this macro-micro approach, while moving through freespace, the user feels the inertia of the master, 1.53 kg, plus 8/7 times the inertia of the macro base, or 1.33 kg. Had only the macro base been used as the slave and implemented 50:1 force scaling, a slave inertia of 50 times its actual inertia, or 58.7 kg would have been felt.

Extension to Higher Degrees of Freedom

The 1 DOF Jacobian Inverse controller just discussed can be extended to a higher number of degrees of freedom. The general equations are given below.

The translation of a reference point on an end effector link of the wrist kinematically after all of the joints (except for joint 7, which only actuates gripping) for instance the tip of the jaw 318*a*, has only three possible translational degrees of freedom. Translation of this reference point is redundantly controlled by motion of the combination of the base joints and the wrist joints. For each of the three axes of translation of the tip of the jaw 318*a*, a plurality of actuators contribute to translation of the point along that axis. For each such axis of translation under macro-micro control, there is at least one micro joint and at least one macro joint distinct from the micro joint. In the embodiment of the invention shown in FIG. 2, the joints 0, 1, and 2, constitute the macro actuator joints and the joints 3, 4, 5, 6 and 7 constitute the micro actuator joints.

Taking for instance actuation in the z direction, the joints 0, 1 and 2 can all constitute a macro actuator, depending on where in its workspace the end effector is located. Similarly, the joints 3, 4, 5, 6 and 7 could all constitute micro actuators.

Controlling the RDOF Slave with a 7 DOF Master

It is possible to control a slave having a number of DOFs X with a master that is characterized by a number of DOFs Y, where Y is less than X. For instance, in the embodiment discussed above, the slave unit linkage is characterized by eight DOFs (seven DOFs of the end effector finger 318*a*, plus gripping) and the master unit is characterized by seven DOFs (six DOFs of the master reference member 376*a*, plus gripping). Extending the single DOF macro-micro concept and Jacobian Inverse Controller to a higher number of DOFs, as provided by the present invention, requires the consideration of several items.

There is significant coupling among the various DOFs. In particular, it is not possible to associate individual motors as macro-micro pairs.

The wrist mechanism, which provides the micro axes, is also used to control orientation. This dual role implies that (a) the designer must trade off orientation tracking between master and slave with the macro-micro feature, and (b) that torque feedback can not be provided to the master (the torque signals are effectively used by the macro-micro to enhance force feedback). Fortunately, many tasks, such as MIS tasks, can tolerate considerable orientation errors. Also torque feedback is not helpful as contacts are typically single-point and dominated by forces.

To provide three macro-micro axes, the wrist design of the invention shown in FIG. 12 uses two sequential pitch axes, leading to 8 DOFs. This implies a single degree of redundancy with respect to position, orientation and grip of the slave, which the 7 DOF master can not control. Instead it must be controlled automatically.

The following controller design, which will be understood with reference to FIG. 22B provides the full DOF extension and addresses the above items. Some of the following operations are omitted from FIG. 22B for simplicity.

The master tip position $x_m$, tip orientation $R_m$ (measured as a rotation matrix), translational velocity $\dot{x}_m$, and angular velocity $\omega_m$, are scaled and offset 502 before becoming slave commands. (The rotation operations are not shown in FIG. 22B.)

$$x_{sd} = (x_m + x_{offset})/\text{scale} \tag{33}$$

$$\dot{x}_{sd} = \dot{x}_m/\text{scale} \tag{34}$$

$$R_{sd} = R_m R_{offset} \tag{35}$$

$$\omega_{sd} = \omega_m \tag{36}$$

The slave actual $R_s$ and desired $R_{sd}$ rotation matrices are converted into an angular error vector $e_s$.

$$R_s = R_{sd}^T R_s \tag{37}$$

$$e_s = \frac{1}{2} R_s \begin{bmatrix} R_{s32} - R_{s23} \\ R_{s13} - R_{s31} \\ R_{s21} - R_{s12} \end{bmatrix}. \tag{38}$$

A slave tip reference velocity $\dot{x}_{sr}$ (6 dimensional) is defined to include both translation and orientation.

$$\dot{x}_{sr} = \begin{bmatrix} \dot{x}_{sd} \\ \omega_{sd} \end{bmatrix} - \lambda \begin{bmatrix} x_s - x_{sd} \\ e_{sd} \end{bmatrix}. \tag{39}$$

This incorporates 508 any position errors into the velocity command in a stable fashion, so the Jacobian inversion 504 given below can operate entirely in velocity space. A separate position command is no longer needed (for the inversion process). For example, a system lagging behind will see a higher velocity command and catch up, whereas a system that is ahead will see a slower velocity command. The bandwidth λ controls 510 this position feedback and should be selected to roughly match the overall system bandwidth.

This Cartesian (tip) reference velocity is converted into joint space 504 through the Jacobian inverse.

$$\dot{q}_{sr} = J(q_s)^{-1} \dot{x}_{sr}, \qquad (40)$$

where $J(q_s)$ is the Jacobian of the slave manipulator relating the joint velocities to tip velocities at the given joint configuration. This is computed via standard robotics tools. Note the tip velocity is assumed to be six dimensional, including translation and orientation.

The Jacobian inverse is computed via a numerical SVD (singular value decomposition).

The joint reference velocity is then decomposed 512 into a desired joint velocity $\dot{q}_{sd} q_{1d}$ and desired joint position $q_{sd}$.

$$\dot{q}_{sd} = \dot{q}_{sr} + \lambda(q_s - q_{sd}) + q_{null}\alpha \qquad (41)$$

$$q_{sd} = \int \dot{q}_{sd} dt. \qquad (42)$$

This undoes the combination of 508 above and allows the subsequent P.D. controller 514 to operate on position and velocity separately as is standard. (A single signal line is shown in FIG. 22B coming into the P.D. controller 514, for both $\dot{q}_{sd}$ and $q_{sd}$. However, this is for simplicity only in the figure. In fact, they are operated upon separately.)

The null-space vector $q_{null}$ 516 (the combination of joint moves that does not cause any tip translation) of the slave at the current joint configuration may be computed during the SVD routine mentioned above.

Scaling and adding 520 the null-space vector to the desired velocity provides control of the slave arm within the redundant DOF. The magnitude value α determines the speed of motion inside this null space and is selected to minimize a cost function $C(q)$. It is also limited 518 to prevent undesirably fast motions.

$$\alpha = -sat(q_{null}^T \frac{\partial C(q)}{\partial q}, \alpha_{max}) \qquad (43)$$

A quadratic function with a diagonal weighting matrix W, is used, though any other cost function is also 5 acceptable.

$$C(q) = \frac{1}{2}(q_5 - q_4 - q_c). \qquad (44)$$

This quadratic function is minimized when $(q_5 - q_4 - q_c)$ equals zero. For instance, FIG. 14 shows this cost function minimized when $q_c$ is zero. Beneficial results have also been achieved setting $q_c$ equal to 0.4 and W=20.

The desired grip position and velocity are appended, which are fed directly from the master grip, to the above computed desired joint position and velocity. The desired joint positions can also be limited to restrict the mechanism motion to within some desired region.

A joint torque $\tau_s$ is determined (with standard gravity compensation 516) and applied to the slave mechanism 520 according to a P.D. controller 514

$$\tau_s = -K_s(q_s - q_{sd}) - B_s(\dot{q}_s - \dot{q}_{sd}). \qquad (45)$$

The gains $K_s$ and $B_s$ have to be positive definite with diagonal gains selected for simplicity.

The gains of this controller are determined to provide good behavior of each joint. Therefore, for the large inertia macro (base) joints, the gains are high. For the small inertia micro (wrist) joints, the gains are low. The bandwidth and damping ratio of each joint should be roughly identical.

To provide feedback to the master 522, of interactions between the slave 520 and its environment 524, the slave actual tip position and velocity are scaled and offset 526 inversely from the scale and offset of the master reference position and velocity at step 502.

$$x_{md} = scale \cdot x_s - x_{offset} \qquad (46)$$

$$\dot{x}_{md} = scale \cdot \dot{x}_s. \qquad (47)$$

The master torques are computed (with gravity compensation 528) via a Jacobian transpose and Cartesian P.D. (tip) gains 532:

$$\tau_m = J(q_m)^T(-K_m(x_m - x_{md}) - B_m(\dot{x}_m - \dot{x}_{md})) \qquad (48)$$

The exact macro-micro behavior is determined by the gain selection. Disturbances at the endpoint (tip) of the slave effector 520 cause deflection of the low-gain/lowweight wrist axes. This is sensed and reflected to the master 522. Should the user 534 accommodate this feedback And allow the master 522 to deflect, the slave base joints will be commanded to move also. Thereby allowing a small disturbance to move the heavy base and completing the macro-micro concept. The macro-micro behavior discussed above is achieved by setting the gains for the micro joints in the slave joint P.D. controller 514 to be relatively small as compared to the gains for the macro joints, for example as shown above in Eq. 18.

The level of force amplification is determined by the relative gains between master and slave. The slave effector endpoint stiffness is dominated by the wrist axes and may be fairly low. The master reference point stiffness is typically higher, so that small disturbances at the slave appear amplified to the user.

Other candidates for control schemes, other than the Jacobian Inverse, are discussed below. These include a Modified Jacobian Inverse and a Simulated Force Sensor Controller.

Force Reflection

In this section force reflection for the Jacobian Inverse controller is discussed, as this gave good results. When implementing a master-slave teleoperator with force reflection, there are several qualities which describe the quality of force reflection:

Freespace motions of the system should feel free. The user who is operating the master should feel the master and little else. They should not feel as if they are "dragging" or "carrying" the slave along with them. If no forces from the slave are sent to the master (force reflection is turned off and the master is used only as a positioning input), then this will be the case.

Contact should feel like contact. Forces between the slave manipulator and its environment should be reproduced—at the master.

The system should be sensitive. The lowest level of force that can be felt should be as low a possible. How low depends on the task at hand. The ability to discriminate when contact occurs and how delicately contact occurs depends on this value.

Because the system is multi-dimensional, these properties should be equally good in all directions. There should not be preferential directions of motion caused by anisotropic friction or inertia because this may mislead the surgeon while they operate.

The foregoing discussion has focused on using the macro-micro control technique to control a slave, with a master. However, the macro-micro control is a good way of controlling forces between a manipulator and things that it contacts in its environment, regardless of whether the manipulator is controlled as a slave by a master.

Freespace Responses

Using the Jacobian Inverse Controller discussed above, an 8.0 rad/sec, 2 cm amplitude sinusoid was commanded to the slave of the invention shown in FIG. 1 as the desired motion and the resulting slave motion was recorded. (In other words, the slave was commanded by a virtual master.)

Also recorded was the force commanded to the master through the controller and the force measured (using slave motor commands (currents)) at the slave tip. The actual force at the slave tip is zero because the slave tip is not touching anything Freespace response in the x and y directions are quite similar to each other. There is a substantial amount of tracking error, which is presented as a force of roughly 1.5 N to the master. The diminished base tracking and diminished freespace performance is a result of lowering the base gains from a possible 3500 Nm/rad to 200 Nm/rad during these tests to achieve stability.

At a peak acceleration of 1.28 m/s², one would expect a force of:

$$0.77 \text{ kg} \times 1.28 \text{ m/s}^2 = 0.98 \text{ N}. \tag{49}$$

The 1.5 N force observed is not surprising, considering that only inertial forces are considered in the above analysis.

Figure 24A:
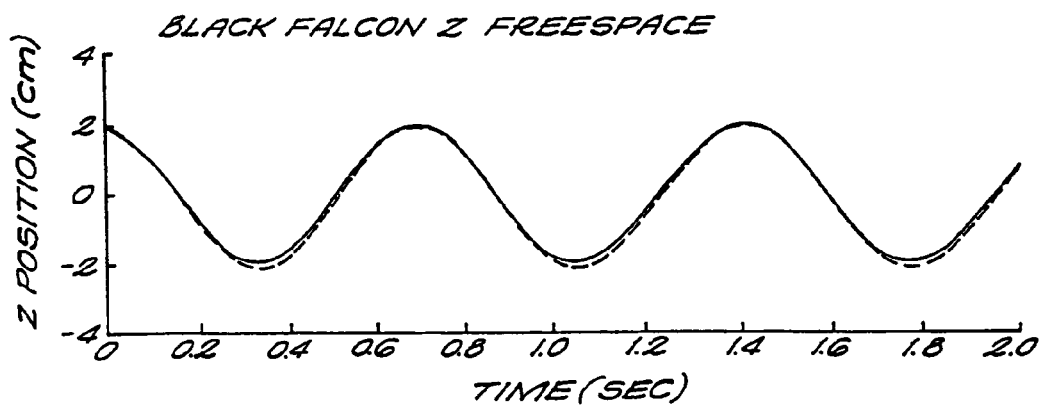
FIG. 24A is a graph showing the position along the z axis of the master and the slave in a freespace test of a macro-micro control scheme for the embodiment of the invention shown in FIG. 1, with the solid line representing the master and the dashed line representing the slave.
Figure 24B:
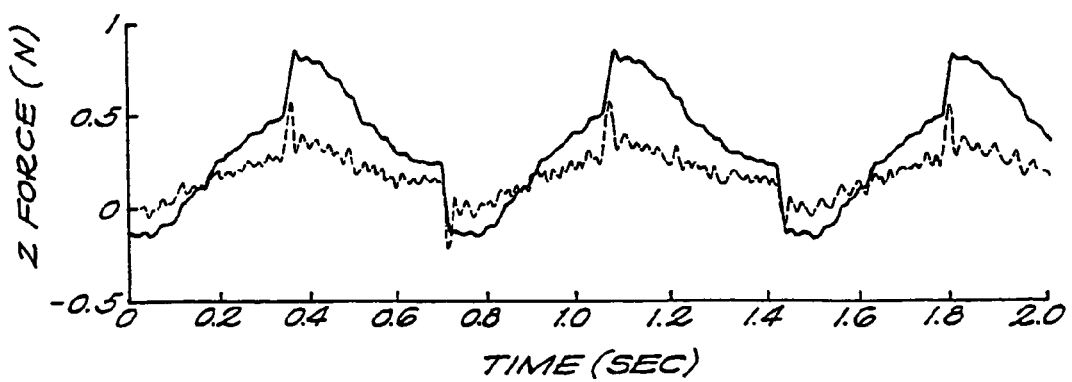
FIG. 24B is a graph showing the force at the master and the slave in the freespace test of a macro-micro control illustrated in FIG. 24A.

The z axis free space tracking performance is considerably better, as shown in FIG. 24A. (The solid line represents the master; the dashed line, the slave.) In absolute terms, the tracking error is less. This case differs from the x and y direction cases in that the error in the z axis is due to the micro axis more than the macro axis. The macro axis (joint 2) was running at a high (20,000 N/m) gain which, unlike in the joint 0 and 1, axes does not seem to cause vibration. This is likely because structural stiffness is higher in the z direction and the inertia being moved is considerably less.

Joint 4 acts as the micro axis during the z direction tests. It is coupled to joint 2 (through the cable drive) such that when the direction of motion of joint 2 changes, a force equivalent to the joint 2 backdrive friction is introduced to the joint 4 and hence the output. This explains a cyclic sharp rise and fall in the output error plot when the direction of motion changes.

Contact Responses

During contact experiments the PHANToM™ haptic interface is used as the master. The tests were made by moving the PHANToM™ master to control the slave such that the slave came into contact with a rigid aluminum block. Because the movement is done by hand, the tests are not entirely repeatable. But qualitatively, the responses look quite similar when the tests were run multiple times. A 2:1 force scaling was implemented.

Contact responses in the x and y directions look very similar. Fairly substantial freespace forces are shown, which one would expect from the results of the previous tests. The contact is however, quite good. A sharp force increases in both the master and the slave, which closely mimic each other. The steady state forces settle to 0.5 N (slave) and 1.0 N (master) showing the 2:1 force scaling which was implemented.

There is little overshoot seen in the measured slave tip position as it contacts the aluminum block. This means the estimate of the endpoint position using joint measurements is good and shows that there is relatively low structural flexibility.

Figure 25A:
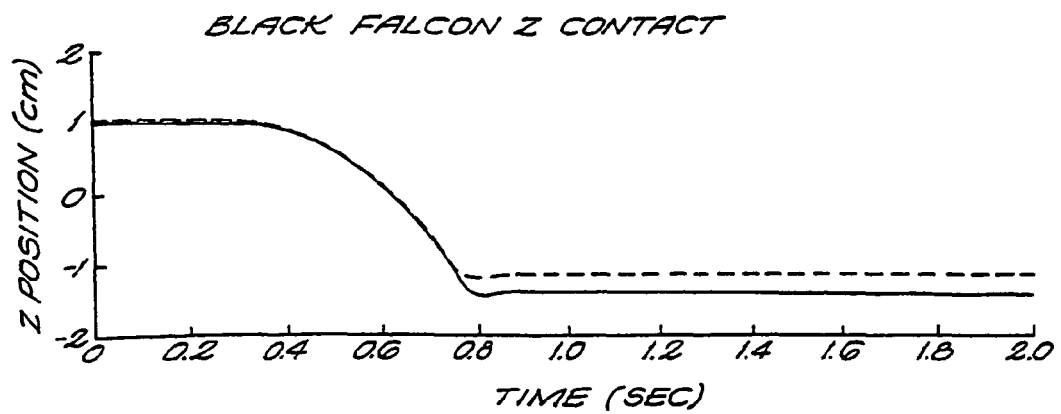
FIG. 25A is a graph showing the position along the z axis of the master and the slave in a contact test of a macro-micro control scheme for the embodiment of the invention shown in FIG. 1, with the solid line representing the master and the dashed line representing the slave.
Figure 25B:
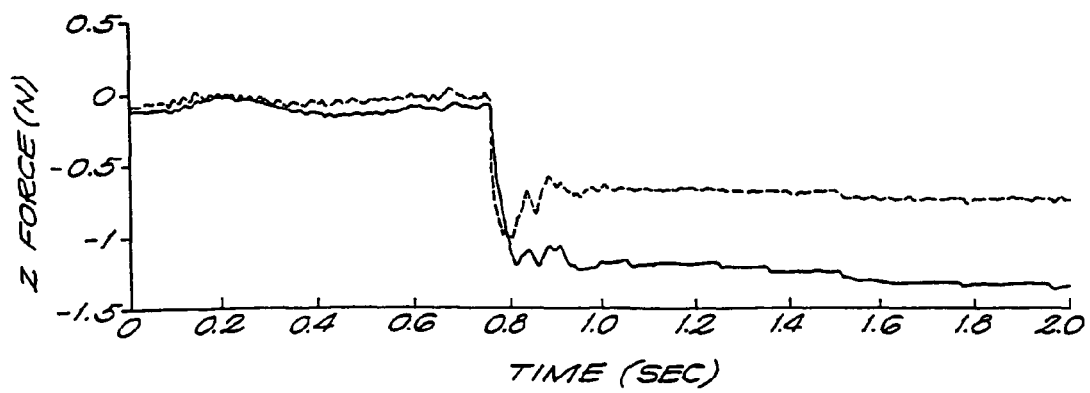
FIG. 25B is a graph showing the force at the master and the slave in the contact test of a macro-micro control illustrated in FIG. 25A.

The z direction contact is considerably better. This is in fact what one would want all the responses to look like, as shown in FIGS. 25A and 25B. The tracking performance, shown in FIG. 25A is excellent, as expected with a 20000 N/m joint 2 gain. The resulting freespace forces, shown in FIG. 25B, are nearly zero. Then, when contact is made, a very sharp increase in force occurs in both the master and the slave, which settles to a steady state value of 0.7 N in the slave and 1.4 N in the master as pressure is applied by the user.

This z axis is better than the others because the quality of each of the macro and micro freedoms involved is higher. The macro freedom, joint 2, has a backlash free transmission, is lightweight, and has excellent encoder resolution because four encoder signals are averaged in determining its position. A gain of 20000 N/m means that inertia is suppressed by a factor of 20000/480=41.7. The joint 2 inertia is only 3.35 kg, so that the user only feels 0.08 kg from the macro joint. If the inertia of axes 0 and 1 could be reduced, the overall performance of the system might be improved.

Discrimination Tests

The lowest level of force that a user could discriminate correlates well with the wrist backdrive friction levels.

Representative System Test Tasks

Two tasks have been accomplished which show different aspects of the system. The first task was suturing. Suturing is primarily a geometric task. That is, success depends on whether the system has sufficient degrees of freedom, workspace, and the appropriate kinematics to make the required motions.

The second test was a tube and wire test, where a piece of clear plastic tubing was pushed along a wire bent into 'S' shaped curves. This task requires similar mobility to suturing, but also requires contact with a much stiffer environment, namely a rigid metal wire. As a result, force reflection becomes much more important because small motions can create large forces that are difficult to detect visually.

For the force reflection tests described above, a PHANToM™ Haptic interface was used as a master. In order to perform these tasks and to use motion scaling, a larger master workspace was more convenient. Therefore, to demonstrate tasks such as suturing with motion scaling, a larger version of a PHANToM brand Haptic interface was used, known as the Toolhandle (described by Zilles, C. 1995 HAPTIC RENDERING WITH THE TOOLHANDLE HAPTIC INTERFACE, Master's Thesis, Dept. of Mechanical Engineering, Massachusetts Institute of Technology). The Toolhandle is essentially a scaled up PHANTOM with 16 in. (40.6 cm.) link lengths instead of 5.5 in. (14 cm.) link lengths.

Suturing

To demonstrate the ability to suture along arbitrary suture lines, stitches were made in muscle tissue of an uncooked skinless chicken leg. An Ethicon Ethibond polyester suture (3-0) was used with a curved, tapered SH needle. A row of stitches could be made along different lines relative to the instrument shaft. For example, one could suture along a line parallel with the instrument shaft, as can be done with difficulty (by some surgeons) using conventional MIS instruments.

Suturing was tried both with and without force reflection. With the system shown in FIG. 1, as described above, it was found that force reflection is not always a help. If freespace motions do not feel free enough, (for instance due to too much friction in the system) then background forces cause fatigue during fine motions required for suturing. Thus, the designer should consider reduction of any such background forces.

A second reason that force reflection is not always beneficial is that there is a sufficient deadband in the forces that can be felt. Most forces that are applied in suturing simply cannot be felt. Based on discrimination tests, forces below roughly 0.39 N to 0.58 N cannot be felt by a person using the device. To give an idea of how soft the tissue is, it was depressed with a force sensor (Mark 10 model BG) with a cone shaped attachment with a 60\deg included angle. To depress the cone approximately 6 mm required from 0.22 N to 0.6 N. Since one can easily see deflections of less than 1 mm, one will see deflections and hence infer forces being applied, long before one can feel them with this device.

Another way of stating this is that humans can already do this task (of knowing when and how much contact has been made) fairly well visually. Whether or not very good force reflection is necessary for suturing is questionable. It is unclear whether or not vision or touch is more important during the suturing task even when performed during open surgery.

Motion scaling used to reduce motions at the slave relative to the motions at the master makes fine slave motions easier, but reduces the environment compliance sensed by the user. It is already difficult to sense contact with soft tissue due to its low compliance. With any further decreased compliance, due to motion scaling, sensing contact would be essentially impossible. To compensate, one can implement force scaling, which increases the compliance sensed by the user. However, some of the task forces are fairly large. For example, it can take as much as one or two lbs of force (4.4 N-8.8 N) to push our needle through tissue. A similar amount of force might be used to draw a suture tightly. These forces, when scaled up-by a-factor of two, require two hands to apply while simultaneously controlling three positions, three orientations, and a gripper. It is convenient to use the left hand to support the end of the master while using the right hand to control fine motions. Therefore, if force scaling is used to achieve satisfactory levels of compliance, operation of the system as described above is difficult with one hand and certainly operator fatigue arises.

Tube and Wire Test

Another qualitative demonstration is a task where a plastic (tygon) tube is slid over a curved wire that is mounted in a small piece of wood. The tube could be slid along easily when using bare fingers. This task is somewhat more difficult to accomplish using the invention than suturing, for several reasons. The required range of wrist motion is greater. The contact between the instrument and the wire is stiff. This means large forces can be generated which cannot be resolved using visual feedback. Force reflection is therefore more important during this task than during the suturing task. Substantial torques can be applied to the wire through the gripper. However the system provides no torque feedback. Again large forces can be applied to the stiff contact without the user knowing. The grip force must be continuously modulated to successfully complete the task. With force reflection off, a test subject could perform this task. However, it was necessary to watch the instrument very carefully for deflections in the instrument in order to determine binding between the tubing and the wire.

With force reflection on, when the tube binds, forces are fed back, which stop the master from moving, so it becomes clear that the tube is stuck. However, because there is no torque feedback to tell the user which way to reorient the wrist to free the tube, one could only watch very carefully and jiggle the tube in order to free it.

Given these observations on mobility and force feedback, for many applications, it would be beneficial to use the first wrist pitch (joint 4) of the five DOF wrist primarily to avoid singularities, rather than to achieve force reflection under macro-micro control. This would help insure that an output roll was always available, which is critical during suturing, while force reflection is not. However, for tasks other than suturing, and tube sliding, and for applications other than MIS, force feedback may be very useful.

Mechanical Design Considerations

Base Unit

While each link of the base unit 302 described above was designed to be very stiff, the bearings that connect them were not as stiff as might be desired. The lowest structural natural frequency could be raised by increasing rigidity. Larger bearings, appropriately preloaded, would increase the overall stiffness. The spindle and Link 0 base bracket 308 pieces could also be provided with increased rigidity. The spindle should be stiff to resist torsional deflections about the x axis. A redesign where the base motors (axes 0 and 1) use two stage cable reductions instead of a single stage cable reduction and a gearhead reduction may provide good results. The gearhead backlash may be contributing to an inability to raise base gains further during force reflecting master-slave operation.

Wrist Unit

The wrist unit would perform some tasks better if it were, in general, stronger than described above. The full actuator potential of the base can not be used with the wrist described, partially because it is undesirable to pretension the wrist more, due to the limited strength of the wrist unit and the Spectra™ plastic cable used. More pretension would require stainless steel, or better yet, tungsten wrist cable. Metal cable however, tends to preclude a non-alpha wrist design, due to the extra friction created by alpha wraps when used with metallic cable. That would lead, then, to a bulkier wrist. It is critical that friction in the wrist be reduced if macro-micro type controllers are to be used for implementing force reflection. Thus, the designer must balance these considerations depending on the desired application.

Master

A few comments are warranted on the design of master manipulators for minimally invasive surgery, and in particular on the suitability of a haptic interface similar to the PHANToM™ master for this purpose. In general, the PHANToM™ master is very good. It is a three-degree-of-freedom arm which is nearly counterbalanced mechanically (the remainder can be done in software using motor torques) and which has low friction and no backlash in the transmissions. There are several areas to modify this device when used as a master manipulator with the slave of the invention. To have similar encoder resolution to the slave, resolution should be increased by roughly 100 times. This would give the slave a much smoother command to track. This would allow higher base gains to be implemented to improve both tracking and force reflection performance. Continuous force levels should be increased by about 10-20 times to allow scaled force reflecting teleoperation. The structural stiffness of the master is low and could easily be increased by several times through modified design, especially through bearing design at the joints.

A master wrist with more DOFs may also be desirable. While using the system, one often runs into rotational limits of the master well before running into such limits on the slave. One solution is to use a kinematically identical master and slave, so that singularities and joint limits are aligned. However reorientation of the slave relative to the patient would then require reorientation of the master to keep this benefit. Another solution is to increase the range of motion of the master wrist, (i.e., the portion kinematically more distant from ground than the link $l_M2$) most likely through the use of a four DOF wrist, that is through the addition of an output roll. In order to take advantage of this however, the master gimbal must have at least one computer controlled, powered joint (most likely the input roll (closest to ground)) in order to ensure that singularities are avoided. There is another reason to power the master wrist joints when the device is used for MIS. When the surgeon lets go of the master (which happens frequently), the master wrist will simply fall. Even if it were balanced, one could bump it easily. The slave wrist will then track this motion, potentially causing damage to tissue. Assuming that sensors are incorporated to determine whether or not the surgeon is holding the master, then there are two options. First the master and slave can be disconnected in software, so that when the master wrist falls, the slave wrist does not move. In this case, re-engaging the system may present a problem. The surgeon would have to realign the two (with some sort of visual cues displayed on the video monitors for example) before the controller would re-engage the system. The second option is that the master gimbal is powered so that when the surgeon lets go, it simply freezes in position so that misalignment between the master and slave never occurs. Another advantage of this approach is that if the slave manipulator is manually repositioned with respect to the patient, the master manipulator can reposition and reorient itself automatically in order to maintain visual correspondence between the two.

A disadvantage to powering the master wrist is that it generates a substantial increase in design complexity and possibly weight. Finally, the designer may want to not only power the wrist, but design these degrees of freedom to allow precise application of forces in order to give the surgeon torque, as well as force, feedback.

Other Controller Candidates

The Jacobian Inverse controller discussed above worked well in the macro-micro context of the embodiment of the invention shown. However, other controller candidates were found to provide promising results, and should be considered for embodiments and applications different from that shown above.

Modified Jacobian Inverse

One controller may be considered to be a Modified Jacobian Inverse Controller. This method was originally developed to increase response times of a slow and/or flexible industrial manipulator by adding a small, high bandwidth micro manipulator to its end. See Sharon, A, Hogan, N. and Hart, D. The macro/micro manipulator: An improved architecture for robot control. Robotics and Computer Integrated Manufacturing, 10(3):209-222 (1993). The idea, which was used by for a single manipulator, to command the micro actuator to null error between the desired slave endpoint position and the actual slave endpoint position. If the micro actuator has a faster servo bandwidth than the macro actuator, then the micro actuator will tend to jump out ahead of the macro actuator and consequently decrease position response times. Its effect on a teleoperator system is discussed below.

The controller is given as follows. As in the Jacobian Inverse controller, the master desired position is that of the slave tip:

$$\tau_3 = -K_3(q_3-q_1-q_2) - B_3(\dot{q}_3 - \dot{q}_1 - \dot{q}_2) \quad (50)$$

Similarly, the macro desired position is equal to that of the master so that:

$$\tau_1 = -K_1(q_1-q_3) - B_1(\dot{q}_1 - \dot{q}_3) \quad (51)$$

In the Modified Jacobian Inverse method, the micro position is not servoed to zero, but rather directly to the master position:

$$\tau_2 = -K_2(q_2-q_3+q_1) - B_2(\dot{q}_2 - \dot{q}_3 + \dot{q}_1) \quad (52)$$

This is what gives the jump out ahead behavior to the micro axis.

A representative set of gains is:

$$K_1 = 7000 \text{ N/m} B_1 = 55 \text{ Ns/m}$$

$$K_2 = 160 \text{ N/m} B_2 = 1.3 \text{ Ns/m}.$$

$$K_2 = 8000 \text{ N/m} B_3 = 65 \text{ Ns/m} \quad (53)$$

Regarding both the step and contact response for this controller both exhibit significant oscillation. The micro initially jumps out ahead of the macro axis. The overall amount of oscillation is greater due to the added control input caused by the micro actuator. The overall speed of response is roughly 10 times slower than in the Jacobian Inverse control case.

The increase in the level of oscillation in the system and poor contact response make this method of control less desirable than the Inverse Jacobian control for MIS. However, for other applications, or for manipulators with different kinematics and dynamics, this controller may prove beneficial, and should be considered.

Simulated Force Sensor Controller

A known method to implement teleoperator force reflection is to use a force sensor on the end of the slave manipulator and to feed these forces directly back to the master. The master then tracks the endpoint position of the slave. It is possible to use the macro micro apparatus described above using the micro actuator as a force sensor. In this case, the micro actuator is commanded to remain at zero:

$$\tau_2 = -K_2 q_2. \quad (54)$$

This force is fed back to the master with a 50 times force scaling:

$$\tau_3 = -50\tau_2. \quad (55)$$

The macro is commanded to track the master:

$$\tau_1 = -K_1(q_1-q_2) - B_1(\dot{q}_1 - \dot{q}_2). \quad (56)$$

The gains were:

$K_1 = 7000$ N/m $B_1 = 55$ Ns/m $K_2 = 163.74$ N/m $B_2 = 1.331$ Ns/m (57)

In a free space test, because there is no contact being made with the micro actuator, no forces are commanded to the master. The micro also does not move relative to the macro. The macro compensates entirely on its own and eventually reaches the master position in a classic second order response. In a contact test, when contacting a rigid surface, the slave displays a contact instability. Because the scaled contact force is fed directly back to the master, the master is forced backwards away from the contact block. The macro axis tracks this motion and pulls the entire slave away from the aluminum block at which point the force commanded to the master drops to zero. But the user is still pushing the master towards the block, so the micro re-initiates contact. A violent increase in the amplitude of the oscillations occurs.

As with the Modified Jacobian Inverse method, the behavior mentioned above make this method of control less desirable than the Inverse Jacobian control for MIS. However, for other applications, or for manipulators with different kinematics and dynamics, this controller may prove beneficial, and should be considered.

Improved Force Reflection

If the quality of force reflection needs to be improved, one option is to further improve the transmission characteristics of the slave, primarily to reduce friction. Brushless motor technology, which typically has had many problems when applied to force control, may have improved sufficiently to be of use.

Features

With a teleoperator master placed in the loop in addition to the slave, several features are possible. A few basic results are discussed below.

Alignment of Visual Image With Hand Motions

A basic feature is to orient the visual image of the surgical site and slave tip motions with those of the surgeon's hand and master manipulator. If the surgeon were directly viewing the operating site, master and slave motions could coincide in an absolute reference frame. But if the slave is viewed on a monitor, the reference frame of the slave must be rotated such that it coincides with the viewing direction of the camera. The reference frame of the master is rotated such that it coincides with the reference frame of the monitor. Then a motion of the master directly towards the monitor, for example, will be a motion of the slave directly away from the camera and the image of the instrument tip on the monitor will coincide with motions of the master manipulator. In this way, motions made by the surgeon coincide with those that appear on the monitor.

Having high resolution 3-D vision is also important. Humans rely on vision and without it, are at a loss. While this is not a focus of this invention, it will be important in a fully functional system for human surgery.

It is also possible to project a stereo image of the surgical site to the surgeon using a mirror. The system must be aligned very carefully such that the slave instrument tips appear (in the mirror) to extend from the tools that the user is actually holding with their hands, which are partially visible from outside the sides of the mirror. This creates a powerful illusion.

Visual Overlays

Visual overlays can be included into the surgeon's monitor view of the operating site. Since this view is already planned to be in 3D, it is possible to have images, MRI images of tumors for example, directly overlaid onto this view.

Motion Scaling

Motion scaling can be implemented as discussed above. The slave is commanded to track scaled versions of the master motions. Rotational motions are not scaled. It is typically desirable to allow large master motions to correspond to small slave motions, as this makes the slave more steady, in that jerky master movements are made smaller and less noticeable. It also effectively increases the position resolution of the master. Motion scaling ranging from 1:1 to 5:1 have been used. The value to choose is task dependent. 5:1 might work well when the surgeon is performing ½ inch slave motions, but is inconvenient if making 2 inch slave motions. For suturing, 2:1 motion scaling works well.

Indexing

Indexing is decoupling the master from the slave (via the controller), to reposition the master within its workspace. Indexing is analogous to lifting a computer mouse from its pad (decoupling it from the cursor) and moving it back to the center of the mouse pad. This is straightforward to implement, and logical for positions. It does not make help to index orientations, because if master and slave orientations become misaligned, it becomes very difficult for the surgeon to determine how master motions correspond to slave motions. Position indexing is especially helpful when large motion scaling factors are used. Position indexing can be activated by pressing a mechanical switch, by voice activation command that is communicated to the controller, or by any other suitable means.

Heptic Overlays

Haptic overlays can also be provided onto the workspace of the master manipulator. The designer can place walls or funnels within the workspace in order to guide the surgeon or to protect sensitive areas from accidental contact. The designer must take care with both the visual and haptic overlays to accurately register the information to the actual anatomy. Displaying the information is relatively simple.

Beating Heart Surgery

Another enhanced mode of surgery is operating on moving tissue, e.g., operating on a beating heart, to avoid the need for a heart lung machine and the trauma and risk associated with circulating blood through it. The motion of the heart can be measured, and then the slave can track this motion. In the reference frame of the slave, the heart is thus still. The same thing can be done to the image of the heart, either by having the arm which holds a camera track the heart motion, or by nulling out motions in the image using the measured position of the heart. Then the illusion can be created for the surgeon that the heart is still, when it is in fact beating.

Figure 26:
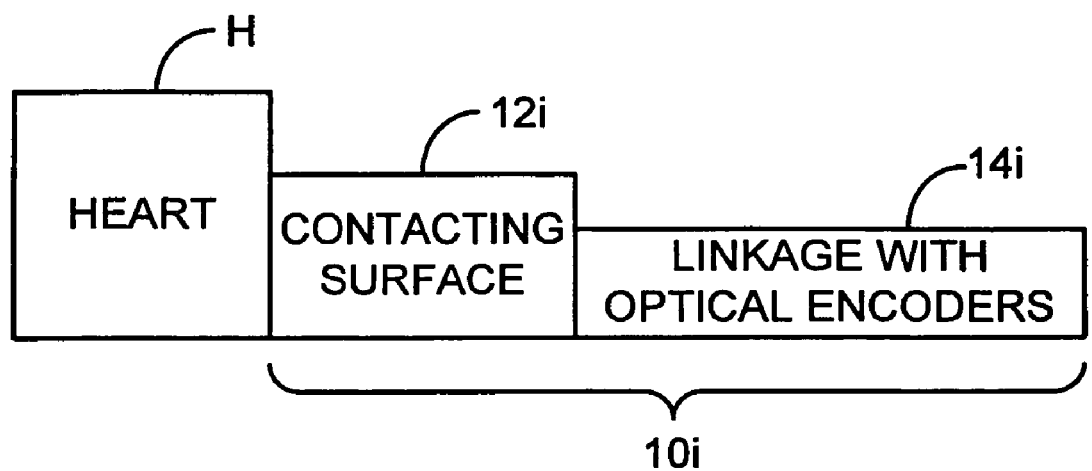
FIG. 26 is a schematic representation of a system for tracking a beating heart according to the present disclosure.

Care must be taken in measuring where the heart is. For the slave to track this, information must be provided at least at servo rates, and preferably at better than servo rates, so that noisy data may be filtered. It is necessary then to determine six DOF motion at, e.g., 2000 Hz. It will be difficult, if not impossible, to do this using a video image, which typically supplies information at 30 or 60 Hz. One possibility is to use a small instrumented mechanical arm 10$i$, as shown in FIG. 26, whose end 12$i$ (a small horseshoe shaped platform for example) is placed directly onto the heart H. A serial or parallel linkage 14$i$ with optical encoders mounted at the joints could measure six DOF motion at sampling rates in the kHz range. This arm would then measure the heart's motions precisely, at rates limited only by computational speed.

CONCLUSIONS

There are several problems in current MIS. The surgeon is deprived of three-dimensional depth cues and must learn the appropriate geometrical transformations to properly correlatA hand motions to tool tip motions. The surgeon's ability to orient the instrument tip is reduced. The incision point/cannula restricts the motions of the instrument from six DOF to four because it must enter through a point and be along a line from that point. As a result, the surgeon can no longer approach tissue from an arbitrary spot and angle and is often forced to use secondary instruments to manipulate the tissue in order to access it properly or to use additional incision sites. Suturing becomes particularly difficult. The surgeon's ability to feel the instrument/tissue interaction is nearly eliminated. The present invention is based on the premise that despite surgeons' considerable skill and ability to work within the constraints of current MIS technology, the expansion of minimally invasive medical practice remains limited by the lack of dexterity with which surgeons can operate while using current MIS instruments.

A teleoperator slave of this invention has been described. This eight-degree-of-freedom arm is structurally stiff and strong with high actuator capacity. The system is counterbalanced for safety by placing all of its actuators at its base and using cable transmissions to actuate the wrist and gripper. This also allows the wrist unit to be detachable to allow use of other wrist-units that perform other functions, such as cutting, grasping tissue instead of needles, and cauterizing. This basic concept also allows the portion of the instrument that enters the body to be sterilized. The wrist has enough degrees of freedom to allow macro-micro control in all three linear degrees of freedom, with the goal of allowing forces to be felt equally well in all three directions. A Jacobian Inverse Controller works well with the macro-micro slave. Also disclosed has been a method to implement such control using a master that has fewer degrees of freedom (joints) than has the slave.

The foregoing discussion should be understood as illustrative and should not be considered to be limiting in any sense. While this invention has been particularly shown and described with references to preferred embodiments thereof, it will be understood by those skilled in the art that various changes in form and details may be made therein without departing from the spirit and scope of the invention as defined by the claims.

For instance, the transmissions in both the base and the end effector of the slave have been described as predominately cable systems. However, these systems may be gear, pneumatic, belt or any combination thereof. For instance, it might be beneficial to include a rigid member in the transmission at the locus of connection between the transmission of the base and the transmission of the end-effector, thereby facilitating a quick release connection.

The actuators have been described as electric motors. However they can be any suitable actuators, such as hydraulic, pneumatic, magnetic, etc. In such a case, rather than measuring the motor current to determine its torque, the appropriate through variable is measured—e.g.—current for a motor, fluid flow for a fluid actuator, etc.

Further, as described, six joints (2-7) are included in the removable wrist unit. However, it would be possible to transfer one or more of these joints to the base unit, thereby requiring fewer moving parts in the interchangeable end-effector. For instance, translation along and rotation around the long axes 2 and 3, respectively, could be achieved using a transmission that is part of the base unit 302, rather than the end effector 304. This would limit, somewhat, adaptability, for instance in changing the instrument's stroke. However, it would also simplify and lighten the wrist unit 304.

What is claimed is:

1. A robotic surgical system, comprising: a slave articulate arm having a plurality of linkages and joints and a distal portion; and
    a slave surgical instrument releasably coupleable to said distal portion of said articulate arm, said instrument comprising a wrist portion and at least a first end effector element coupled to the wrist portion, and a proximal portion coupled to an elongate shaft, said elongate shaft having a longitudinal axis and a distal end coupled to said wrist portion, said wrist portion of said instrument comprising:
    at least three distal axes of rotation relative to said distal end of said shaft, each of said axes offset from one another, at least two of said axes of rotation being substantially parallel to one another, said end effector element movable about the most distal of said three distal axes.

2. The system of claim 1, wherein said two substantially parallel distal axes do not comprise said most distal axis.

3. The system of claim 1, wherein said wrist portion comprises a fourth distal axis, two of said four distal axes of rotation being substantially parallel to one another, said other two distal axes of rotation being substantially orthogonal to said parallel axes, said end effector element movable about the most distal of said four axes.

4. The system of claim 3, wherein the most proximal of said four distal axes comprises an axis substantially coincident with the longitudinal axis of said instrument elongate shaft around which the wrist portion can rotate.

5. The system of claim 3, wherein the two substantially parallel distal axes are adjacent one another and are substantially orthogonal to said longitudinal axis of said instrument and said most distal axis.

6. The system of claim 3, wherein said articulate arm comprises a remote center of motion mechanism having degrees of freedom of movement that are redundant with the degrees of freedom of movement of the instrument around said first, second and third distal joint axes.

7. The system of claim 3, further comprising a master controller having an input linkage, wherein input commands from an operator to said input linkage cause the controller to control movement of said instrument according to said input commands.

8. The system of claim 1, further comprising:
    a master unit having a movable master, the slave articulate arm moving the end effector in response to movement of the master;
    a controller coupling the master unit to the slave unit so that an operator manipulating the master can direct the end effector in performing a surgical procedure on a target; and
    means for stabilizing an image of the target.

9. The system of claim 8, further comprising a camera arm that moves in response to the frame of reference of the target.

10. The system of claim 8, wherein the slave articulate arm moves the end effector in response to the frame of reference of the target, such that the end effector appears substantially motionless relative to a moving portion of the target.

11. The system of claim 8, wherein said sensor comprises a mechanical arm with an end that is placed against the target while the end effector performs the surgical procedure.

12. The system of claim 1, said wrist portion of said instrument comprising:
 a first distal joint coupled to said distal end of said elongate shaft, said first distal joint having a first joint axis substantially perpendicular to said longitudinal axis,
 a first distal link movably coupled to said first distal joint,
 a second distal joint coupled to said first distal joint via said first distal link, said second distal joint having a second joint axis substantially parallel to said first joint axis,
 a second distal link movably coupled to said second distal joint, and
 a third distal joint coupled to said second distal joint via said second distal link, said third distal joint movably coupled to said at least one end effector element; the system further comprising:
 a master controller having an input linkage, wherein input commands from an operator to said input linkage cause the controller to control movement of said instrument according to said input commands.

13. The system of claim 12, wherein said third distal joint has a third joint axis substantially perpendicular to said longitudinal axis of said elongate shaft, said third joint axis further substantially perpendicular to said first and second joint axes.

14. The system of claim 1, wherein said wrist portion is coupled to said elongate shaft in such a way that said wrist portion is movable about said longitudinal axis of said elongate shaft of said instrument.

15. The system of claim 1, wherein said elongate shaft is movable about its longitudinal axis.

16. The system of claim 12, said instrument further comprising a second end effector element movably coupled to said third distal joint, such that said first and second end effector elements are movable relative to, and independently of, one another.

17. The system of claim 12, wherein said articulate arm comprises a remote center of motion mechanism having macro degrees of freedom of movement that are redundant with the degrees of freedom of movement of the instrument around said first, second and third distal joint axes.

18. The system of claim 12, wherein said input commands comprise the operator moving at least one master control handle, wherein movement of said instrument corresponds to a scaled increment of said movement of said master control handle.

19. The system of claim 18, wherein the forces experienced by the instrument during a surgical procedure are reproduced at the master control handle to provide the operator with force feedback, wherein the reproduced forces at the master are scaled increments of the forces experienced by the instrument.

20. The system of claim 19, wherein the reproduced forces are reproduced in three degrees of freedom of movement of the master, corresponding to three degrees of freedom of movement of the instrument.

21. The system of claim 19, wherein the reproduced forces at the master correspond to an amplification of the forces experienced by the instrument.

22. The system of claim 12, wherein said slave articulate arm comprises a slave linkage having a number X of DOFs, X being at least 7, and wherein said master input linkage is characterized by a number Y of DOFs where Y is at least one fewer than X.

23. The system of claim 12, wherein said slave articulate arm and instrument have a combined X degrees of freedom of movement, and said master input linkage has Y degrees of freedom of movement, wherein Y is at least one fewer than X, wherein said controller is configured to resolve a redundancy in control due to the difference between the X and Y degrees of freedom of movement by applying a cost function to a range of possible joint configurations, each of which provides substantially the same location for the end effector member.

24. The system of claim 23, wherein X comprises 7 slave degrees of freedom of movement and Y comprises 6 master degrees of freedom of movement.

25. The system of claim 23, wherein X comprises 8 slave degrees of freedom of movement and Y comprises 7 master degrees of freedom of movement.

* * * * *